US011985979B2

(12) United States Patent
Carbone

(10) Patent No.: US 11,985,979 B2
(45) Date of Patent: May 21, 2024

(54) POPULATION GENETICS APPROACH TO BIOLOGICAL CONTROL OF MYCOTOXIN PRODUCTION

(71) Applicant: NORTH CAROLINA STATE UNIVERSITY, Raleigh, NC (US)

(72) Inventor: Ignazio Carbone, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 708 days.

(21) Appl. No.: 17/050,751

(22) PCT Filed: Apr. 29, 2019

(86) PCT No.: PCT/US2019/029668
§ 371 (c)(1),
(2) Date: Oct. 26, 2020

(87) PCT Pub. No.: WO2019/212975
PCT Pub. Date: Nov. 7, 2019

(65) Prior Publication Data
US 2021/0235706 A1 Aug. 5, 2021

Related U.S. Application Data

(60) Provisional application No. 62/664,421, filed on Apr. 30, 2018.

(51) Int. Cl.
*A01N 63/34* (2020.01)
*A01N 63/30* (2020.01)

(52) U.S. Cl.
CPC .............. *A01N 63/34* (2020.01); *A01N 63/30* (2020.01)

(58) Field of Classification Search
CPC ................................ A01N 63/30; A01N 63/34
See application file for complete search history.

(56) References Cited

FOREIGN PATENT DOCUMENTS

WO WO2014191917 12/2014

OTHER PUBLICATIONS

Andrews, M. et al. "Agriculture and the Microbiome" CAST Issue Paper, No. 68, 24 pages, 2020.
Gell et al. "Genetic map and heritability of Aspergillus flavus" Fungal Genetics and Biology, 144 (2020) 103478.
Lewis et al. "Biocontrol Strains Differentially Shift the Genetic Structure of Indigenous Soil Populations of Aspergillus flavus" Frontiers in Microbiology, vol. 10:1738, 17 pages, 2019.
Bandyopadhyay R et al: Frontiers in Biosynthesis and Management of Mycotoxins: From one to many: Effective aflatoxin management in farmers' fields in West and East Africa Phytopathology: 2014 APS-CPS Joint Meeting Abstracts, 104(104):139 2014.
Horn B W et al: "Sexual reproduction and recombination in the aflatoxin-producing fungus *Aspergillus parasiticus*" Fungal Genetics and Biology, 46(2):169-175 2009.
Shenge et al: "Interactions among active ingredients of a multi-isolate aflatoxin biocontrol product" Phytopathology, p. 131 2017 APS Annual Meeting San Antonio, Texas, U.S.A. Retrieved from the Internet: https://apsjournals.apsnet.org/doi/10.
Dorner, Joe W., et al., "Aflatoxin Reduction in Corn Through Field Application of Competitive Fungi", Journal of Food Protection, vol. 62, No. 6, 1999, 650-656.
Geiser, David M., et al., "Cryptic speciation and recombination in the aflatoxin-producing fungus *Aspergillus flavus*", Proc. Natl. Acad. Sci. USA, vol. 95, 1998, 388-393.
Geiser, David M., et al., "The Phylogenetics of Mycotoxin and Sclerotium Production in Aspergillus flavus and Aspergillus oryzae", Fungal Genetics and Biology 31, 2000, 169-179.
Molo, Megan S., et al., "Asymmetrical lineage introgression and recombination in populations of Aspergillus flavus: Implications for biological control", Plos One, 17(10): e0276556, 2022.
International Search Report and Written Opinion corresponding to PCT/US2019/029668, dated Aug. 15, 2019, 17 pages.
Horn, Bruce , et al., "Sexual reproduction in Aspergillus flavus", Mycologia, 101(3):423-429 2009.
Moore, Geromy G., et al., "Sexuality Generates Diversity in the Aflatoxin Gene Cluster: Evidence on a Global Scale", PLOS Pathogens, 9(8):1-12 2013.
Olarte , et al., "Effect of sexual recombination on population diversity in aflatoxin production by Aspergillus flavus and evidence for cryptic heterokaryosis", Mol Ecol., (6):1453-76 2012.
Ramirez-Prado, Jorge H., et al., "Characterization and population analysis of the mating-type genes in Aspergillus flavus and Aspergillus parasiticus", Fungal Genet Biol, 45(9):1292-1299 2008.
European Examination Report corresponding to EP 19796568.4; dated Oct. 31, 2023 (13 pages).
Chang, Perng-Kuang, "Aspergillus flavus La3279, a component strain of the Aflasafe™ biocontrol product, contains a partial aflatoxin biosynthesis gene cluster followed by a genomic region highly variable among A. flavus isolates", International Journal of Food Microbiology 366: 109559, 2022.
Moore, Geromy G., "Practical considerations will ensure the continued success of pre-harvest biocontrol using non-aflatoxigenic Aspergillus flavus strains", Crit Rev Food Sci Nutr. 62(15): 4208-4225, 2022.
Ortega-Beltran, Alejandro, et al., "Contributions of integrated aflatoxin management strategies to achieve the sustainable development goals in various African countries", Global Food Security 30: 100559, 2021.

*Primary Examiner* — Ruth A Davis
(74) *Attorney, Agent, or Firm* — Myers Bigel, P.A.

(57) ABSTRACT

The invention relates to methods for controlling mycotoxin production in field populations of heterothallic and homothallic filamentous fungi through application of biocontrol compositions comprising selected strains of the heterothallic and homothallic filamentous fungi, the selected strains having a lineage of low mycotoxin production or no mycotoxin production and having opposite mating types (heterothallic) or both mating types (homothallic) (e.g., MAT1-1, MATT-2).

12 Claims, 21 Drawing Sheets

Specification includes a Sequence Listing.

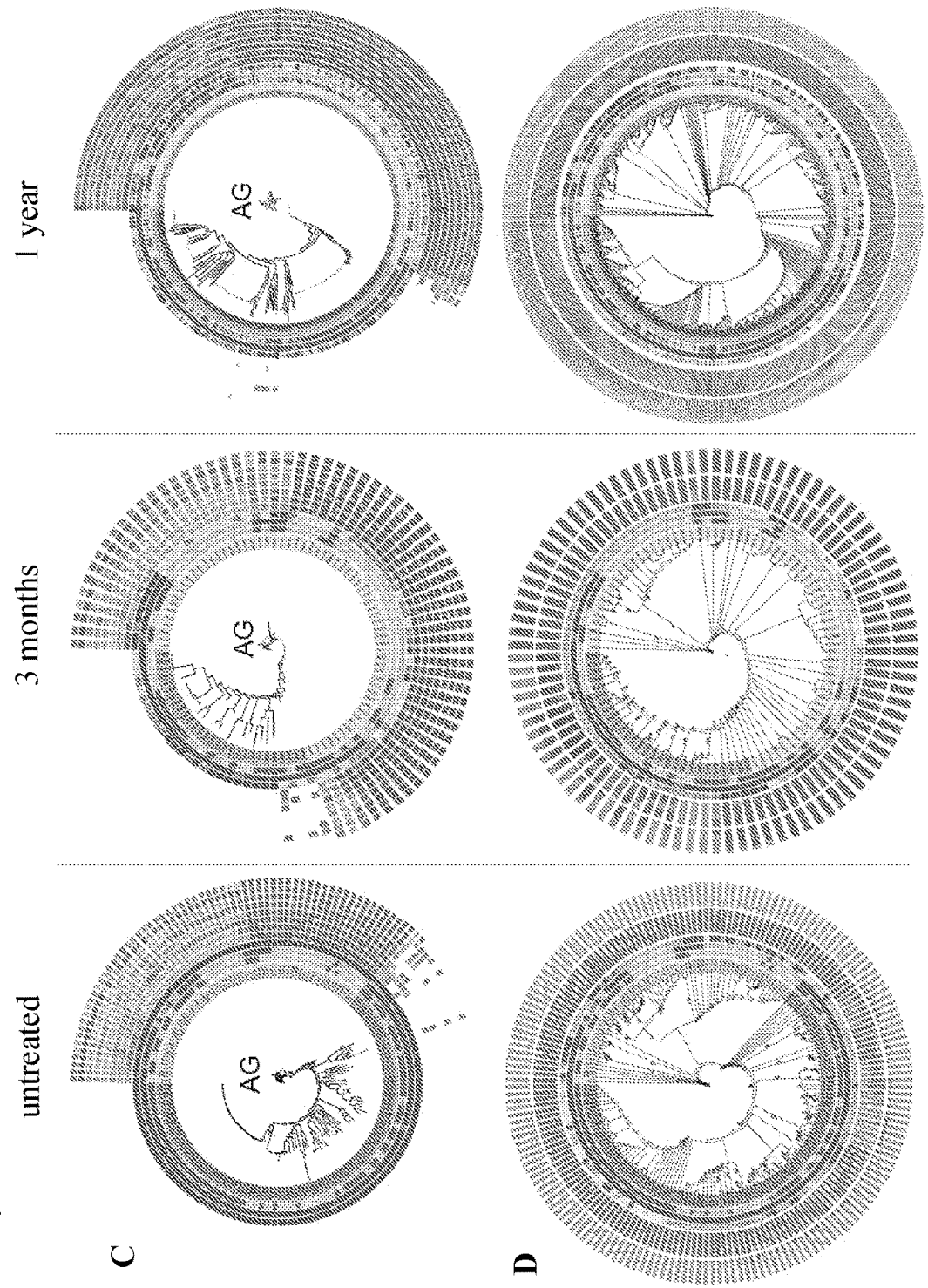
FIG. 6, cont.

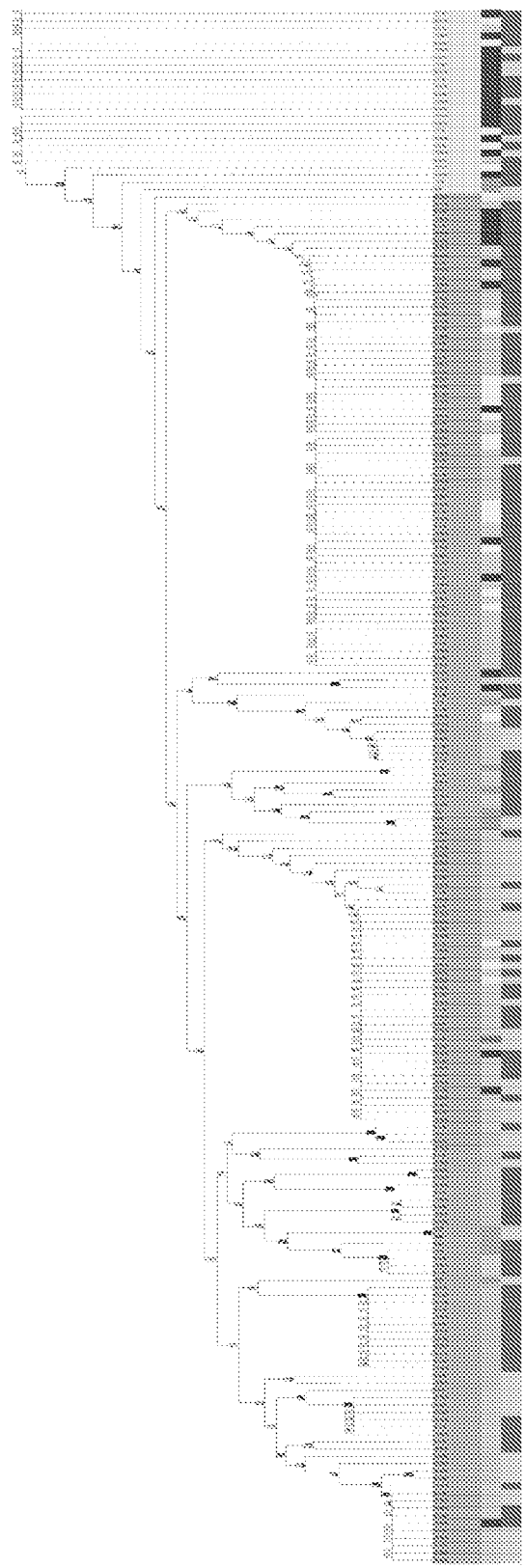
FIG. 9C, cont.

POPULATION GENETICS APPROACH TO BIOLOGICAL CONTROL OF MYCOTOXIN PRODUCTION

STATEMENT OF PRIORITY

This application claims the benefit, under 35 U.S.C. § 119 (e), of U.S. Provisional Application No. 62/664,421 filed on Apr. 30, 2018, the entire contents of which is incorporated by reference herein.

STATEMENT OF GOVERNMENT SUPPORT

This application is a 35 U.S.C. § 371 national phase application of International Application No. PCT/US2109/029668, which claims the benefit, under 35 U.S.C. § 119 (e), of U.S. Provisional Application No. 62/664,421 filed on Apr. 30, 2018, the entire contents of each of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 5051.934_ST25.txt, 3066 bytes in size, generated on Oct. 26, 2020 and filed via EFS-Web, is provided in lieu of a paper copy. This Sequence Listing is hereby incorporated by reference into the specification for its disclosures.

FIELD OF THE INVENTION

The invention relates to methods for controlling mycotoxin production in field populations of heterothallic and homothallic filamentous fungi through application of biocontrol compositions comprising selected strains of the heterothallic and homothallic filamentous fungi.

BACKGROUND OF THE INVENTION

Mycotoxins are secondary metabolites produced by various fungi. These toxins pose significant health risks to both humans and animals, and are therefore regulated by the US Food and Drug Administration. A variety of management practices have been developed to reduce mycotoxin contamination in corn, peanuts and other crops. Aflatoxins and fumonisins are mycotoxins produced by *Aspergillus flavus* and *Fusarium verticillioides*, respectively, that commonly contaminate corn in the southeastern United States. Because of the health and economic consequences of mycotoxin contamination, it is important to have management practices that are successful in reducing the levels of mycotoxins in food crops.

The present invention overcomes previous shortcomings in the art by providing a biocontrol approach that utilizes population genetics for preparation of a biocontrol composition that can be used to reduce mycotoxin production in a heterothallic filamentous fungal population in a field.

SUMMARY OF THE INVENTION

One aspect of the invention provides a biocontrol method for reducing mycotoxin production in a field population of one or more heterothallic filamentous fungi, the method comprising: applying a biocontrol composition to a plant, a plant part and/or a soil, the biocontrol composition comprising an effective amount of propagules (e.g., colony forming units) of at least two strains of the one or more heterothallic filamentous fungi, wherein the at least two strains comprise a first strain and a second strain of the one or more heterothallic filamentous fungi, each strain comprising a lineage of low mycotoxin production or no mycotoxin production, wherein the first strain further comprises a MAT1-1 mating type and the second strain further comprises a MAT1-2 mating type, wherein the amount of propagules of the at least two strains of the one or more heterothallic filamentous fungi is effective to promote mating between compatible mating partners in the field population and the at least two strains, thereby increasing the ratio of strains having the lineage of no or low mycotoxin production in the field population of the one or more heterothallic filamentous fungi and reducing mycotoxin production by the field population of the one or more heterothallic filamentous fungi.

A second aspect of the invention provides a biocontrol method of sustainably reducing mycotoxin production in a field population of one or more heterothallic filamentous fungi, comprising shifting the lineage of the field population of the one or more heterothallic filamentous fungi to low mycotoxin production or no mycotoxin production, the method comprising: applying a biocontrol composition to a plant, a plant part and/or a soil, the biocontrol composition comprising an effective amount of propagules of at least two strains of the one or more heterothallic filamentous fungi, wherein the at least two strains comprise a first strain and a second strain, each strain comprising a lineage of being a low producer or a non-producer of at least one mycotoxin, wherein the first strain further comprises a MAT1-1 mating type and the second strain further comprises a MAT1-2 mating type, wherein the amount of propagules of the at least two strains of the one or more heterothallic filamentous fungi is effective to promote mating between compatible mating partners in the field population and the at least two strains, thereby shifting the lineage of the field population of the one or more heterothallic filamentous fungi to low mycotoxin production or no mycotoxin production and sustainably reducing mycotoxin production in a field population of the one or more heterothallic filamentous fungi.

A third aspect of the invention provides a biocontrol method for reducing aflatoxin production in a field population of *Aspergillus flavus*, comprising applying a biocontrol composition to a plant, a plant part and/or a soil, the biocontrol composition comprising an effective amount of propagules of at least two strains of *A. flavus*, wherein the at least two strains of *A. flavus* comprise a first strain and a second strain, each strain comprising a lineage of IB and being a low producer or a non-producer of aflatoxin, wherein the first strain further comprises a MAT1-1 mating type and the second strain further comprises a MAT1-2 mating type, wherein the amount of propagules of the at least two strains of *A. flavus* is effective to promote mating between compatible mating partners in the field population and the two strains of *A. flavus*, thereby increasing the ration of strains having the IB lineage in the field population of *A. flavus* and reducing aflatoxin production by the field population of *A. flavus*.

A fourth aspect of the invention provides a biocontrol method of sustainably reducing aflatoxin production in a field population of *Aspergillus flavus*, comprising shifting the lineage of the field population of *A. flavus* to low toxin production or no toxin production, the method comprising: applying a biocontrol composition to a plant, a plant part and/or a soil, the biocontrol composition comprising an effective amount of propagules of at least two strains of *A. flavus*, wherein the at least two strains comprise a first strain and a second strain, each strain comprising a lineage of IB and being a low producer of aflatoxin or a non-producer of aflatoxin, wherein the first strain further comprises a MAT1-1 mating type and the second strain further comprises a MAT1-2 mating type, and wherein the amount of propagules of the at least two strains of *A. flavus* is effective to promote mating between compatible mating partners in the field population and the at least two strains, thereby shifting the lineage of the field population of *A. flavus* to low aflatoxin production or no aflatoxin production and sustainably reducing aflatoxin production in the field population of *A. flavus*.

A fifth aspect of the invention provides a biocontrol composition comprising an effective amount of propagules (e.g., colony forming units, cfu) of at least two strains of one or more heterothallic filamentous fungi, wherein the at least two strains comprise a first strain and a second strain of the one or more heterothallic filamentous fungi, each strain comprising a lineage of low mycotoxin production or no mycotoxin production, wherein the first strain further comprises a MAT1-1 mating type and the second strain further comprises a MAT1-2 mating type.

These and other aspects of the invention are set forth in more detail in the description of the invention below.

The phylogenies displayed in the center of the rings are based on maximum likelihood searches using variation across the entire genome, with branches scaled to the number of nucleotide substitutions per site; the scale bar is shown at bottom of tree in panel B. Patristic distance is shown in the eight outermost rings and used to examine variation among all strains as compared to either Afla-Guard=AG (A) or AF36 (B). The distance of each strain from AG or AF36 as a reference is shown using a heat map, where a value of zero indicates very close genetic similarity of the strain to the reference and a value of one is high genetic dissimilarity. In panel C, the patristic scale is adjusted so that the maximum color (darkest in grayscale) value falls within lineage IB, revealing heterogeneity in patristic distances and potential clonality and recombination in lineage IB, not observed in panel A. Panel D shows results from STRUCTURE analysis in the two outermost rings; the inner rings are the best clusters inferred from STRUCTURE LnP(D) and the outer rings are distinct clusters inferred using Evanno's method; distinct genetic clusters are indicated with different shades of gray.

Figure 6:
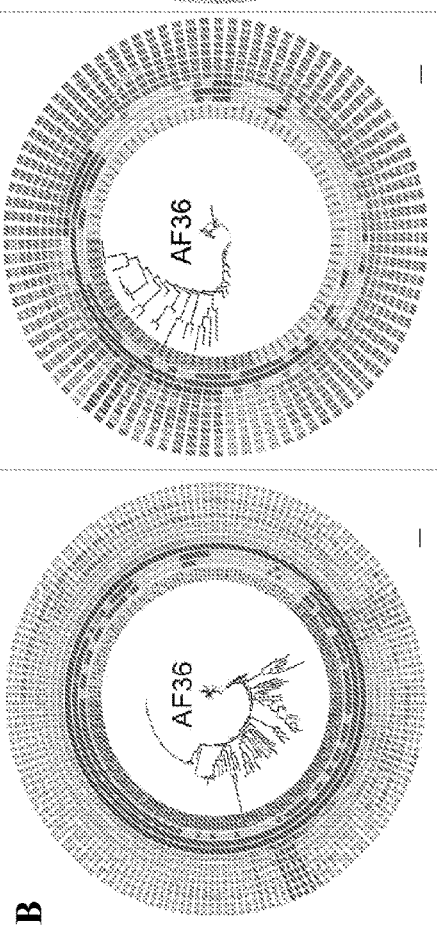
FIG. 6 shows longitudinal population dynamics of *A. flavus* across four states. *A. flavus* biocontrol strains Afla-Guard=AG and AF36 were applied to cornfields in TX, NC, AR and IN. In panel A, panel B and panel C, the four innermost rings show the overall recovery and frequency of *A. flavus* evolutionary lineage (IB, IC), mating types (MAT1-1, MAT1-2), aflatoxin (AF) cluster configuration (full, partial, missing) and treatment (untreated, Afla-Guard, AF36) across field populations. In panel D, the treatment ring was replaced with sampling locations for field experiments (TX, NC, AR, IN) and reference strains (GA, AZ).
Figure 6:
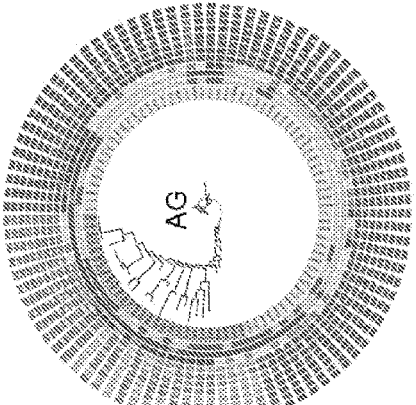
Figure 6:
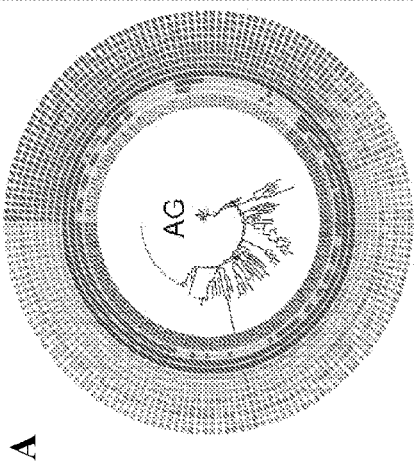
Figure 7A:
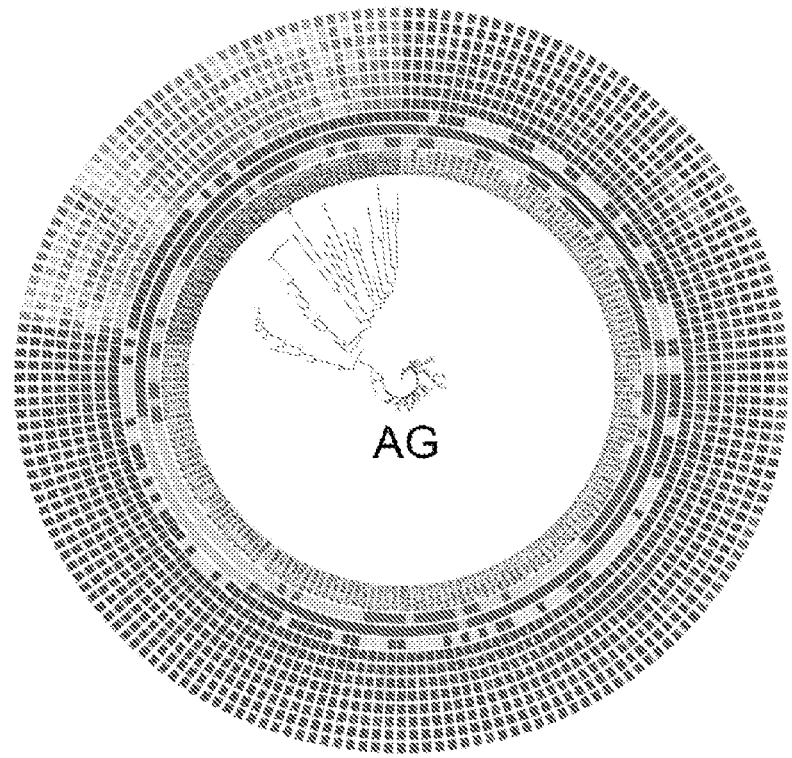
Figure 7B:
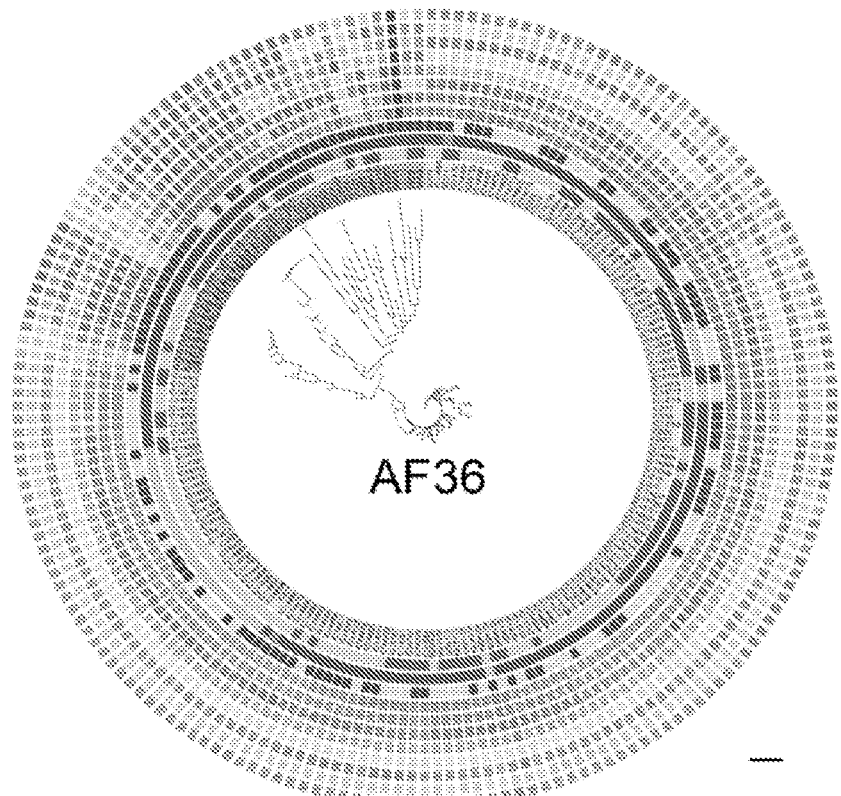
Figure 7C:
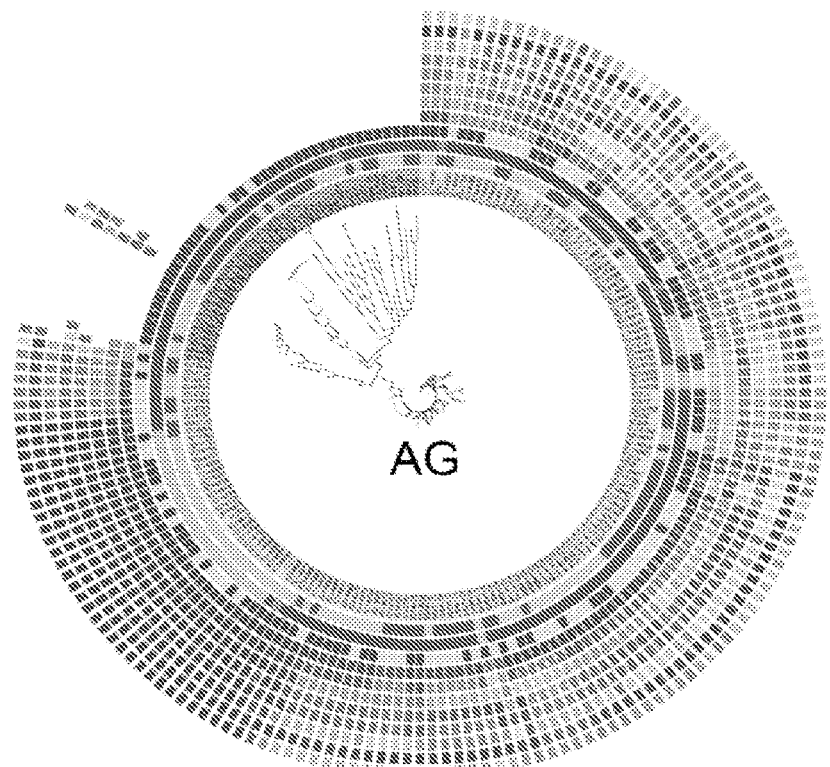
Figure 7D:
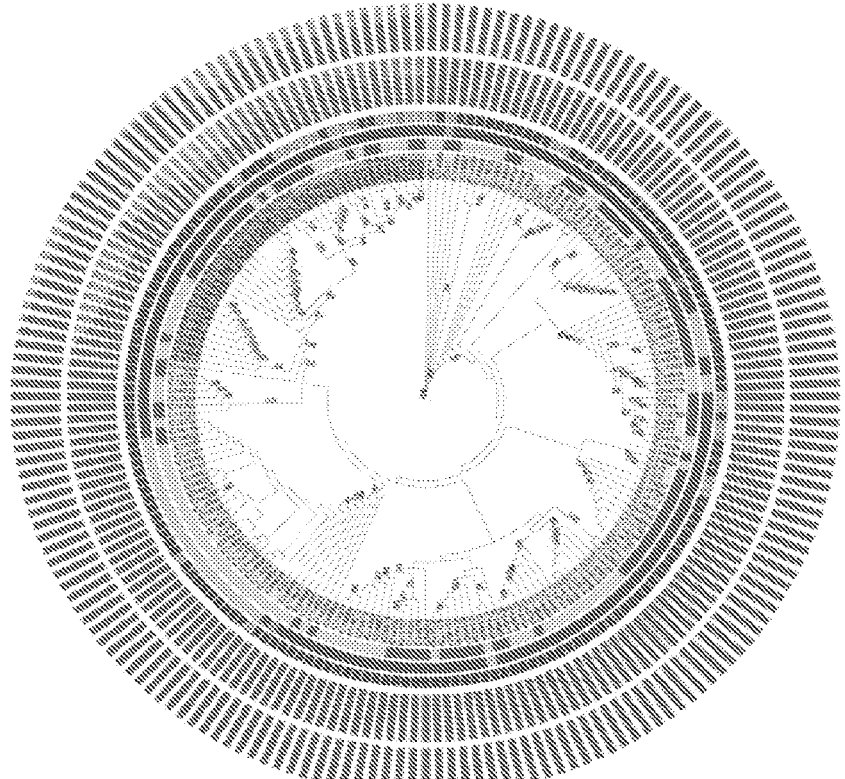

FIGS. 7A-D shows the population structure of *A. flavus* in commercial TX cornfields. The phylogenies displayed in the center of the rings are based on maximum likelihood searches using variation across the entire genome, with branches scaled to the number of nucleotide substitutions per site; the scale bar is shown at bottom of tree in FIG. 7B. The innermost rings include all of the legend categories shown in FIG. 6. The eight outermost patristic rings show the extent of clonality and recombination with respect to Afla-Guard (FIG. 7A) or AF36 (FIG. 7B); AF36 was included in the patristic analysis of the TX cornfields, that were treated only with AG, to determine if AF36 occurred naturally in untreated plots. In FIG. 7C, patristic distances were adjusted to filter out lineage IC strains that represent distances greater than one (white). The two outermost STRUCTURE rings (FIG. 7D) show the number of distinct genetic clusters and degree of lineage admixture based on LnP(D) for the inner ring and Evanno for the outer; distinct genetic clusters are indicated with different shades of gray.

Figure 8A:
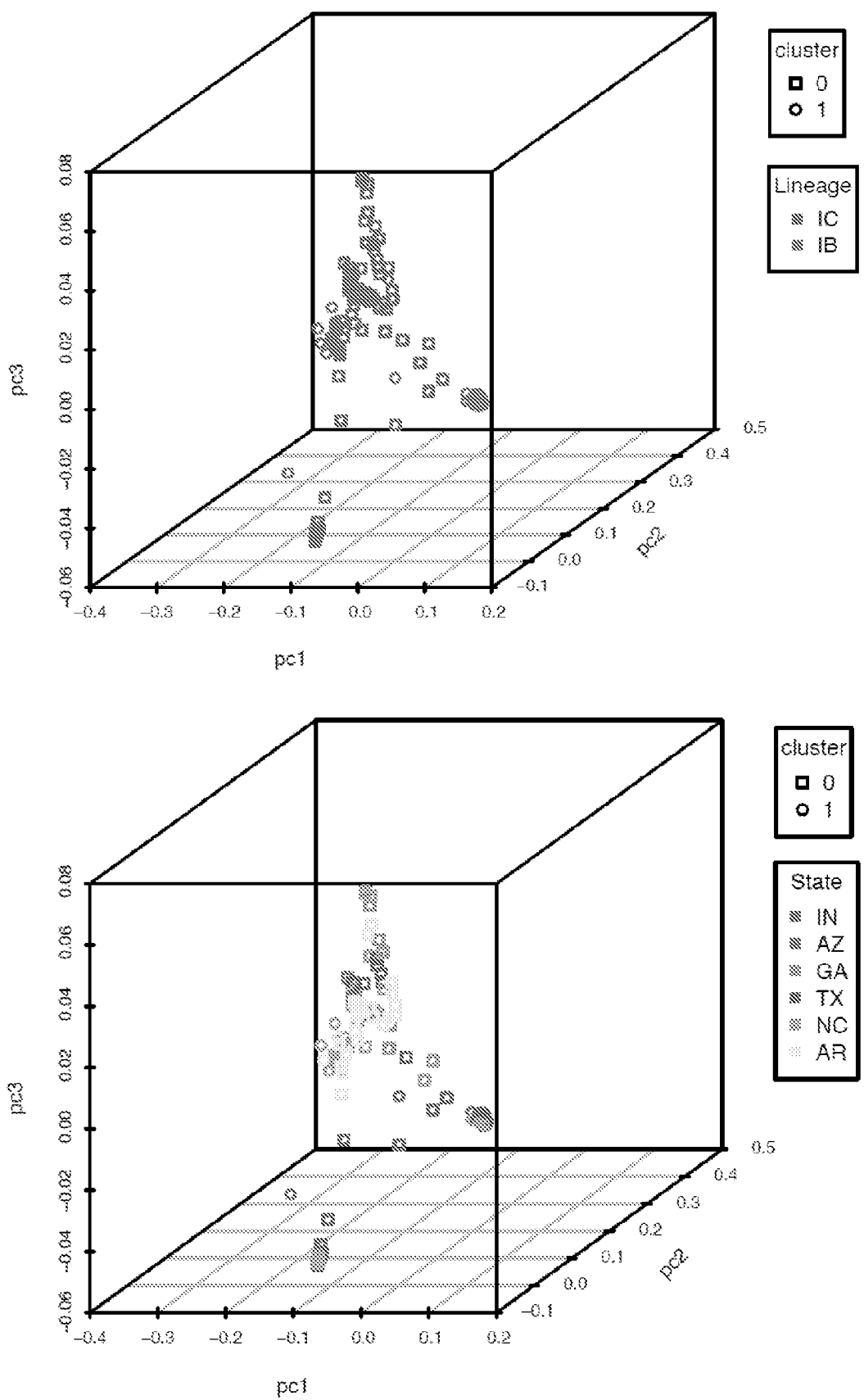
Figure 8B:
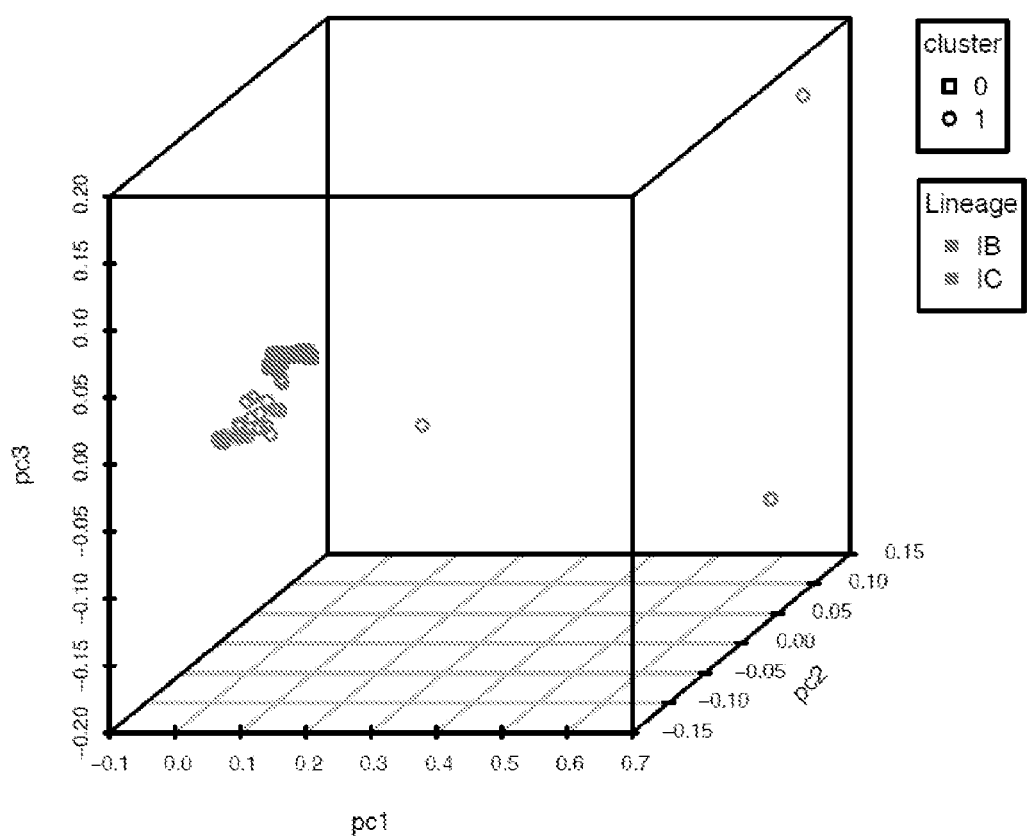
Figure 8B:
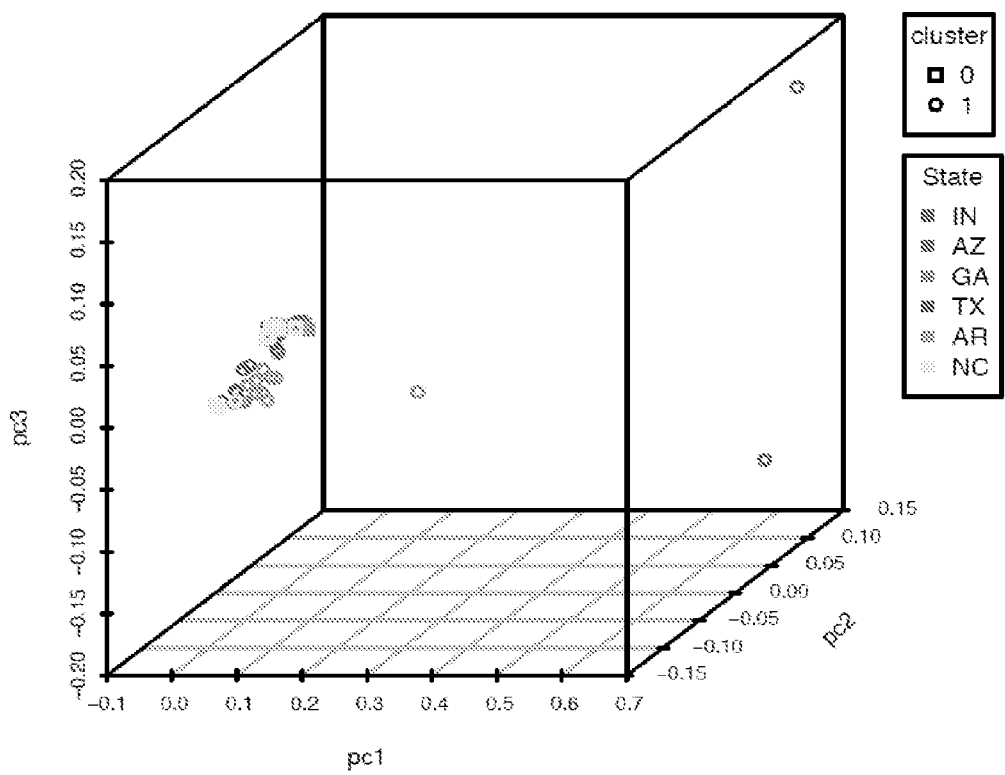
Figure 8C:
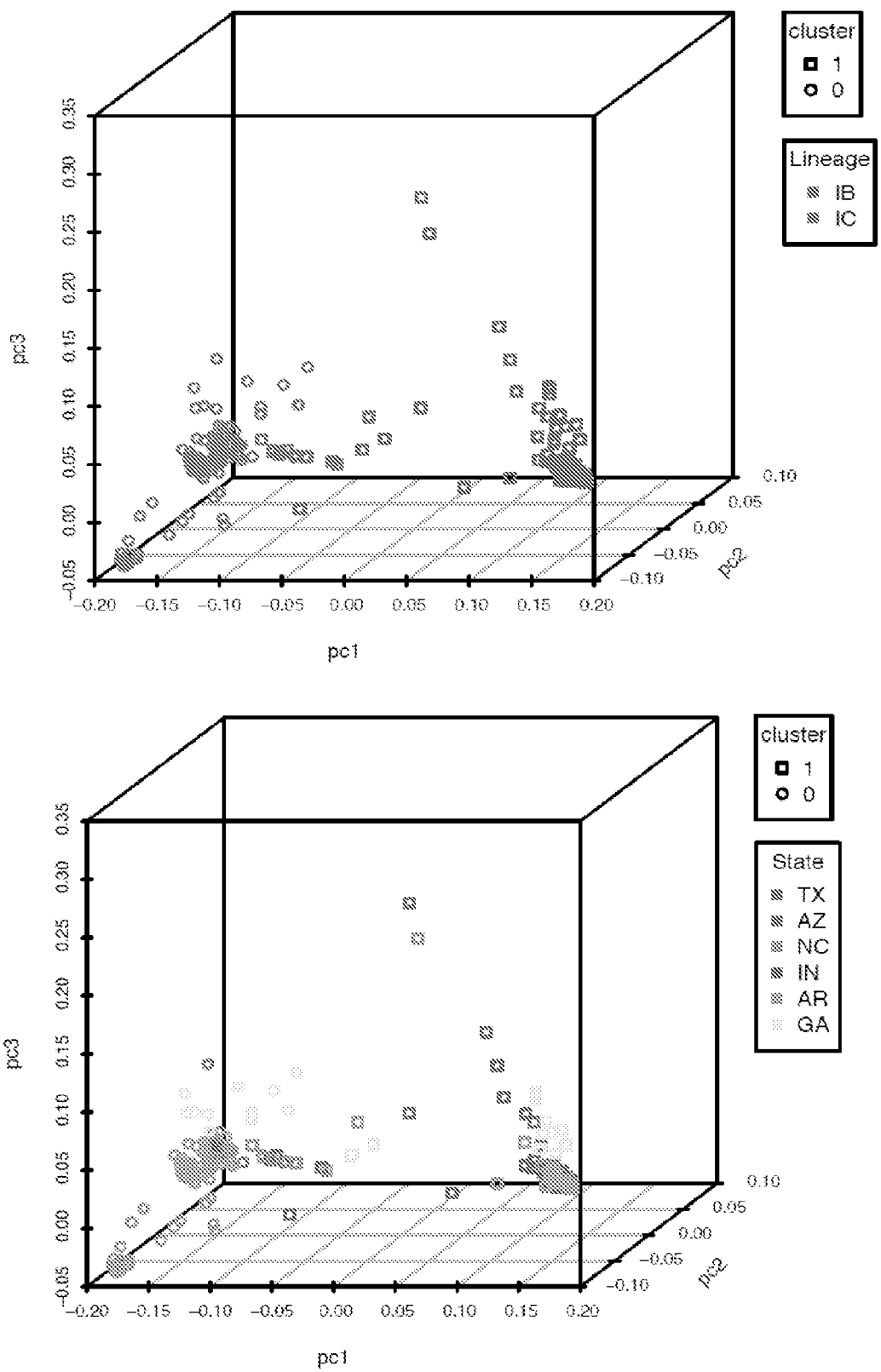
Figure 8D:
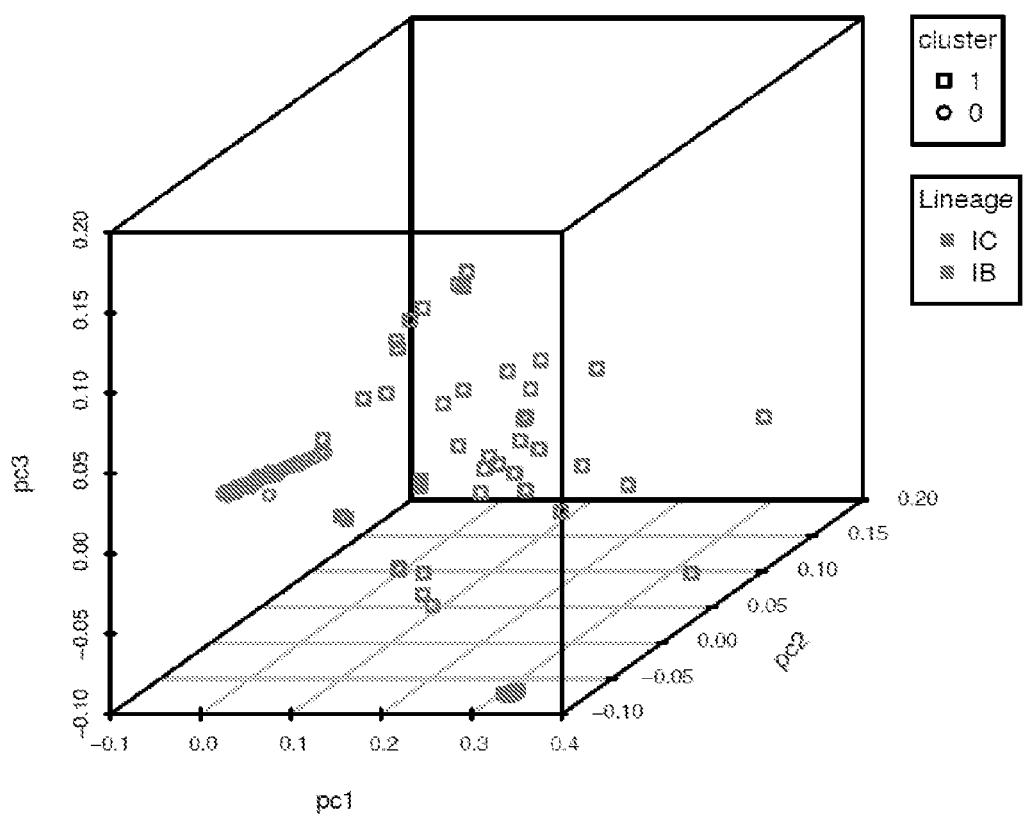
Figure 8D:
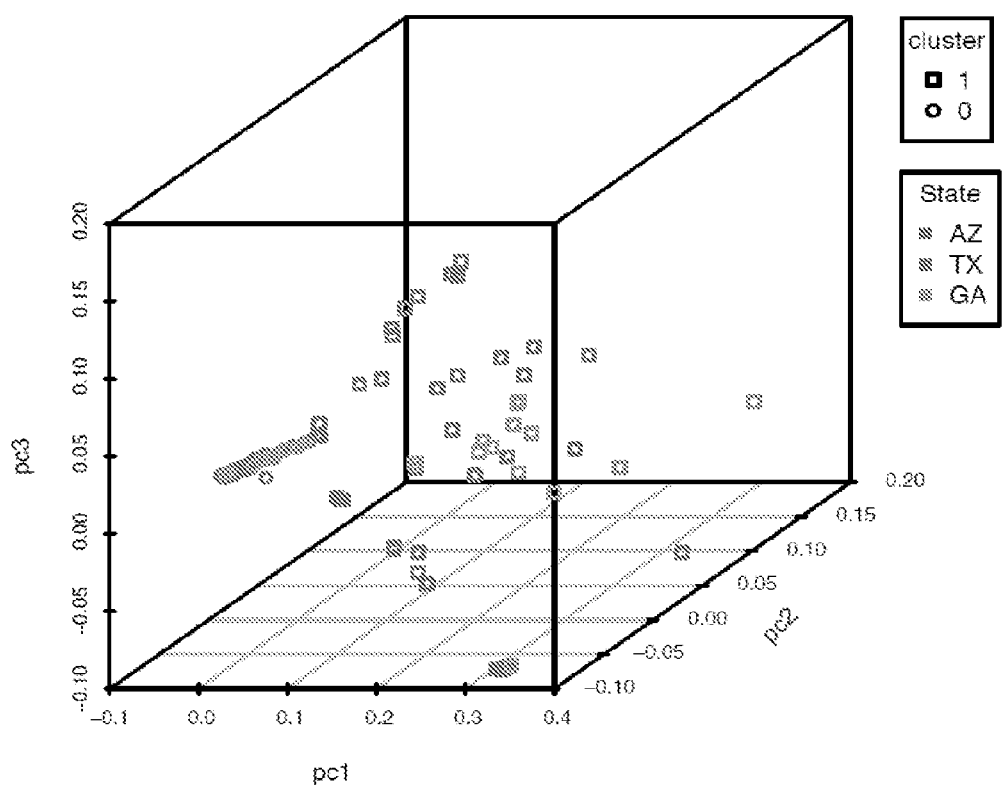

FIGS. 8A-D shows the population structure using principal component analysis (PCA). For each treatment time point two PCA scatter plots are shown for genome-wide variation in *A. flavus* across TX, NC, AR and IN (reference strains are from GA and AZ); FIG. 8A (untreated), FIG. 8B (three months), FIG. 8C (one year), FIG. 8D (three years). The PCA cubes show the distribution of individuals based on their membership in one of two clusters inferred from the Gap statistic and overlaid with lineage (PCA cube upper panel) or state (PCA cube in lower panel). The different color scheme (shown in grayscale) and shapes are unique for each PCA cube.

FIGS. 9A-D shows the phylogenetic congruence using the Hypha module in Mesquite. Phylogenetic congruence of each chromosome phylogeny compared to the total evidence display tree for different time points is shown using grids on node partitions (FIG. 9A (untreated), FIG. 9B (three months), FIG. 9C (one year), FIG. 9D (three years)). In each grid bootstrap support values are displayed with each box from left to right representing one of eight chromosomes; the box on the bottom right is for the mitochondrial genome. Shades in grids represent node bipartitions that were supported at a bootstrap support value ≥70% (black color), <70% (white color), and missing or inapplicable (grey color). Phylogenetic incongruency was represented as high conflict (white color) and low conflict (black color). Additional attributes (lineage, state, treatment and mating type) are shown in columns adjacent to the strain names.

FIGS. 10A-D shows chromosomal LD plots. LD plots are displayed using Haploview for each chromosome across four different time points. In each LD plot, black lines outline the edge of the spine of strong LD. In the coloring scheme, red (darkest in grayscale) represents strong LD (LOD≥2, D'=1), shades of pink/red (shades of gray) represent intermediate LD (LOD≥2, D'<1), blue (lightest in grayscale) represents weak LD (LOD<2, D'=1) and white represents no LD (LOD<2, D'<1).

DETAILED DESCRIPTION

The present invention now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of 10%, +5%, ±1%, ±0.5%, or even 0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control. Thus, in some aspects of the present invention, applying a composition of the invention to a plant, plant part, or soil results in an increase in the ratio of low mycotoxin production lineage versus high mycotoxin production lineage in a field population of heterothallic filamentous fungi as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount. Thus, in some aspects of the present invention, applying a composition of the invention to a plant, plant part, or soil results in a decrease in mycotoxin production in a field population of heterothallic filamentous fungi as compared to a control.

The term "native strain" as used herein refers to a fungal strain that is indigenous to and adapted to the particular region being referenced. A native strain may be indigenous and adapted to a single region of any size (e.g., an area within a single state or country, an entire state or country, or one or more adjacent states or countries) or it may be indigenous to two or more separate regions of any size (e.g., one or more separate regions located in one or more states or countries). A native strain can include a strain that may have once been introduced (naturally or by human intervention) to a region but is now established and adapted to that region. A "native strain" may be a low toxin producer or it may be atoxigenic. In some embodiments of the invention, enhanced introgression of sexually compatible lineage IB strains into native strains may be used to provide sustained reductions in aflatoxin levels over subsequent generations.

*A. flavus* vegetative compatibility groups are dispersed widely in the Continental US (see e.g., Example 4 showing widespread dispersal of strains from TX to NC). Strains that produce more spores may be able to disperse over larger distances whereas strains that produce more sclerotia have restricted ranges and longer residence times in native environments. When clonality predominates over sexual reproduction, clonal propagules can disperse over long distances and can be distinguished from resident native strains. Historical data may be used to identify invading strains that undergo genetic exchange and recombination with native strains. Longitudinal studies of *A. flavus* populations in soil and corn ears provide a baseline understanding of the native population genetic structure; these native patterns of admixture change when non-indigenous strains are introduced intentionally or unintentionally.

*Aspergillum flavus* is a cosmopolitan fungus that contaminates maize and other oil seed crops worldwide with carcinogenic aflatoxins Although clonality (i.e. asexual reproduction) is predominant in *A. flavus* populations, infrequent sexual reproduction generates new genetic variation and maintains aflatoxin production in populations, thereby exacerbating aflatoxin contamination of crops. Extensive laboratory and field experiments have demonstrated that aflatoxin production is highly heritable, which translates to aflatoxin production being maintained over several generations. Aflatoxin production is a polygenic trait with several genes not involved directly in aflatoxin biosynthesis under the influence of environmental cues and changes. For example, elevated temperature and water stress conditions significantly promote expression of aflatoxin biosynthetic genes increasing aflatoxin production. Other environmental factors, namely nitrogen and carbon interact with promoters of aflatoxin biosynthetic genes to support or repress transcription. This ongoing genotype by environment interaction makes it challenging to manage and predict aflatoxin outbreaks.

The discovery of sexual reproduction in *A. flavus* has provided new perspectives on how the genetics and genomic composition of this fungus can influence its aflatoxin-producing potential. Specifically, we have determined that *A. flavus* has a bipolar mating system and individual strains have only one of two possible mating types: MAT1-1 or MAT1-2. Each strain is hermaphroditic with sclerotia functioning as female and conidia serving as a male during sexual reproduction. Sclerotia are hard melanized structures typically around 400 μm in diameter and conidia are asexual spore propagules. Sclerotia are transformed into stromata during sexual reproduction. Hermaphroditism enables reciprocal crosses between sclerotia and conidia, but invariably only one sclerotia-conidia combination is highly fertile while the reciprocal combination exhibits very low fertility. For example, a cross is highly fertile when the *sclerotium* of the MAT1-1 parent strain is mated with conidium of the MAT1-2 parent but of low fertility when the conidium of the MAT1-1 parent strain is mated with *sclerotium* of the MAT1-2 parent. Results from experimental and field crosses indicate extensive variation in sexual fertility with the degree of fertility largely determined by the sclerotial parent. This has significant implications for current biocontrol methods, which release a high density of conidia of a single *A. flavus* strain. When clonality predominates in populations, fewer isolates go through sexual reproduction with vegetative or asexual propagation predominating and aflatoxin levels being mostly determined by a few genotypes (i.e. vegetative compatibility groups or VCGs) that are able to grow better vegetatively and produce more sclerotia and conidia. The importance of sexual reproduction in maintaining aflatoxin production is evidenced by several species in *Aspergillus* section *Flavi*, for example, *A. caelatus* and *A. tamarii*, which are predominantly asexual, have mating type frequency distributions that are skewed to one mating type, and are non-aflatoxigenic. Aflatoxin-producing species such as *A. flavus* may become more non-aflatoxigenic, if 1) strains that do not make aflatoxin make more spores, 2) specific environmental conditions are present that are non-conducive for aflatoxin production, 3) sexual reproduction is too infrequent to spread and maintain the determinants of aflatoxigenicity in populations, or a combination of several of the above processes.

The current biological control strategies using EPA approved *A. flavus* non-aflatoxigenic strains, AF36 (*A. flavus* strain NRRL 18543) and AFLA-GUARD® strain NRRL 21882, are believed to work because they artificially and transiently increase the frequency of one genotype, such that populations are predominantly of a single non-aflatoxigenic mating type, precluding sexual reproduction. However, because this approach is not working in concert with the reproductive and mating biology of this fungus, the reduction in aflatoxigenicity is not sustainable and biocontrols need to be reapplied every growing season. We now have a better understanding of the underlying population genetic and evolutionary processes that are occurring when biocontrol strains are applied to fields. Widespread sampling of field populations has revealed the existence of two distinct *A. flavus* evolutionary lineages, designated as lineage IB and IC. Lineage IB strains are frequently non-aflatoxigenic, whereas lineage IC strains vary widely in their ability to make aflatoxins, ranging from those that are non-aflatoxigenic (e.g., AF36) to those that are potent producers of aflatoxins. While both the AFLA-GUARD® strain and AF36 are non-aflatoxigenic and effective in reducing aflatoxin levels, their aflatoxin-producing potential is different. The AFLA-GUARD® strain is a lineage IB strain and is missing the entire aflatoxin gene cluster and AF36 is a lineage IC strain with a full gene cluster, and with the exception of a single nonsense mutation in pksA (=aflC; polyketide synthase gene), AF36 is closely related to other aflatoxin-producing strains in lineage IC.

Laboratory and field experiments have shown that both the AFLA-GUARD® strain and AF36 are fertile. In field experiments where the AFLA-GUARD® strain and AF36 are applied separately to replicate plots, and compared to untreated plots, both lineages are recovered from corn kernels 3 months and one year after initial application. Prior to the application of biocontrol agents both lineages are present in untreated plots but mating type distributions within each lineage are skewed, which indicates that populations are predominantly clonal. Three months after biocontrol application, clonality is artificially accentuated as a result of the high density release of MAT1-2 biocontrol strains; however, one year later, mating type ratios within lineages IB and IC are close to 1:1, which is indicative of sexual reproduction. So, while the biocontrol agents have their initial intended action of reducing aflatoxin levels, one year later the populations have recombined, restoring equilibrium between lineages IB and IC, and consequently, the biocontrols need to be reapplied. The recurrent sampling of both lineages IB and IC in field populations worldwide indicates their importance in the ecology and evolution of this fungus. Although both lineages are present in fields, their frequencies can be different. A lineage skew may arise from 1) differential lineage-specific sexual recombination and fertility, 2) differential lineage-specific spore production, or 3) differential responses of lineages to changing environmental factors or latitude gradients. In fields where aflatoxin levels are consistently low over several years, there is a larger proportion of lineage IB isolates compared to IC and there is clear evidence of admixture among lineage IB isolates (i.e. approximately 1:1 distribution of MAT1-1:MAT1-2). Currently, these two approved aflatoxin biocontrols are made up of the same mating type (MAT1-2), but belong to different evolutionary lineages; with the AFLA-GUARD® strain having lineage IB and AF36 having lineage IC. Mating experiments in the laboratory and field have shown that overall fertility of *A. flavus* strains in lineage IB is lower than strains in lineage IC.

Mechanistically, the reduction in aflatoxin levels is the result of clonal amplification and genetic admixture. Although both the AFLA-GUARD® strain and AF36 are effective in reducing aflatoxin levels in the short term, their efficacy in the long-term depends on which lineage they belong to. Populations with a greater proportion of lineage IB strains relative to lineage IC have reduced aflatoxin levels. The present invention incorporates this observation into a new biocontrol strategy that releases strains of opposite mating type that belong to lineage IB at high densities. This results in a higher frequency of mating interactions between lineage IB and native strains. There is a strong directionality in cross fertility and significant differences in fertility between lineages, such that lineage IC harbored *A. flavus* strains having the highest fertility. The disproportionate mating access of lineage IB strains to female strains of high fertility in lineage IC results in unequal introgression of the lineage IB genetic background in field populations that are treated with compositions of the present invention. This then results in a larger proportion of lineage IB strains in the population that are non-aflatoxigenic or low aflatoxin producers such that the net effect is a lowering of aflatoxin levels in field populations. Moreover, the introgression of lineage IB into native populations offers the potential for sustained reductions in aflatoxin levels over subsequent generations.

Both *A. flavus* evolutionary lineages (IB and IC) are widely dispersed along a latitude gradient and transcend state boundaries. Thus, it may be possible for a single biocontrol formulation to be effective across different latitudes and environmental conditions. For example, the AFLA-GUARD® strain has been shown to be effective in mitigating aflatoxin contamination in Texas and North Carolina. Under field conditions, mating success is dependent upon genetic diversity in soil populations, thus selecting a mix of strains from lineage IB that are of different mating types and clonal backgrounds may be useful for mitigating aflatoxin contamination. These strain mixtures may be effective for different fields because the evolutionary lineage effect may be stronger than strain specific differences in reducing aflatoxin levels. Thus, for example, incorporating a complementary MAT1-1 strain from lineage IB into the AFLA-GUARD® formulation may improve the efficacy including long term effectiveness of biocontrol, particularly in fields that harbor highly fertile strains of both mating types.

While much is now known about *A. flavus* biology and evolution, the underlying mechanisms that result in lower aflatoxin levels have not been elucidated, nor has an approach been proposed that takes advantage of population biology to mitigate aflatoxin contamination in maize and other crops. Here, we describe a new genetically based biocontrol strategy that can sustainably reduce the aflatoxin producing potential of this agriculturally important fungus. This approach is also applied to other heterothallic toxin producing fungi including, but not limited to, additional toxin producing *Aspergillus* species and to *Fusarium* species that produce toxins.

Thus, in some embodiments, the present invention provides a biocontrol composition comprising an effective amount of propagules (e.g., colony forming units, cfu) of at least two strains of one or more heterothallic filamentous fungi (e.g., 2, 3, 4, 5, 6, 7, 8, 9, 10 strains and the like), wherein the at least two strains comprise a first strain and a second strain of the one or more heterothallic filamentous fungi, each strain comprising a lineage of low or no mycotoxin production, wherein the first strain further comprises a MAT1-1 mating type and the second strain further comprises a MAT1-2 mating type. In some embodiments, the ratio of the propagules of the first strain to propagules of the second strain in the biocontrol composition is about equal (e.g., for two strains the ratio may be about 1:1 (e.g., about 0.8:1 to about 1:1.2, about 0.9:1 to about 1:1:1, and the like).

In some embodiments, it may be advantageous to include more than one strain having a MAT1-1 mating type or a MAT1-1 mating type, for instance, when a particular mating type is rare in the population of heterothallic fungi. As an example, a biocontrol composition may comprise, a first strain, a second strain and a third strain, each strain comprising a lineage of low or no mycotoxin production, wherein the first strain further comprises a MAT1-1 mating type, the second strain further comprises a MAT1-1 mating type and the third strain further comprises a MAT1-2 mating type or the first strain further comprises a MAT1-1 mating type, the second strain further comprises a MAT1-2 mating type and the third strain further comprises a MAT1-2 mating type.

In some embodiments, a composition of the invention may comprise at least four strains, wherein at least two of the four strains are from at least two different species of heterothallic filamentous fungi. Thus, for example, a composition may comprise at least two strains of one heterothallic filamentous fungal species and at least two strains of a different heterothallic filamentous fungal species. In some embodiments, a composition of the invention may comprise 6, 8, 10 or more strains of heterothallic filamentous fungi.

In some embodiments, a composition of the present invention may further comprise an agriculturally acceptable carrier. An agriculturally-acceptable carrier of the present invention can include natural or synthetic, organic or inorganic material which is combined with the active component to facilitate its application to the plant, plant part, or soil. An agriculturally-acceptable carrier includes, but is not limited to, inert components, dispersants, surfactants, adjuvants, tackifiers, stickers, binders, or combinations thereof, that can be used in agricultural formulations. In some embodiments, an agriculturally acceptable carrier may be water or soil. In some embodiments, the agriculturally acceptable carrier is not water or soil.

Agriculturally acceptable carriers can be solid or liquid and are well known to those of skill in the art. Solid carriers include, but are not limited to, silicas, silica gels, silicates, talc, kaolin, limestone, lime, chalk, bole, loess, clay, attapulgite clay, bentonite, acid clay, pyrophillite, talc, calcite, corn starch powder, dolomite, diatomaceous earth, calcium sulfate, magnesium sulfate, magnesium oxide, ground synthetic materials, resins, waxes, fertilizers such as ammonium sulfate, ammonium phosphate, ammonium nitrate and ureas, products of vegetable origin such as cereal meal, tree bark meal, wood meal and nutshell meal (e.g., walnut shell powder), cellulose powders and the like; and combinations thereof. Non-limiting examples of liquid carriers include water, petroleum fractions, aromatic or paraffinic hydrocarbons, chlorinated hydrocarbons, and the like, and combinations thereof. Thus, liquid carriers can include, but are not limited to, xylene, methylnaphthalene and the like, vegetable oils such as soybean oil, cottonseed oil, corn oil and the like, dimethyl sulfoxide, acetonitrile, and combinations thereof.

In some embodiments, an agriculturally acceptable carrier of the present invention comprises a surface active agent (surfactant), which can be an emulsifying, dispersing or wetting agent of ionic or nonionic type. Non-limiting examples of surface active agents suitable for use with the compositions of the present invention, include alkyl benzene and alkyl naphthalene sulfonates, alkyl and alkyl aryl sulfonates, alkyl amine oxides, alkyl and alkyl aryl phosphate esters, organosilicones, fluoro-organic wetting agents, alkoxylated amines, sulfated fatty alcohols, long chain acid esters of sodium isothionate, esters of sodium sulfosuccinate, sulfated or sulfonated fatty acid esters, petroleum sulfonates, sulfonated vegetable oils, block copolymers, and polyoxyalkylene derivatives of the mono-higher fatty acid esters of hexitol anhydrides (e.g., sorbitan).

Non-ionic surface active agents useful with the compositions of this invention include, but are not limited to, polyglycol ether derivatives of aliphatic or cycloaliphatic alcohols, saturated or non-saturated fatty acids and alkylphenols, which have 3 to 10 glycol ether groups and 8 to 20 carbon atoms in the (aliphatic) hydrocarbon residue and 6 to 18 carbon atoms in the alkyl residue of the alkyl phenols. Other non-limiting examples of suitable non-ionic surface active agents include the water-soluble, 20 to 200 ethylene glycol ether groups containing polyadducts of ethylene oxide and polypropylene glycol, ethylene diamino polypropylene glycol and alkyl polypropylene glycol with 1 to 10 carbon atoms in the alkyl moiety. Additional non-limiting examples of non-ionic surface active agents include nonylphenol polyethoxy ethanols, castor oil polyglycol ether, fatty acid esters of polyoxy ethylene sorbitan, such as polyoxy ethylene sorbitan trioleate, tributyl phenoxy polyethoxy ethanol, polyethylene glycol, Tween serials such as polyoxyethylene sorbitan monolaurate, polyoxyethylene sorbitan monopalmitate, polyoxyethylene sorbitan monooleate, and the like.

Non-limiting examples of dispersants useful with the compositions of the present invention include methyl cellulose, polyvinyl alcohol, sodium lignin sulfonates, calcium lignosulfonates, polymeric alkyl naphthalene sulfonates, sodium naphthalene sulfonate, polymethylene binaphthalene sulfonate, and neutralized polyoxyethylated derivatives or ring-substituted alkyl phenol phosphates. In additional embodiments of this invention, the compositions of the invention may further comprise stabilizers, such as magnesium aluminum silicate, xanthan gum and the like.

Accordingly, in some embodiments, the compositions of the invention may be mixed with one or more agriculturally acceptable carriers, solid or liquid, and prepared by various means, e.g., by homogeneously mixing, grinding and/or blending the composition(s) with suitable carriers using conventional formulation techniques.

The compositions of the present invention can be made in any formulation suitable for applying to or contacting with a plant, plant part or soil. Formulations suitable for contacting the compositions of the invention to a plant or part thereof include, but are not limited to, a spray, a suspension, a powder, a granule, a mist, an aerosol, a foam, paste, emulsions (e.g., in oil (vegetable or mineral), or water or oil/water), a capsule, and combinations thereof.

In some embodiments, the fungal strain may be grown in/on a medium including but not limited to a seed (e.g., heat killed seed; e.g., heat-killed wheat seed, heat-killed barley seed, and the like) or bioplastic granule/pellet/particle, wherein the fungus colonizes the medium, and the colonized medium may then be used to disperse the propagules of the fungal strain(s). Two or more strains may be grown together on the same media to produce a composition of the invention or each strain may be grown separately on a medium (on the same or different types of media) and then mixed together to produce a composition of the invention comprising at least two strains of a heterothallic filamentous fungus selected as described herein. Bioplastic granules/pellets/particles are well known and comprise artificially generated polymers including, but not limited to those comprising polyesters (e.g, polylactic acid (PLA), or polyhydroxyalkanoate (PHA), and the like), polyamide 11, polyethylene, starch (e.g., cornstarch), or cellulose (e.g., cellulose esters, e.g., cellulose acetate, nitrocellulose)).

In some embodiments, the present invention provides a biocontrol composition of the invention in an applicator useful for delivering to a plant, plant part or soil, the composition as a liquid or a solid (e.g., powders, granules, colonized seed, and the like). Any type of equipment known in the art for applying liquid or solid compositions of this invention may be used with this invention including, but not limited to, a sprayer, an aerial applicator (e.g., aircraft), and/or a spreader (e.g., tractor) and the like.

In some embodiments, the present invention provides a method of making a biocontrol composition for reducing aflatoxin production in a field population of one or more heterothallic filamentous fungi, the method comprising: selecting for the biocontrol composition at least a first strain of a heterothallic filamentous fungus having a lineage of low mycotoxin production and a MAT1-1 mating type; selecting for the biocontrol composition at least a second strain of a heterothallic filamentous fungus having a lineage of low mycotoxin production and a MAT1-2 mating type; and combining the first and second strains into the biocontrol composition.

In some embodiments, the first strain and/or the second strain may be selected for having a mycotoxin gene cluster.

In some embodiments, the first strain and/or the second strain may be selected for having at least one mutation in a mycotoxin gene cluster (e.g., that results in a reduction in mycotoxin production). In some embodiments, the mutation may be a deletion or it may be one or more single nucleotide polymorphism(s) (e.g., 1, 2, 3, 4, 5, 6, 7, 8, or more polymorphisms).

In some embodiments, the first strain and/or the second strain may be selected for lacking a mycotoxin gene cluster. See e.g., fumonisin gene cluster (Niu et al. *BMC Microbiol.* 15:90 (11 pages) (2015)); trichothecene gene cluster (Ward et al. *Proc Natl Acad Sci USA.* 99(14): 9278-9283 (2002); and ochratoxin A gene cluster (Geisen et al. *Mycotoxin Res.* 22(2):134-141 (2006)).

In some embodiments, the present invention provides a method of making a biocontrol composition for reducing aflatoxin production in a field population of *Aspergillus flavus*, the method comprising selecting for the biocontrol composition at least a first *A. flavus* strain that is a low aflatoxin producing strain having a lineage of IB and a MAT1-1 mating type; selecting for the biocontrol composition at least a second *A. flavus* strain that is a low aflatoxin producing strain having a lineage of IB and a MAT1-2 mating type and combining the first and second strains into the biocontrol composition.

Lineages IB and IC are evolutionary lineages of *A. flavus*. Lineage IB includes strains with partial or complete deletions of the aflatoxin cluster or full-cluster strains with many fixed polymorphisms when compared to lineage IC, which includes aflatoxigenic isolates and those that are non-aflatoxigenic due to loss-of-function mutations (Moore et al. *PLOS Pathogens* 9(8):e1003574 (2013)). Lineages IB and IC are phylogenetically distinct based on DNA sequence variation across the entire aflatoxin cluster (Moore et al. *Molecular Ecology* 18: 4870-4887 (2009)) and genome-wide using oligonucleotide-based array comparative genome hybridization (Moore et al. *PLOS Pathogens* 9(8): e1003574 (2013)).

In some embodiments, the first strain and/or the second strain may be further selected for having an aflatoxin gene cluster. In some embodiments, the first strain and/or the second strain may be selected for having at least one mutation in the aflatoxin gene cluster (that results in a reduction in aflatoxin production). In some embodiments, the at least one mutation may be a deletion or a single nucleotide polymorphism. In some embodiments, the first strain and/or the second strain may be further selected for lacking a mycotoxin gene cluster. Mutations in the aflatoxin gene cluster are known in the art (Moore et al. *Mol. Ecol.* 18: 4870-4887 (2009)). The specific loss-of-function mutation in strain AF36 is described in Ehrlich & Cotty, *Appl. Microbiol. Biotechnol.* 65(4):473-478 (2004). These can be identified using laboratory crosses as described in Olarte et al. (*Mol. Ecol.* 21(6):1453-1476 (2012)). By crossing AF− and AF+ parental strains, any crossover in the cluster that restores AF in a progeny strain can be useful in identifying causal mutations in the AF− phenotype.

Any method for selecting a strain of a heterothallic filamentous fungus may be used with this invention. For example, the strain may be initially isolated from soil by single spore isolation using established dilution-plating techniques that are well known in the art. Once the strain is isolated, amplification and sequencing of target loci may be carried out, for example, to determine lineage and mating type.

In some embodiments, non-aflatoxigenic strains of opposite mating type may be selected that belong to lineage IB or which are natural recombinants between lineages IB and IC that are predominantly IB in their genetic background. In some embodiments, strains that are missing the entire aflatoxin gene cluster or have partial deletions of the cluster may be selected over strains having a full gene cluster.

In some embodiments, a strain of *A. flavus* may be selected having high sclerotia production (e.g., a recombinant between lineage IB and lineage IC having low toxin production with high production of sclerotia; female), wherein high sclerotia production is relative to a strain that is a recombinant between lineage IB and lineage IC having high toxin production or relative to a strain that is a lineage IC strain having high toxin production. In some embodiments, a strain of *A. flavus* may be selected having high conidia production (e.g., a IB lineage strain having low toxin production with a high production of conidia; male), wherein high conidia production is relative to a strain that is a lineage IC strain and has high toxin production. In some embodiments, a biocontrol composition may comprise at least one strain of *A. flavus* having high sclerotia production and at least one strain of *A. flavus* having high conidia production.

In some embodiments, the present invention provides a biocontrol method for reducing mycotoxin production in a field population of one or more heterothallic filamentous fungi, the method comprising applying a biocontrol composition to a plant, a plant part and/or a soil, the biocontrol composition comprising an effective amount of propagules (e.g., colony forming units) of at least two strains of the one or more heterothallic filamentous fungi (e.g., 2, 3, 4, 5, 6, 7, 8, 9, 10 strains, and the like), wherein the at least two strains comprise a first strain and a second strain of the one or more heterothallic filamentous fungi, each strain comprising a lineage of low or no mycotoxin production, wherein the first strain further comprises a MAT1-1 mating type and the second strain further comprises a MAT1-2 mating type, wherein the amount of propagules of the at least two strains of the one or more heterothallic filamentous fungi is effective to promote mating between compatible mating partners in the field population and the at least two strains, thereby increasing the ratio of strains having the lineage of no or low mycotoxin production in the field population of the one or more heterothallic filamentous fungi and reducing mycotoxin production by the field population of the one or more heterothallic filamentous fungi. In some embodiments, the ratio of the propagules of the first strain to propagules of the second strain in the biocontrol composition is about equal (e.g., for two strains the ratio may be about 1:1 (e.g., about 0.8:1 to about 1:1.2, about 0.9:1 to about 1:1:1, and the like).

In some embodiments, the present invention provides a biocontrol method for reducing the mycotoxin production in a field population of one or more heterothallic filamentous fungi, the method comprising applying a biocontrol composition to a plant, a plant part and/or a soil, the biocontrol composition comprising an effective amount of propagules (e.g., colony forming units) of at least two strains of the one or more heterothallic filamentous fungi, wherein the at least two strains of the heterothallic filamentous fungi comprises four strains, a first strain, a second strain, a third strain and a fourth strain, each strain comprising a lineage of low or no mycotoxin production, wherein the first and second strains are from the same species and the third and fourth strains are from the same species, and the first and third strains are each from the same genus/species or a different genus/species, and the second and fourth strains are each from the same genus/species or a different genus/species, wherein the first and third strains further comprise a MAT1-1 mating type and the second and fourth strains further comprise a MAT1-2 mating type, wherein the amount of propagules of the first strain, second strain, third strain and fourth strain is effective to promote mating between compatible mating partners in the field population and the four strains, thereby increasing the ration of strains having the lineage of no or low mycotoxin production in the field population of the heterothallic filamentous fungi and reducing mycotoxin production by the field population of the heterothallic filamentous fungi. In some embodiments, the ratio of propagules of the first, second, third and fourth strains in the biocontrol composition is about equal (e.g., for four strains the ratio may be about 1:1:1:1 (e.g., about 0.8:1:0.8:1 to about 1:1.2:1:1.2 and the like).

In some embodiments, the invention provides a biocontrol method for reducing mycotoxin production in a field population of *Aspergillus flavus*, comprising applying a biocontrol composition to a plant, a plant part and/or a soil, the biocontrol composition comprising an effective amount of propagules of at least two strains of *A. flavus* (e.g., 1, 2, 3, 4, 5, 6, 7, 8, 9, 10 or more), wherein the at least two strains comprise a first strain and a second strain, each strain comprising a lineage of IB and being a low producer or a non-producer of the mycotoxin, wherein the first strain further comprises a MAT1-1 mating type and the second strain further comprises a MAT1-2 mating type, wherein the amount of propagules of the at least two strains of *A. flavus* is effective to promote mating between compatible mating partners in the field population and the two strains of *A. flavus*, thereby increasing the ratio of strains having the IB lineage in the field population of *A. flavus* and reducing mycotoxin production by the field population of *A. flavus*. In some embodiments, the ratio of propagules of the first strain to propagules of the second strain in the biocontrol composition is about equal (e.g., for two strains, the ratio may be about 1:1 (e.g., about 0.8:1 to about 1:1.2, about 0.9:1 to about 1:1:1, and the like)). In some embodiments, the mycotoxin is aflatoxin.

In some embodiments, the present invention provides a biocontrol method for reducing mycotoxin production in a field population of *Aspergillus flavus*, the method comprising applying a biocontrol composition to a plant, a plant part and/or a soil, the biocontrol composition comprising an effective amount of propagules (e.g., colony forming units) of at least two strains of *A. flavus*, wherein the at least two strains of *A. flavus* comprises four strains of *A. flavus* comprising a first strain, a second strain, a third strain and a fourth strain, each strain comprising a lineage of IB and having a low production of the mycotoxin or no production of aflatoxin, wherein the first and third strains further comprise a MAT1-1 mating type, and the second and fourth strains further comprise a MAT1-2 mating type, wherein the amount of propagules of the first strain, second strain, third strain and fourth strain is effective to promote mating between compatible mating partners in the field population and the four strains, thereby increasing the ratio of strains having the IB lineage in the field population of *A. flavus* and reducing mycotoxin production by the field population of *A. flavus*. In some embodiments, the ratio of propagules of the first, second, third and fourth strains in the biocontrol composition is about equal (e.g., for four strains the ratio may be about 1:1:1:1 (e.g., about 0.8:1:0.8:1 to about 1:1.2:1:1.2 and the like)). In some embodiments, the mycotoxin is aflatoxin.

In some embodiments, the present invention provides a method of sustainably reducing mycotoxin production in a field population of one or more heterothallic filamentous fungi (e.g., 1, 2, 3, 4, 5, 6, 7, 8, 9, 10, and the like), comprising shifting the lineage of the field population of the one or more heterothallic filamentous fungi to low mycotoxin production or no mycotoxin production, the method comprising applying a biocontrol composition to a plant, a plant part and/or a soil, the biocontrol composition comprising an effective amount of propagules of at least two strains (e.g., 1, 2, 3, 4, 5, 6, 7, 8, 9, 10 or more) of the one or more heterothallic filamentous fungi, wherein the at least two strains comprise a first strain and a second strain, each strain comprising a lineage of being a low producer or a non-producer of at least one mycotoxin, wherein the first strain further comprises a MAT1-1 mating type and the second strain further comprises a MAT1-2 mating type, wherein the amount of propagules of the at least two strains of the one or more heterothallic filamentous fungi is effective to promote mating between compatible mating partners in the field population and the at least two strains, thereby shifting the lineage of the field population of the one or more heterothallic filamentous fungi to low mycotoxin production or no mycotoxin production and producing a sustained reduction in mycotoxin production in a field population of the one or more heterothallic filamentous fungi. In some embodiments, the ratio of propagules of the first strain to propagules of the second strain in the biocontrol composition is about equal (e.g., for two strains the ratio may be about 1:1 (e.g., about 0.8:1 to about 1:1.2, about 0.9:1 to about 1:1:1, and the like)).

In some embodiments, the present invention provides a method of sustainably reducing mycotoxin production in a field population of one or more heterothallic filamentous fungi (e.g., 1, 2, 3, 4, 5, 6, 7, 8, 9, 10, and the like), comprising shifting the lineage of the field population of the one or more heterothallic filamentous fungi to low mycotoxin production or no mycotoxin production, the method comprising applying a biocontrol composition to a plant, a plant part and/or a soil, the biocontrol composition comprising an effective amount of propagules (e.g., colony forming units) of at least two strains of the one or more heterothallic filamentous fungi, wherein the at least two strains of the one or more heterothallic filamentous fungi comprises four strains, a first strain, a second strain, a third strain and a fourth strain, each strain comprising a lineage of low or no mycotoxin production, wherein the first and second strains are from the same species and the third and fourth strains are from the same species, and the first and third strains are each from the same genus/species or a different genus/species, and the second and fourth strains are each from the same genus/species or a different genus/species, wherein the first and third strains further comprise a MAT1-1 mating type and the second and fourth strains further comprise a MAT1-2 mating type, wherein the amount of propagules of the first strain, second strain, third strain and fourth strain is effective to promote mating between compatible mating partners in the field population and the four strains, thereby shifting the lineage of the field population of the at one or more heterothallic filamentous fungi to low mycotoxin production or no mycotoxin production and producing a sustained reduction in mycotoxin production in a field population of the one or more heterothallic filamentous fungi. In some embodiments, the ratio of propagules of the first, second, third and fourth strains in the biocontrol composition is about equal (e.g., for four strains the ratio may be about 1:1:1:1 (e.g., about 0.8:1:0.8:1 to about 1:1.2:1:1.2 and the like)).

In some embodiments, the present invention provides a method of sustainably reducing aflatoxin production in a field population of *Aspergillus flavus*, comprising shifting the lineage of the field population of *A. flavus* to low aflatoxin production or no aflatoxin production, the method comprising applying a biocontrol composition to a plant, a plant part and/or a soil, the biocontrol composition comprising an effective amount of propagules of at least two strains (e.g., 1, 2, 3, 4, 5, 6, 7, 8, 9, 10 or more) of *A. flavus*, wherein the at least two strains comprise a first strain and a second strain, each strain comprising a lineage of IB and being a low producer or a non-producer of aflatoxin, wherein the first strain further comprises a MAT1-1 mating type and the second strain further comprises a MAT1-2 mating type, wherein the amount of propagules of the at least two strains of *A. flavus* is effective to promote mating between compatible mating partners in the field population and the at least two strains, thereby shifting the lineage of the field population of *A. flavus* to low aflatoxin production or no aflatoxin production and producing a sustained reduction in aflatoxin production in the field population of *A. flavus*. In some embodiments, the ratio of propagules of the first strain to propagules of the second strain in the biocontrol composition is about equal (e.g., for two strains the ratio may be about 1:1 (e.g., about 0.8:1 to about 1:1.2, about 0.9:1 to about 1:1:1, and the like)).

In some embodiments, the present invention provides a method of sustainably reducing aflatoxin production in a field population of *Aspergillus flavus*, comprising shifting the lineage of the field population of *A. flavus* to low aflatoxin production or no aflatoxin production, the method comprising applying a biocontrol composition to a plant, a plant part and/or a soil, the biocontrol composition comprising an effective amount of propagules (e.g., colony forming units) of at least two strains of *A. flavus*, wherein the at least two strains of *A. flavus* comprises four strains of *A. flavus* comprising a first strain, a second strain, a third strain and a fourth strain, each strain comprising a lineage of TB and having a low production of aflatoxin or no production of aflatoxin, wherein the first and third strains further comprise a MAT1-1 mating type and the second and fourth strains further comprise a MAT1-2 mating type, d wherein the amount of propagules of the first strain, second strain, third strain and fourth strain is effective to promote mating between compatible mating partners in the field population and the four strains, thereby shifting the lineage of the field population of *A. flavus* to low aflatoxin production or no aflaotoxin production and producing a sustained reduction in aflatoxin production in a field population of *A. flavus*. In some embodiments, the ratio of propagules of the first, second, third and fourth strains in the biocontrol composition is about equal (e.g., for four strains the ratio may be about 1:1:1:1 (e.g., about 0.8:1:0.8:1 to about 1:1.2:1:1.2 and the like)).

As used herein, "sustainably reducing mycotoxin production" (e.g., aflatoxin production) means reducing mycotoxin production for at least 18 mo to at least 5 years or 18 mo to about 5 to about 10 years. In some embodiments, the reduction in mycotoxin production may be sustained over a period of time from at least about 18 months, at least about 2 years, at least about 3 years, at least about 4 years, at least about 5 years; at least about 6 years; at least about 7 years; at least about 8 years; at least about 9 years; at least about 10 years; or from at least about 2 years to about 5 years, from at least about 2 years to about 6 years, from at least about 2 years to about 7 years, from at least about 2 years to about 8 years, from at least about 2 years to about 9 years, from at least about 2 years to about 10 years (e.g., about 2, 3, 4, 5, 6, 7, 8, 9, 10 years).

In some embodiments, application of the compositions of the invention to a plant, plant part, or soil in a particular area may be repeated about every 2 years, about every 3 years, about every 4 years, about every 5 years, about every 6 years, about every 7 years, about every 8 years, about every 9 years, about every 10 years, and the like.

A heterothallic filamentous fungus useful with this invention may be any heterothallic filamentous fungus that produces at least one mycotoxin. In some embodiments, the one or more heterothallic filamentous fungi of a composition or method of the invention may be from the genus *Fusarium* and/or the genus *Aspergillus*, or any combination thereof. Thus, in some embodiments, when a composition or method of the invention comprises more than two strains (e.g., a first strain, a second strain, a third strain, and a fourth strain), at least two strains may be from, for example, the genus *Aspergillus* and at least two other strains may be from, for example, the genus *Fusarium*, thereby producing a biocontrol composition useful for reducing toxin production by more than one species/genera of heterothallic filamentous fungi. Thus, as an example, a composition of the invention may be useful for reducing mycotoxin production in maize ear rot where both *Aspergillus* spp. (e.g., *A. flavus*) and *Fusarium* spp. (e.g., *F. verticillioides*) are found.

A heterothallic filamentous fungus useful with this invention may be any fungal species having a heterothallic mating type organization and produces at least one mycotoxin. In some embodiments, even in fungal species not previously identified as heterothallic, sexual reproduction may be induced once the mating types of different strains and growing conditions necessary for sexual reproduction are identified (see, e.g., Bohm et al. *Proc. Natl. Acad. Sci. USA.* 110(4):1476-1481 (2013)).

In some embodiments, a heterothallic filamentous fungus that may be useful with this invention may be, for example, from the genus *Penicillium* (alone or in combination with one or more heterothallic filamentous fungi from the genus *Fusarium* and/or the genus *Aspergillus*).

In some embodiments, the one or more heterothallic filamentous fungi may be from the genus *Fusarium* and the toxic metabolite or mycotoxin may include, but is not limited to, fumonisin, zearalenone, trichothecene, deoxynivalenol, acetyldeoxynivalenol, nivalenol and/or deoxynivalenol. In some embodiments, the one or more heterothallic filamentous fungi may be from the genus *Aspergillus* and the mycotoxin may include, but is not limited to, aflatoxin and/or ochratoxin A. In some embodiments, the one or more heterothallic filamentous fungi may be from the genus *Penicillium* and the mycotoxin may include, but is not limited to, ochratoxin A.

In some embodiments, the one or more heterothallic filamentous fungi may be *Penicillium citrinum*, *Penicillium hirsutum*, *Penicillium verrucosum*, and/or *Penicillium citreoviride*, or any combination thereof.

In some embodiments, the one or more heterothallic filamentous fungi may be *Aspergillus flavus*, *Aspergillus parasiticus*, *Aspergillus parasiticus*, *Aspergillus nomius*, *Aspergillus flavus* L, *Aspergillus flavus* S, *Aspergillus pseudotamarii*, *Aspergillus pseudocaelatus*, *Aspergillus korhogoensis*, *Aspergillus minisclerotigenes*, *Aspergillus ochraceoroseus*, *Aspergillus rambelli*, *Aspergillus arachidicola*, *Aspergillus novoparasiticus*, *Aspergillus parvisclerotigenus*, and/or *Aspergillus ochraceus*, or any combination thereof.

In some embodiments, the one or more heterothallic filamentous fungi may be *Fusarium moniliforme*, *Fusarium equiseti*, *Fusarium oxysporum*, *Fusarium culmorum*, *Fusarium avenaceum*, *Fusarium roseum*, *Fusarium solani*, and/or *Fusarium nivale*, or any combination thereof.

In some embodiments, the one or more heterothallic filamentous fungi may be *A. flavus* strains that are native to Nigeria. In some embodiments, the *A. flavus* strains may be Og0222, La3279, Og0104, La3304, La3305, and/or Ka16127. In some embodiments, the one or more heterothallic filamentous fungi are not *A. flavus* strains Og0222, La3279, Og0104, La3304, La3305, and/or Ka16127. In some embodiments, the one or more heterothallic filamentous fungi are not a combination of any two, three or all four of the *A. flavus* strains Og0222, La3279, Og0104, La3304, La3305, and/or Ka16127.

In some embodiments, the one or more heterothallic filamentous fungi may be an *A. flavus* strains that are native to Italy. An exemplary *A. flavus* strain from Italy may be A2085 (MAT1-1). In some embodiments, the one or more heterothallic filamentous fungi are not *A. flavus* strain A2085.

In some embodiments, the one or more heterothallic filamentous fungi may be *A. flavus* strains that are native to Argentina. Exemplary *A. flavus* strains from Argentina may be AR27, AR100G and/or AFCHG2 (MAT1-1). In some embodiments, the one or more heterothallic filamentous fungi are not a combination of any two or all three of the *A. flavus* strains of AR27, AR100G and/or AFCHG2. In some embodiments, the one or more heterothallic filamentous fungi are not *A. flavus* strains AR27, AR100G and/or AFCHG2.

In some embodiments, the one or more heterothallic filamentous fungi may be *A. flavus* strains that are native to Thailand. Exemplary *A. flavus* strains from Thailand may be FRR 6023, FRR 6024, FRR 6025 and/or FRR 6026. In some embodiments, the one or more heterothallic filamentous fungi are not a combination of any two, three or all four of the *A. flavus* strains of FRR 6023, FRR 6024, FRR 6025 and/or FRR 6026. In some embodiments, the one or more heterothallic filamentous fungi are not *A. flavus* strains FRR 6023, FRR 6024, FRR 6025 and/or FRR 6026.

In some embodiments, the one or more heterothallic filamentous fungi may be *A. flavus* strains that are native to China. An exemplary *A. flavus* strain from China may be GD-3. In some embodiments, the one or more heterothallic filamentous fungi are not *A. flavus* strain GD-3.

In some embodiments, the one or more heterothallic filamentous fungi may be *A. flavus* strains that are native to Africa, e.g., Aflasafe GH02, Aflasafe SN01, Alfasafe BF01, and/or Aflasafe KE01. In some embodiments, the one or more heterothallic filamentous fungi are not a combination of any two or all three of the *A. flavus* strains of Aflasafe GH02, Aflasafe SN01, Alfasafe BF01, and/or Aflasafe KE01. In some embodiments, the one or more heterothallic filamentous fungi are not *A. flavus* strains Aflasafe GE102, Aflasafe SN01, Alfasafe BF01, and/or Aflasafe KE01.

In some embodiments, the one or more heterothallic filamentous fungi may be *A. flavus* non-aflatoxigenic strains NRRL 18543 (e.g., AF36®) and/or NRRL 21882 (AFLA-GUARD®). In some embodiments, the one or more heterothallic filamentous fungi are not *A. flavus* strain NRRL 18543 and/or *A. flavus* strain NRRL 21882.

In some embodiments, the one or more heterothallic filamentous fungi may be *A. flavus* non-aflatoxigenic strains K49 (NRRL 30797). In some embodiments, the one or more heterothallic filamentous fungi are not *A. flavus* strain NRRL 30797.

In some embodiments, mycotoxin production may be reduced using homothallic, low toxigenic fungi that can outcross with heterothallic fungal strains or other homothallic fungal strain. Thus, in some embodiments, the present invention provides a biocontrol composition comprising an effective amount of propagules (e.g., colony forming units, cfu) of one or more strains of one or more homothallic filamentous fungi (e.g., 1, 2, 3, 4, 5, 6, 7, 8, 9, 10 strains and the like), wherein the homothallic filamentous fungal strain comprises a lineage of low or no mycotoxin production (atoxigenic) and comprises a MAT1-1 mating type and a MAT1-2 mating type. In some embodiments, a homothallic fungus may be a strain of *Aspergillus, Penicillium* and/or *Fusarium*. In some embodiments, a homothallic fungus may be *Fusarium graminearum*. In some embodiments, a homothallic fungus may be A *Aspergillus flavus.*

In some embodiments, a biocontrol composition may comprise both homothallic and heterothallic fungi. Thus, for example, it may be advantageous to provide an atoxigenic or low toxigenic *A. flavus* strain that is homothallic in a composition comprising the heterothallic strains as described herein. In some embodiments, a low toxigenic/atoxigenic *A. flavus* strain that is homothallic may have highly fertility, which would be advantageous in assisting in the spreading the low toxigenicity/atoxigenicity and homothallism to subsequent generations.

As used herein, "atoxigenic" refers to a fungal strain having zero/no mycotoxin production. The mycotoxin may not be synthesized because, for example, the strain maybe missing the entire biosynthetic pathway or may have a loss of function mutation.

As used herein, "low toxin production" or "low mycotoxin production" by a strain in the composition means a strain of a particular evolutionary lineage having a low mycotoxin production. All strains within the same lineage should be low mycotoxin producers. In some embodiments, low mycotoxin production means having a mycotoxin production of less than 1% of the highest concentration of toxin production in a population sample Mycotoxin production by a strain may be measured in a pure fungal culture extract using methods known in the art.

In some embodiments, the mycotoxin is aflatoxin and "low aflatoxin production" means aflatoxin production of less than about 10 μg/mL aflatoxin as measured in a fungal culture extract (e.g., a pure culture of the strain grown on, for example, a yeast extract sucrose (YES) broth in the light incubator at about 2° C. 5 to about 35° C. for about 7 days). Thus, in some embodiments, low aflatoxin production may be less than about 10 μg/ml (e.g, about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9 μg/mL aflatoxin, or less, or any value or range therein).

In some embodiments, determination of low toxin production for an isolate may be based on at least three replicates, wherein the toxin production in at least two out of three for the isolate is lower than about 10 μg/ml.

In some embodiments, a propagule of a heterothallic filamentous fungus may be conidia, sclerotia, hyphae, and/or fragmented hyphae, or any combination thereof. In some embodiments, the propagule of a heterothallic filamentous fungus may be provided in a colonized media, e.g., a colonized seed (e.g., heat killed seed) or a colonized bioplastic granule/pellet/particle.

In some embodiments, an effective amount of propagules of each of the at least two strains (e.g., a first, a second, a third, a fourth strain, and the like) of a heterothallic filamentous fungus in a biocontrol composition of the present invention may be about $1\times10^4$ cfu per ml to about $5\times10^{10}$ cfu per ml or more (e.g., $10^{11}$, $10^{12}$, $10^{13}$, $10^{14}$) (or about $1\times10^5$ cfu per gram to about $5\times10^{10}$ cfu per gram) of the biocontrol composition (e.g., about $1\times10^4$ to about $5\times10^{10}$, about $1\times10^4$ to about $1\times10^9$, about $1\times10^4$ to about $1\times10^8$, about $1\times10^5$ to about $5\times10^{10}$, about $1\times10^5$ to about $1\times10^9$, about $1\times10^5$ to about $1\times10^8$, about $1\times10^6$ to about $5\times10^{10}$, about $1\times10^6$ to about $1\times10^9$, about $1\times10^6$ to about $1\times10^8$ cfu per ml (or cfu per gram) of the composition, or any range or value therein. Thus, in some embodiments, an effective amount of propagules of at least two strains of a heterothallic filamentous fungus in a biocontrol composition of the present invention may be present in an amount of about 11,000, 12,000, 13,000, 14,000, 15,000, 20,000, 25,000, 30,000, 35,000, 40,000, 45,000, 50,000, 75,000, 100,000, 150,000, 200,000, 250,000, 300,000, 500,000, 750,000, $1\times10^6$, $5\times10^6$, $7.5\times10^6$, $1\times10^7$, $5\times10^7$, $7.5\times10^7$, $1\times10^8$, $1.5\times10^8$, $5\times10^8$, $7.5\times10^8$, $1\times10^9$, $5\times10^9$, $7.5\times10^9$, $1\times10^{10}$, $5\times10^{10}$ cfu/ml (or cfu/gram) of the composition, or any range or value therein.

In some embodiments, an effective amount of each of the at least two strains of a heterothallic filamentous fungus in a biocontrol composition of the present invention may be about $1\times10^5$ propagules per ml to about $5\times10^{10}$ propagules per ml or more or any range or value therein (e.g., about 10,000, 11,000, 12,000, 13,000, 14,000, 15,000, 20,000, 25,000, 30,000, 35,000, 40,000, 45,000, 50,000, 75,000, 100,000, 150,000, 200,000, 250,000, 300,000, 500,000, 750,000, $1\times10^6$, $5\times10^6$, $7.5\times10^6$, $1\times10^7$, $5\times10^7$, $7.5\times10^7$, $1\times10^8$, $1.5\times10^8$, $5\times10^8$, $7.5\times10^8$, $1\times10^9$, $5\times10^9$, $7.5\times10^9$, $1\times10^{10}$, $5\times10^{10}$ propagules/ml (or propagules/gram) of the composition, or any range or value therein).

In some embodiments, an effective amount of propagules of each of the at least two strains is several orders of magnitude greater than the amount of propagules found in nature (e.g., about 500-8500 cfu/g for *A. flavus* (Horn et al. *PLoS One;* 11(1):e0146169 (2016)).

In some embodiments, a composition of the invention may be applied to a plant, plant part, or soil at a rate of about $1\times10^5$ to about $5\times10$ 10 cfu (or propagules) of each strain per acre (e.g., about $1\times10^5$, $1\times10^6$, $5\times10^6$, $7.5\times10^6$, $1\times10^7$, $5\times10^7$, $7.5\times10^7$, $1\times10^8$, $1.5\times10^8$, $5\times10^8$, $7.5\times10^8$, $1\times10^9$, $5\times10^9$, $7.5\times10^9$, $1\times10^{10}$, $5\times10^{10}$ cfu of each strain per acre), and any range or value therein.

In some embodiments, the heterothallic filamentous fungus may be isolated from nature (e.g., from the same region to be treated with the biocontrol composition, e.g., a native strain) and incorporated into a biocontrol composition of the invention at a non-natural concentration of about $1\times10^4$ cfu per ml to about $5\times10^{10}$ cfu per ml of the biocontrol composition. In some embodiments, the heterothallic filamentous fungus may be isolated from nature and then modified, for example, to decrease the amount of toxin production. In some embodiments, the strain may a laboratory strain or strain already comprises at least one modification relative to a strain found in nature. Such modifications may carried out using culturing methods, by mutagenesis, by genetic modification, or by gene editing, or any combination thereof. Any of these methods may be used to modify, for example, a gene involved, directly or indirectly, in toxin production (e.g., a gene associated with toxin production).

In some embodiments, the methods of the invention further comprise selecting a first strain and a second strain (or a third and a fourth strain, and the like) having high fertility when crossed, wherein the first strain is MAT1-1 mating type and the propagules are sclerotia and the second strain is MAT1-2 mating type and the propagules are conidia, or wherein the first strain is MAT1-1 mating type and the propagules are conidia and the second strain is MAT1-2 mating type and the propagules are sclerotia. In some embodiments, selection of a highly fertile cross is pre-determined in vitro. "High fertility" as used herein refers to highly fertile cross. A "highly fertile cross" refers to a successful mating interaction where at least 90% of sclerotia produced are fertile and contain one or more fertile (i.e. ascospore-bearing) ascocarps.

Mycotoxin production in field populations of heterothallic filamentous fungi may be reduced using the methods and compositions of the invention. Thus, application of a composition of the invention as described herein to plants, plant parts and/or soil may reduce mycotoxin production in field populations of heterothallic filamentous fungi associated with the plants, plant parts, and/or soil to which the composition is applied as compared to field populations of heterothallic filamentous fungi associated with plants, plant parts, and/or soil not having received application of a composition of the invention.

In some embodiments, application of the compositions of the present invention to plants, plant parts and/or soil may increase the ratio of strains of heterothallic filamentous fungi in a field population having a low toxin producing lineage versus a high toxin producing lineage as compared to a control (e.g., the ratio of strains having low toxin producing lineage versus high toxin producing lineage in a field population of the heterothallic filamentous fungi that is associated with plants, plant parts or soil to which a composition of the invention has not been applied; a field population of heterothallic filamentous fungi not contacted by the biocontrol compositions of the invention).

In some embodiments, an increase in the ratio of strains having a low toxin producing lineage versus high toxin producing lineage in a field population of heterothallic filamentous fungi may be measured about 1 year or more (e.g., about 1, 2, 3, 4, 5, years or more) after the application of a composition of the present invention. In some embodiments, the increase in ratio of strains having a low toxin producing lineage versus high toxin producing lineage in a field population of heterothallic filamentous fungi may be measured from about 1 year to about 10 years or more (e.g., about 1, 2, 3 years or more; e.g., about 12, 13, 14, 15, 16, 17, 18, 19, 20, 21, 22, 23, 24, 25, 26, 27, 28, 29, 30, 31, 32, 33, 34, 35, 36 months or more, to about 4, 5, 6, 7, 8, 9, 10 years or more) after the application of a composition of the present invention. In some embodiments, an increase in the ratio of IB:IC may be greater than 2 (e.g., 2, 3, 4, 5 or more and any value or range therein).

Thus, in some embodiments, the compositions and methods of the present invention may be used to increase the ratio of strains of *A. flavus* having an IB lineage versus an IC lineage in a field population of *A. flavus*. In some embodiments, the increase in the ratio of strains having an IB lineage versus an IC lineage may be measured in a field population about 1 year to about 10 years or more (e.g., about 1, 2, 3, 4, 5, 6, 7, 8, 9, 10, years or more) (e.g., about 1 to about 3 years, about 1 to about 4 years, about 1 to about 5 years, about 1 to about 6 years, about 1 to about 7 years, about 1 to about 8 years, about 1 to about 9 years, about 1 to about 10 years or more) after application of a biocontrol composition of the present invention to a plant, plant part or soil associated with the field population as compared to the ratio of the field population of *A. flavus* not associated with a plant, plant part, and/or soil treated with a biocontrol composition of the present invention. Thus, in some embodiments, the ratio of *A. flavus* strains having an IB lineage versus an IC lineage in a field population may be increased for 1 to 10 years or more (e.g., about 1, 2, 3, 4, 5, 6, 7, 8, 9, 10 years or more) after application of a biocontrol composition of the present invention to a plant, plant part or soil associated with the field population as compared to the ratio of the field population of *A. flavus* not associated with a plant, plant part, and/or soil treated with a biocontrol composition of the present invention.

In some embodiments, the methods and compositions of the invention may be used to reduce aflatoxin production in a field population of heterothallic filamentous fungi (e.g., *A. flavus, A. parasiticus*) to less than 10 ppb, about 1 ppb to about 30 ppb, about 10 ppb to about 30 ppb, or about 10 ppb to about 100 ppb. Thus, in some embodiments, aflatoxin production may be reduced to about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 ppb as measured in a plant sample (e.g., corn, peanut, and the like; as measured using, for example, a Vicam test kit or Quick-Tox®).

Methods for measuring amounts of mycotoxins are known in the art and include but are not limited to chromatography (e.g., thin-layer chromatography (TLC), high-performance liquid chromatography (HPLC), and/or gas chromatography (GC)), fluorescence spectrophotometry, infrared spectroscopy (IR), immunochemical techniques (e.g., radioimmunoassay (RIA), enzyme-linked immunosorbent assay (ELISA), immunoaffinity column assay (ICA), lateral flow devices (e.g., immunodipsticks), and/or immunosensors). Mycotoxin amounts may be measured in plants, plant parts, fungal culture(s), and e.g., in. corn, wheat, barley, oats, sorghum, whole peanut, peanut hull and peanut seed. The plants and plant parts are ground, and extracted to solubilize the aflatoxin, which amounts can then be measured using the methods known in the art and described herein.

In some embodiments, strains of a heterothallic filamentous fungus may be selected for the compositions of the invention. Thus, in some embodiments, strains of a heterothallic filamentous fungus may be selected for evolutionary lineage (e.g., low toxin production; e.g., lineage IB for aflatoxin production), mating type and/or for the presence or absence of a gene or gene cluster encoding mycotoxin production or associated with mycotoxin production and/or mutations in a gene and/or a gene cluster encoding mycotoxin production or associated with mycotoxin production. In some embodiments, strains of a heterothallic filamentous fungus may be selected based on the presence of mutations in a gene or a gene cluster encoding mycotoxin production or in a gene associated with mycotoxin production. In some embodiments, strains of a heterothallic fungus may be selected for mating type (e.g., MAT1-1 and MAT1-2). Previously identified target loci and published oligonucleotide primer sequences may be used to make such selections.

A gene "associated with mycotoxin production" may be a gene that does not directly encode for mycotoxin production but is involved in regulation of production or any other process affecting the production of the mycotoxin.

For example, the location of the genes associated with mating type, aflatoxin production and evolutionary lineage (IB and IC) in *A. flavus* are known (see, Olarte et al. *Mol. Ecol.* 21(6):1453-1476 (2012) and Moore et al. *PLOS Pathogens* 9(8):e1003574 (2013)). Thus, *A. flavus* evolutionary lineages (IB and IC) and mating types (MAT1-1 and MAT1-2) can be determined using known or later identified target loci and published oligonucleotide primer sequences. Specifically, lineages can be distinguished based on nucleotide sequence polymorphisms in the aflatoxin gene cluster regions: aflM and aflW, the adjacent mfs region, and two non-cluster genes: tryptophan synthase (trpC) and acetamidase (amdS). Mating types can be determined using a previously published multiplex PCR test. The same determinations and selections may be carried out similarly for other heterothallic filamentous fungi.

Accordingly, in some embodiments, a heterothallic filamentous fungal strain useful with this invention may comprise a mycotoxin gene cluster (e.g., an *A. flavus* strain may comprise the entire aflatoxin gene cluster). In some embodiments, a strain may lack a mycotoxin gene cluster (e.g., an *A. flavus* strain may lack the entire aflatoxin gene cluster).

In some embodiments, when present, a mycotoxin gene cluster may comprise at least one mutation (e.g., multiple mutations, e.g., 2, 3, 4, 5, 6, 7, 8, 9, 10, 11, 12, 13, 14, 15, or more mutations; or 15 or fewer mutations (e.g., 14, 13, 12, 11, 10, 9, 8, 7, 6, 5, 4, 3, or fewer mutations) (e.g., an *A. flavus* strain may comprise an aflatoxin gene cluster having at least one mutation, preferably two or more mutations in the aflatoxin gene cluster) e.g., 10 or less mutations (e.g., 9, 8, 7, 6, 5, 4, 3, or less mutations in the aflatoxin gene cluster)). In some embodiments, the at least one mutation may result in reduced mycotoxin production as compared to a heterothallic filamentous fungus comprising a mycotoxin gene cluster not having the at least one mutation. In some embodiments, the at least one mutation in the mycotoxin gene cluster may be a deletion and/or the mutation may be a polymorphism in a gene or intergenic region. In some embodiments, the polymorphism may be more than one polymorphism and may be present in a gene or in an intergenic region.

In *Aspergillus flavus*, the mating type genes, MAT1-1 and MAT1-2, are located on chromosome 6 (Olarte et al. *Mol. Ecol.* 21(6):1453-1476 (2012)). In some embodiments, primer sequences (5'-3') useful for determining mating type for *A. flavus* strains include, but are not limited to:

| MAT1-1 | |
|---|---|
| M1F:<br>ATTGCCCATTTGGCCTTGAA | (SEQ ID NO: 1) |
| M1R:<br>TTGATGACCATGCCACCAGA | (SEQ ID NO: 2) |
| MAT1-2 | |
| M2F:<br>GCATTCATCCTTTATCGTCAGC | (SEQ ID NO: 3) |
| M2R:<br>GCTTCTTTTCGGATGGCTTGCG) | (SEQ ID NO: 4) |

Evolutionary lineage or clonal lineage may be determined using nuclear genes including, but not limited to, tryptophan synthase (trpC) and acetamidase (amdS), which are located on chromosomes 4 and 6, respectively, in *A. flavus*. In some embodiments, primer sequences (5'-3') useful for determining evolutionary lineage (e.g., IB, IC) (see, e.g., Geiser et al. *Proc. Natl. Acad. Sci.* 95:388-393 (1998)) for *A. flavus* strains include, but are not limited to:

| amdS | |
|---|---|
| amdS1:<br>CCATCGGTATAGGAACTGA | (SEQ ID NO: 5) |
| amdS2:<br>AGGGTGCCACGGTATGTC | (SEQ ID NO: 6) |
| trpC | |
| trpC1:<br>GACGGGAAATAGGCTTCC | (SEQ ID NO: 7) |
| trpC3:<br>CGCCTTGGTGGGATGGTG | (SEQ ID NO: 8) |

The genes associated with mycotoxin production are known for many heterothallic filamentous fungal species and may be used to determine the presence or absence of the gene(s) or gene clusters or to determine the presence or absence of mutations in a gene or genes associated (directly or indirectly) with mycotoxin production. Thus, for example, the aflatoxin cluster genes are known (see, GenBank Accession No for AY371490 (*Aspergillus parasitica* aflatoxin gene cluster); GenBank Accession No. NW_002477243.1 (*Aspergillus flavus* whole genome shotgun sequence); Yu et al. *Appl. Environ Microbiol.* 73(3): 1253-1262 (2004), Yu et al. *FEBS Lett.* 564:126-130 (2004), Olarte et al. *Mol. Ecol.* 21(6):1453-1476 (2012), and Moore et al. *PLOS Pathogens* 9(8):e1003574 (2013)). Further, deletion mutations in aflatoxin cluster genes are known (Moore et al. *PLOS Pathogens* 9(8):e1003574 (2013)).

Thus, in some embodiments, for aflatoxin cluster genes aflM and aflW, the adjacent mfs region on chromosome 3 may be used to identify the aflatoxin gene cluster (e.g., full, partial, or a missing aflatoxin gene cluster) (Moore et al. *PLOS Pathogens* 9(8):e1003574 (2013)). These genes may also be used to identify lineage IB or IC, which are the two predominant lineages found in fields in the United States. In some embodiments, primer sequences (5'-3') useful with the present invention for determining the presence/absence of the aflatoxin gene cluster and/or mutations in the genes associated with aflatoxin production include, but are not limited to:

| aflM |
|---|
| aflM-F:<br>GCTTGGCTCTCTCCTTTGAA (SEQ ID NO: 9) |
| afLN-R:<br>GCTGCTGAGGGAGTTGAAAC (SEQ ID NO: 10) |

| aflW |
|---|
| aflW-F:<br>GCACACGGTGTGGAAAGATA (SEQ ID NO: 11) |
| aflX-R:<br>GACTAGTGCACGATGTGCAAC (SEQ ID NO: 12) |

| mfs |
|---|
| XC4-F:<br>ATCGTGCAGACAGGAACAC (SEQ ID NO: 13) |
| XC4-R:<br>GGTGCCTTGGCCTATGCGCT (SEQ ID NO: 14) |

Other primers may be developed from the mycotoxin, lineage and mating type genes of a heterothallic filamentous fungus of interest using techniques known in the art. As an example, there are other lineages, in addition to IB and IC, that occur at lower frequencies, e.g., lineage IA and lineage II.

A phylogeny showing the global phylogeny of different *Aspergillus* lineages including *A. flavus* and the closely related fungus, *A. parasiticus* is provided in FIG. 3. This phylogeny is based on the loci of aflM, aflW, mfs, trpC, amdS, MAT1-1 and MAT1-2 and shows the global distribution of the different lineages for *A. flavus* and the closely related fungus, *A. parasiticus*

A plant or plant part that is useful with this invention may be any plant or part thereof that is susceptible to infection by a mycotoxin producing heterothallic filamentous fungus. In some embodiments, a plant or plant part useful with the present invention includes, but is not limited to, corn, peanut (ground nut), cotton, wheat, triticale, barley, oat, rice, sorghum, coffee, grape, and/or a tree nut (e.g., almond, Brazil nut, cashew, chestnut, filberts/hazelnut, macadamia nut, pecan, pistachio, shea nut and walnut).

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ.

In some embodiments, when the plant is corn, the biocontrol composition may be applied to the corn plant, corn plant part, or soil at tasseling or silking, and/or from growth stages V10 to R1. In some embodiments, when the plant is peanut, the biocontrol composition may be applied to the peanut plant or peanut plant part at pegging.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1

*Aspergillus flavus* is a common cause of pre-harvest and post-harvest diseases on maize in the southeastern United States. *A. flavus* produces aflatoxin and cyclopiazonic acid during the development and post-harvest storage of corn. Aflatoxins have been shown to have acute hepatotoxic and immunosuppressive properties and are strictly regulated by the Food and Drug Association in the United States (Horn, et. al 2014).

Aflatoxins were discovered after an outbreak of Turkey X disease led to the screening of turkey feed for toxic compounds (Wogan, 1996). There are four main aflatoxins: $B_1$, $B_2$, $G_1$, and $G_2$, which have slightly different chemical structures. *A. flavus* produces aflatoxin B 1 on corn; this mycotoxin is the most potent naturally occurring carcinogen known (Moore, et. al 2014). Aflatoxins produced by *A. flavus* are the second leading cause of aspergillosis in humans. Due to the risks aflatoxin pose to both human and animal health, the FDA regulates that grain contaminated by any more than 20 parts per billion (ppb) aflatoxin be destroyed (FDA 2009). Maize growers in the U.S. lose $300 million annually due to aflatoxin contamination (Wu 2007). *A. flavus* also produces cyclopiazonic acid (CPA), another mycotoxin, that has been shown to target the liver, kidneys, and gastrointestinal tract in animals (Burdock and Flamm, 2000; Horn, Moore, and Cabone, 2009) and has been linked to symptoms in Turkey X disease (Abbas, et. al, 2011).

Aflatoxins are managed by dense applications of nontoxigenic biological control strains, which outcompete native strains for nutrients and space in corn ears. Currently, there are two biological control strains registered with the Environmental Production Agency (EPA) as biological control products. AFLA-GUARD® was registered in 2004 for use on peanuts and corn. The AFLA-GUARD® strain (NRRL 21882) is missing the entire aflatoxin and CPA clusters. Another *A. flavus* strain, AF36, was registered in 2003 for use on maize and cottonseed. AF36 (NRRL 18543) has a nonsense mutation in the pksA gene, a gene early in the aflatoxin cluster that is necessary for the biosynthesis of aflatoxin, but possesses a full and functional CPA cluster.

Biological control strains are effective versus aflatoxin contamination, reducing contamination by about 70-90% (Dorner, 2004; *Pitt & Hocking,* 2006; *Dorner,* 2008; Yin et. al, 2008); however, biocontrol strategies for the reduction of aflatoxins are not fully understood and present several problems. Firstly, neither approved strain is persistent in soil, and, therefore, must be reapplied each growing season. The cost of application, $20 per acre, and the manual application method deters growers from using biocontrol strains. There is no predictive risk model for aflatoxin contamination; growers in areas with infrequent contamination may choose not to apply because of the high cost of application. Further, as noted previously, AF36 produces CPA, which is currently unregulated by the FDA but has been linked to adverse health effects in humans and animals Lastly, it is unclear how the dense application of nontoxigenic *A. flavus* strains as biocontrols affects the native populations of *A. flavus* and other common mycotoxin-producing maize pathogens, such as *Fusarium verticillioides* and *Ustilago maydis*.

Comparison of Nontoxigenic Strains as Potential Biocontrols

In this study, we examine the efficacy of various nontoxigenic *A. flavus* strains in reducing aflatoxin contamination and improving yield (IC6510, IC6511, IC6512 and IC6542). These four strains were chosen based on a previous study in North Carolina that identified these strains as native, nontoxigenic strains of *A. flavus*. AFLA-GUARD® and AF36 were applied as treatments to compare the efficacies of the native strains for improvement of yield and reduction in aflatoxin contamination. Untreated plots were used as a negative control for comparison to all of the treatments. The experiment was conducted at the Fountain Farm on the Upper Coastal Plain Research Station near Rocky Mount, NC, in 2015, in a Norfolk sandy loam. Syngenta N78S was seeded in 91.4 cm rows in April of 2015. The following treatments were applied at VT (tasseling) stage in a randomized complete block design with three replicates per treatment:

1) Untreated control,
2) Afla-Guard® (strain NRRL 21882) (MAT1-2; lineage IB; no cluster),
3) AF36 (NRRL 18543) (MAT1-2; lineage IC; full cluster),
4) IC6510 (MAT1-1; lineage IC; full cluster),
5) IC6511 (MAT1-1; lineage IC; full cluster),
6) IC6512 (MAT1-2; lineage IB; full cluster)+IC6542 (MAT1-2; lineage IB; partial cluster),
7) IC6510 (MAT1-1; lineage IC; full cluster)+IC6511 (MAT1-1; lineage IC; full cluster),
8) IC6510 (MAT1-1; lineage IC; full cluster)+IC6512 (MAT1-2; lineage IB; full cluster)

Impact on Mycotoxin Levels

Figure 1:
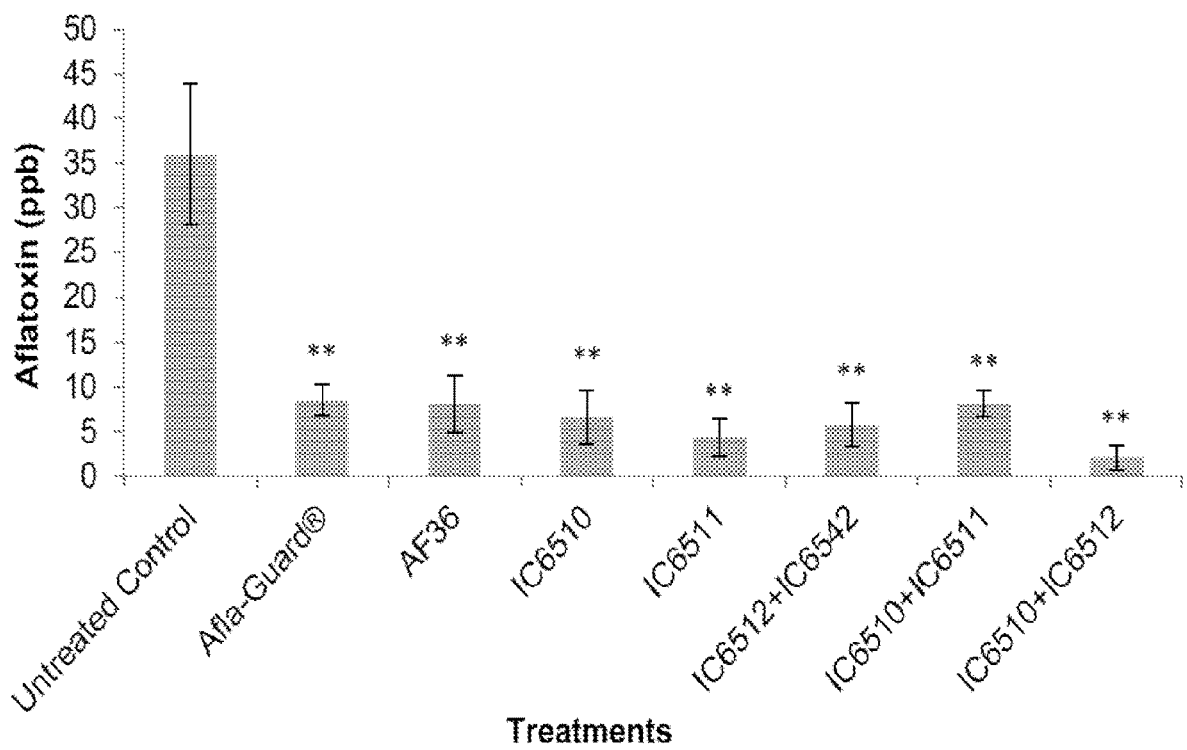
FIG. 1 shows the mean aflatoxin levels for each treatment. Aflatoxin levels are reported in parts per billion (ppb). The native biocontrol strains and the EPA-approved biological controls significantly reduced aflatoxin levels verses the untreated plots (** $P<0.1$). The error bars represent standard errors.

Maize ears were harvested in September of 2015, at black layer, using a Gleaner K2 Combine. Samples of shelled corn were taken from each plot and sent to the grain-grading laboratory for analysis of mycotoxin contamination. The various native nontoxigenic strains as well as the EPA-approved biological controls significantly reduced aflatoxin levels compared to the untreated control plots (FIG. 1). The combination of IC6510+IC6512 reduced the aflatoxin levels the most. Many of the native strains and combination of strains were more effective at reducing aflatoxin levels than Afla-Guard® or AF36.

If we examine the influence of MAT1-1 or MAT1-2 strains alone in reducing aflatoxin contamination, the formulations that included two lineage IC strains (IC6510+IC6511) or two lineage IB strains (IC6512+IC6542) were not better in reducing aflatoxin levels than the single MAT1-1 or MAT1-2 strain formulations, whereas the MAT1-1/MAT1-2 formulation (IC6510+IC6512) showed the greatest reduction in aflatoxin levels. The full impact of formulations comprising a mix of sexually compatible MAT1-1/MAT1-2 mating types is expected over several generations, as the progeny of mating events are observed in the field after one year.

Impact on Yield

Figure 2:
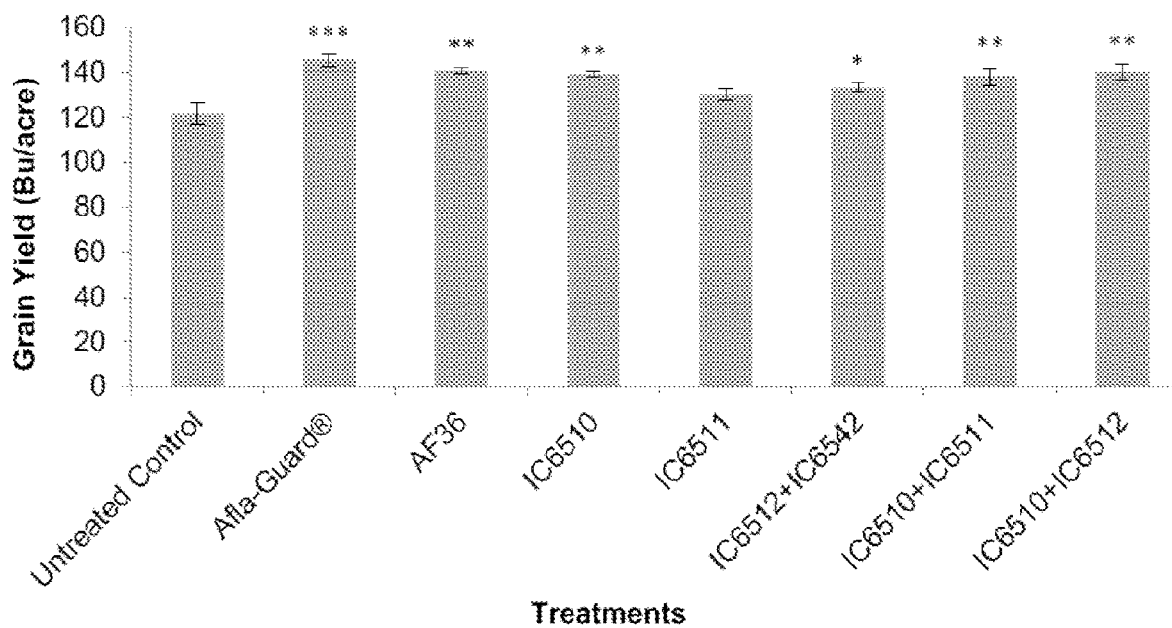
FIG. 2 shows the means of total grain yields for each biocontrol treatment. Yields were significantly lower in the untreated than treated plots (* $P<0.05$,  $P<0.010$, * $P<0.001$). The error bars represent standard errors.
Figure 3:
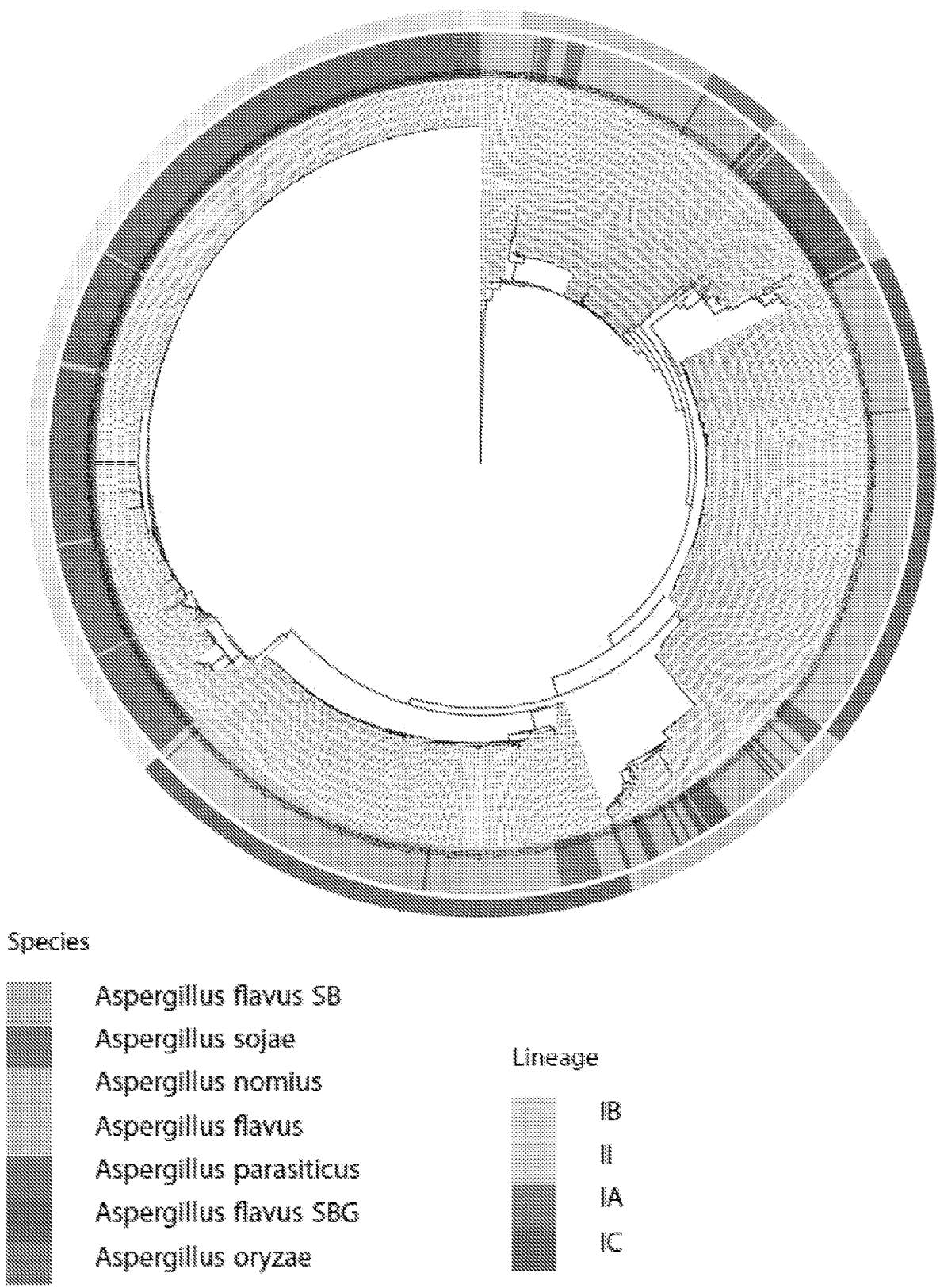
FIG. 3 shows the global phylogeny of different *Aspergillus* species and their lineages.

A HarvestMaster™ grain gauge attached to the Gleaner K2 Combine recorded grain weight, moisture content, and sample weight for yield analysis as corn was being harvested. Along with the differences in aflatoxin contamination, there were also significant differences noted between treatments for yield. The untreated control plots had a significantly lower yield than all of the treatments, with the exception of IC6511 (FIG. 2). Caution should be exercised when drawing conclusions about this due to excessive rainfall difference within the fields, which could have influenced these results. More data needs to be collected to determine if yields were influenced by nontoxigenic treatments.

SUMMARY

The various native non-aflatoxigenic and low AF-producing strains as well as the EPA-approved biological controls significantly reduced AF levels compared to the untreated control plots (P<0.1; FIG. 1). Although there was a significant difference in the AF levels from treated plots, Duncan's Multiple Range test did not reveal any further difference among treatments and the untreated check. Although native and commercially available biocontrol strains were equally effective in reducing AF levels, the combination of IC6510+IC6512 showed the greatest reduction of AF (2.1 ppb). Corn kernels were sampled and tested for aflatoxin levels 3 mo after biocontrol agents were applied to field plots.

While a high-density application of non-aflatoxigenic strains could displace toxigenic strains via competitive exclusion (Cotty and Bayman, 1993), or possibly through a mechanism of touch inhibition that downregulates aflatoxin biosynthesis (Huang et al., 2011), these competitive and inhibitory interactions do not completely explain why adding a strain of opposite mating type might further decrease aflatoxin levels. Since aflatoxin is a highly heritable trait (Olarte et al., 2012, Olarte et al., 2015) using formulations that include strains of opposite mating type could increase opportunities for sexual reproduction of native strains with applied non-aflatoxigenic strains and increase the proportion of atoxigenics in the population. Preliminary data from longitudinal sampling of plots treated with biocontrol strains shows increased sexual recombination in treated plots three months after biocontrol application compared to untreated plots. Moreover, previous studies showed that detached sclerotia placed on the surface of nonsterile soil form mature ascospores after just eight weeks of incubation (Horn et al., 2014). It is therefore plausible that sexual reproduction could give rise to a larger proportion of atoxigenics in the populations, even over a relatively short period of time. This could drive the greater reduction in aflatoxin levels compared to single-mating-type strains which would have fewer encounters with compatible mating partners.

Along with the differences in AF contamination, there were also significant differences observed between treatments for yield (FIG. 2). Many different factors including insect pressure (Pereira et al., 2000, Silva et al., 2018), weather-related stresses (Kucharik and Ramankutty, 2005, Rosenzweig and Hillel, 1998) and soil conditions (Ortiz-Torres, 2006, Vyn, 2010) can influence grain yields. Increased feeding activity by insects creates opportunities for fungal infection which can result in rotting of ears and stalks, and decreased yields (Wicklow, 1994). Insect control and other management practices that result in increased yields shift the balance in favor of non-aflatoxigenicity, whereas aflatoxin producing strains are more fit when insects are present (Drott et al., 2017), and yields are lower.

Aflatoxin biosynthesis is metabolically and energetically costly for the fungus (Calvo et al., 2002). *A. flavus* needs carbon from simple sugars such as glucose, sucrose, fructose, and maltose to synthesize the polyketide backbone (Payne and Brown, 1998) and maize kernels provide an abundant source of starch, accounting for 70% of the kernel weight (Wang et al., 2015). A larger proportion of non-aflatoxigenic or low AF-producing strains in the population of maize kernels could preserve starch reserves in kernels because the atoxigenics do not need to draw as much energy as their toxigenic relatives. This translates to more starch in kernels and a larger kernel weight and yield of maize per acre. This may explain why the untreated control plots had a significantly lower yield than all of the treatments ($P<0.05$), with the exception of IC6511 (FIG. 2). We analyzed our candidate biocontrol strains via HPLC for aflatoxin production and found that IC6511 produces low levels of AFB1 (20 ug/mL) in culture, not previously detected with Thin Layer Chromatography (TLC); this could explain why yields for the plot treated with IC6511 were lower than plots treated with the other candidate biocontrols that were all non-aflatoxigenic. The plots treated with Afla-Guard had the highest grain yields which were significantly higher than the untreated control ($P<0.001$). Rainfall data over a five-month period from May-September in 2015 ranged from 6 cm in May, 8.4 cm in June, 5.4 cm in July, 5.3 cm in August and 16.7 cm in September. These rainfall amounts are close to average for the months of May to August and the September rainfall amount reflects a tropical storm that occurred on September 2-5. Since all treatments were exposed to the same environments there is no indication that rainfall amount influenced these results.

The various native, non-aflatoxigenic *A. flavus* strains reduced aflatoxin levels and increased yield when compared with untreated controls. When we examined the influence of MAT1-1 or MAT1-2 strains alone in reducing aflatoxin contamination, the formulation that included two lineage IC strains (IC6510+IC6511) or two lineage IB strains (IC6512+IC6542) were not better in reducing aflatoxin levels than the single MAT1-1 or MAT1-2 strain formulations, whereas the MAT1-1/MAT1-2 formulation (IC6510+IC6512) showed the greatest reduction in aflatoxin levels. The full impact of formulations comprising a mix of sexually compatible MAT1-1/MAT1-2 mating types is expected long term because the mating process takes 6-11 mo in the laboratory (Horn et al., 2009); however, a signature of genetic exchange and recombination has been detected just 3 mo after biocontrol application. Thus, in nature, genetic exchange and recombination between the introduced biocontrol strain and the native population can occur within a 3 month window after the initial biocontrol application. These results suggest that biological control of AF contamination by deploying strains of opposite mating types impact the underlying population genetic structure and can potentially be more effective in the long-term than releasing strains of the same mating type or lineage. Additionally, a preliminary experiment in TX showed that paired MAT1-1/MAT1-2 strains resulted in a greater reduction in AF levels compared to the single MA TT-2 Afla-Guard application and the untreated control, and yields were similar to untreated even with no irrigation.

Example 2. Homothallic Fungal Strains

Homothallic fungi, which can outcross and which have low toxigenicity or are atoxigenic, may be useful in biocontrol compositions for reducing mycotoxin production in a field population of toxin producing fungi. The homothallic fungi maybe used alone or in combination with the heterothallic fungi as described herein.

TABLE 1

Self-fertility and outcrossing of homothallic *Aspergillus flavus* IC899 strain

| MAT1-1 | MAT1-2 | # sclerotia examined | % with ascospores |
|---|---|---|---|
| IC899* | | 533 | 94.5 ± 4.32 |
| IC899 | IC1179 | 81 | 36.7 ± 16.40 |
| IC899 | IC258 | 600 | 47.8 ± 4.01 |
| IC899 | IC307 | 185 | 95.1 ± 1.61 |
| IC899 | IC290 | 121 | 57.3 ± 3.34 |

*IC899 has both MAT1-1 and MAT1-2 mating types and is self-fertile

*Aspergillus flavus* strain (IC899) was crossed in the laboratory with itself and with heterothallic strains, either MAT1-2 (shown in Table 1) or MAT1-1 (data not shown). The degree of fertility was estimated by calculating the percentage of sclerotia with ascospore-bearing ascocarps. The high fertility observed from the self-cross indicates that the IC899 strain is functionally homothallic. The high fertility observed from the IC899 x IC307 cross indicates that IC899 can outcross with a strain that is strictly heterothallic. There is variation in fertility when IC899 is crossed to different MAT1-2 strains, as observed in previous work (Horn et al. *PLoS One;* 11(1):e0146169 (2016)).

Example 3. Genetic Factors Influencing the Efficacy and Persistence of Biocontrol of Aflatoxin Contamination in Maize A large acreage of maize grown in the southern United States is chronically at risk of aflatoxin contamination caused by *Aspergillus flavus*. Biocontrol treatments using atoxigenic strains of *A. flavus* can reduce contamination by up to 95%. Commercial biocontrol strains are of the mating type MAT1-2 and are applied annually for effective performance. Currently, there is interest in the development of sustainable biocontrol approaches to successfully reduce aflatoxin contamination. First, we examined the efficacy of RMb10, a novel biocontrol strain of the MAT1-1 type (same lineage as Afla-Guard strain but with a different mating type), in replicated large-scale field trials in AL, MS, NC, and TX from 2016 to 2018. Second, we investigated the genetic factors that may influence the persistence of biocontrol strains in the field. Isolates (n=300) of *A. flavus* were collected from specific maize fields in MS, NC, and TX. These fields had 3 to 7 years history of annual Afla-Guard treatment, but applications were terminated when harvested grain exhibited no aflatoxin contamination in subsequent seasons. In both experiments, isolates were screened for colony morphology, sclerotia production, mating type, and aflatoxin cluster composition, and then subjected to multi-locus sequencing using five loci (amdS, aflM, aflW, mfs, and trpC). Results of this study will provide insights into the population genetic structure of fields with reduced contamination and inform future biocontrol strategies.

Example 4. The Population Genomics of Biological Control in *Aspergillus flavus* and Aflatoxin Production

*Aspergillus flavus* causes ear rot of maize and produces aflatoxins (AFs). *A. flavus* is a soilborne filamentous fungus that commonly infects many economically important crops, such as corn, peanuts, cotton, treenuts, and spices, by contaminating them with AFs. In addition to aflatoxins, *A. flavus* also produces cyclopiazonic acid (CPA), an indole-tetramic acid that targets the liver, kidneys, and gastrointestinal tract of animals. Because of the adverse effects on human and animal health, the US Food and Drug Administration (FDA) strictly regulate the levels of AFs in grain. Grains must yield levels of AF below 20 parts per billion (ppb) for human consumption and 100 ppb for animal feed.

Aflatoxin biosynthesis is controlled by enzymes encoded by approximately 30 genes located in the 75-kb subtelomeric region of chromosome 3 (Carbone et al. 2007). Sequence polymorphisms and deletions in the aflatoxin gene cluster (Moore et al. 2009) as well as genome-wide variation separate *A. flavus* strains into two distinct lineages, IB and IC. Lineage IB is composed of partial and full cluster deletion strains and those with full clusters with many fixed polymorphisms. Strains that belong to lineage IB are non-aflatoxigenic (AF−) or producing very low AF levels, whereas IC comprises a mix of AF− and aflatoxigenic (AF+) isolates with full gene clusters (Moore et al. 2009). Aflatoxin production is a polygenic trait and influenced by multiple environmental factors such as soil nitrogen, pH, and carbon availability.

The management of AFs focuses on the application of non-aflatoxigenic biological control strains, either Afla-Guard® (active ingredient=NRRL 21882; lineage IB) or AF36 (=NRRL 18543; lineage IC), that competitively exclude native aflatoxigenic *A. flavus* strains for space and resources in corn ears (Dorner 2005; Moore et al. 2009). Biocontrol strategies have been shown to effectively reduce AF levels by −70-90% (Dorner 2004; Dorner 2008; Pitt & Hocking 2006; Yin et al. 2008). AF36 was registered with the EPA in 2003 for use on cotton and corn in Arizona and Texas. A nonsense mutation in the pksA gene early in the AF biosynthetic pathway renders AF36 non-aflatoxigenic; otherwise AF36 has a fully functional AF cluster and produces CPA (Ehrlich & Cotty 2004; Moore et al. 2009). Afla-Guard® was registered with the EPA in 2004 for reduction of AF contamination in peanuts and corn in the United States. Afla-Guard® is non-aflatoxigenic and missing the entire AF and CPA clusters (Chang et al. 2005; Moore et al. 2009). However, the lack of predictive models for aflatoxin contamination and high cost of application deter growers in moderate to low risk areas from applying the biocontrol products. Moreover, AF36 produces CPA and its application has been shown to significantly increase CPA contamination in grain (Abbas et al. 2011). While CPA is currently unregulated by the FDA, it has been linked to adverse health effects in humans and animals (Burdock & Flamm 2000).

Populations of *A. flavus* have a clonal and recombining population structure (Moore et al. 2013), and frequently maintain a mix of aflatoxigenic and non-aflatoxigenic strains (Chang et al. 2005; Cotty & Bhatnagar 1994). *A. flavus* is heterothallic and sexual reproduction occurs between isolates of opposite mating types belonging to different vegetative compatibility groups (VCGs) (Horn et al. 2009; Ramirez-Prado et al. 2008). Genetic exchange is also possible between compatible strains via heterokaryon formation within a VCG, a process known as parasexuality. In filamentous fungi, the vegetative compatibility system is a self/non-self recognition system controlled by a series of heterokaryon incompatibility (het) loci (Leslie 1993). Heterokaryon incompatibility is the inability of two strains to undergo fusion of vegetative fungal cells. Twelve putative het loci have been identified in *A. flavus* (Monacell 2014) and in most cases, alleles must be identical at all het loci for stable hyphal fusions to occur. Fungal individuals can be grouped into VCGs based on their multilocus genotypes provided markers are tightly linked to het loci (Monacell 2014).

Olarte et. al (2012) provided the first direct evidence of sexual recombination and identified chromosome crossover events in parents that influence toxin phenotypes of *A. flavus* progeny strains. Both aflatoxin and CPA clusters show high heritability from parents to progeny strains. Laboratory and field experiments suggest that a single round of sex can significantly increase genetic diversity; however, the impact of sexual reproduction in structuring natural populations of these fungi over time has not been studied. Current management practices recommend reapplication of biocontrol agents each growing season because presumably their population sizes decline but their influence on the native population structure is unknown. Here, we adopt a population genomics approach to explore the fate of released biocontrol strains in cornfields, for up to three years after initial application.

Sampling and DNA Isolation

Figure 4:
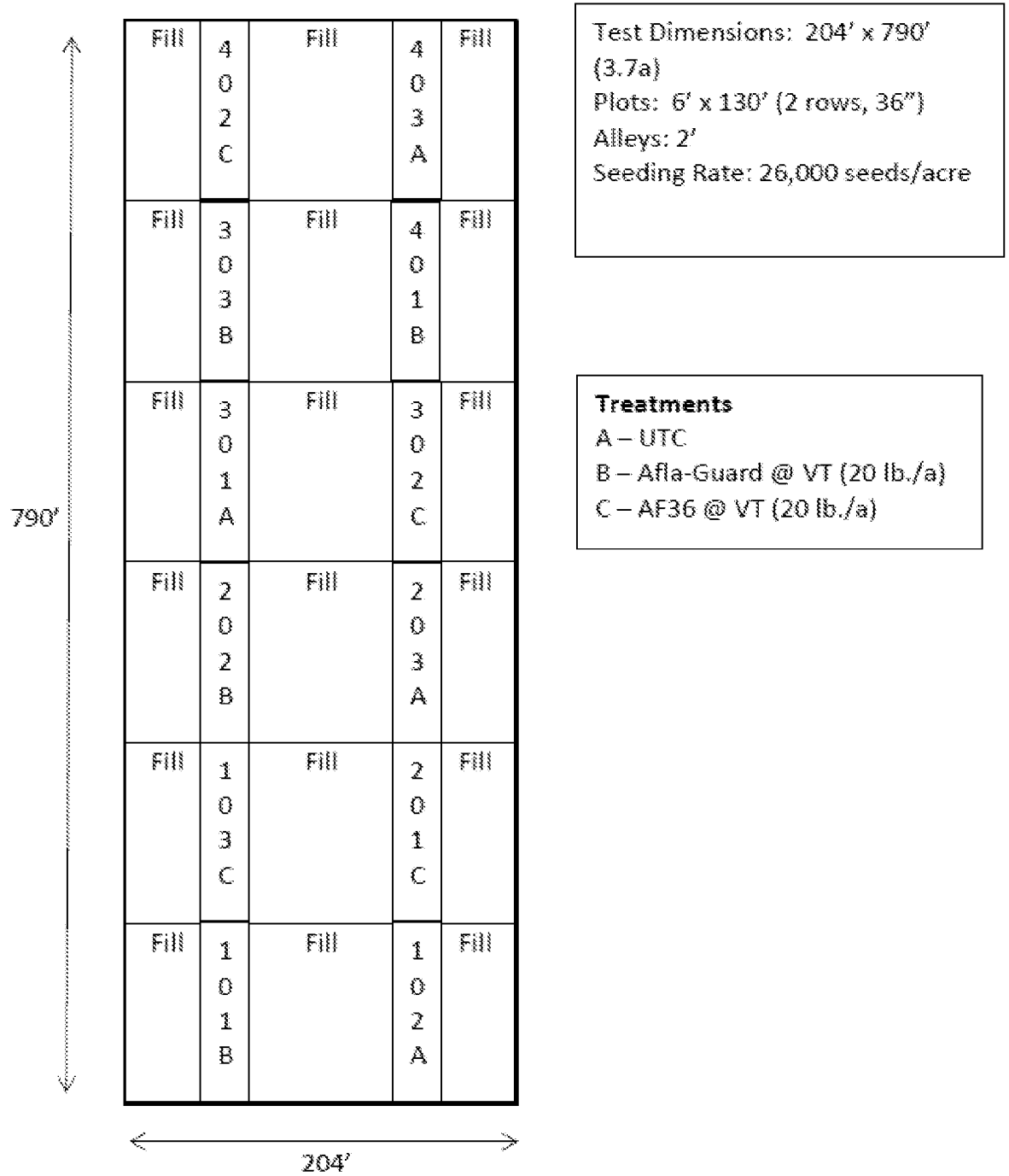
FIG. 4 shows the plot layout of cornfields in the longitudinally sampled biocontrol study (Example 4). This schematic shows the plot layout for the cornfields in Rocky Mount, NC in 2013 and 2014; all four states had similar plot layouts. Fields were split into 12 plots with three treatments: UTC (untreated), Afla-Guard®, and AF36 replicated 4 times each throughout the field (shown in different shades of gray). Each plot was made up of 8 130' rows of maize; all treatments and samples were taken from the center of rows 3 and 4 to ensure a 100' buffer separated treatments.
Figure 5:
FIG. 5 shows samples from commercial cornfields in Texas. Circled letters indicate the locations of sampling sites. Fields A and C were untreated, and fields B and D were treated with Afla-Guard® in 2011. Corn was planted continuously from 2011-2014 when samples were taken except for field B; corn was planted and rotated with wheat in 2013 in field B.

*Aspergillus flavus* was sampled in 2013 and 2014, from cornfields in Texas, North Carolina, Arkansas, and Indiana. Prior to our study, maize fields had no history of biological control application. Fields were separated into 12 plots with 8 130' rows in each plot with three treatments (FIG. 4): untreated (UTC), Afla-Guard®, and AF36 replicated four times. Biocontrols were applied at VT corn stage at a rate of 20 lb/acre. All treatments and samples were applied and taken from the middle of rows 3 and 4 of each plot to allow for a 100' buffer between treatments. Soil and kernel samples were collected, and *A. flavus* was isolated from each at three different time points: before biocontrol application (2013 UTC), three months prior to biocontrol application (2013 TRT), and one year after application (2014). *A. flavus* was isolated from soil by dilution plating and from surface-sterilized kernels, as described previously (Horn & Greene 1995). To examine more long-term changes in population structure after initial biocontrol application, we focused on four commercial cornfields in Texas (FIG. 5); fields A and C were left untreated, while fields B and D were treated with 20 lb/acre of Afla-Guard in 2011; fields A, C, and D were continually planted with corn; corn was rotated with wheat in 2013 in field B. Because aflatoxin assays in these fields consistently showed aflatoxin levels well below 100 ppb over several years, A. flavus was isolated in 2014 from surface-sterilized kernels and also included in population genomic analyses. Additionally, a farm near Palacios, in Jackson County, TX was included where the farmer never applied an atoxigenic biocontrol and did not have an aflatoxin problem. DNA was isolated from A. flavus spores using MOBIO UltraClean® Microbial DNA Isolation Kit (MO BIO Laboratories) with the following modifications. When resuspending the cells in MicroBead Solution, RNase A was added to degrade any RNA present. Spores were vortexed using the MOBIO Vortex Adapter and Disrupter Genie, incubated at 65° C., and vortexed again to ensure that spores were fully ruptured. Finally, DNA was eluted in PCR-quality water for genotyping by sequencing.

Genotyping by Sequencing

Double digest Restriction Site-Associated DNA Sequencing (ddRADseq) was used to identify Single Nucleotide Polymorphisms (SNPs) genome-wide (Peterson et al. 2012). These dense SNP markers allow us to unambiguously track the applied A. flavus biocontrol agents Afla-Guard® and AF36 in the field. Moreover, we can compare chromosomal phylogenies to identify when crossover or independent assortment events occurred between the introduced biocontrol agents and native strains. To determine optimal restriction enzyme combinations for ddRADseq, in silico digestions of A. flavus (NRRL 3357) and A. oryzae (RIB40) reference genomes were performed to identify pairs of enzymes that yielded approximately 5000 fragments that were 350-450 bp in size. By targeting this number of fragments, we were able to estimate the maximum number of strains that could be multiplexed on an Illumina NextSeq machine and achieve at least 20× coverage per individual.

Total genomic DNA was isolated and quantified using Quant-iT™ PicoGreen® dsDNA Assay Kit (Invitrogen). Two restriction enzymes, MluCI(Tsp509I) and MspI, were identified that would allow us to multiplex 576 strains and sequence 5000 fragments/individual to a depth of at least 20×. DNA (200 ng) was digested with both enzymes, a universal adapter was ligated to the overhangs produced by MluCI and one of 48 barcoded adapters was ligated to overhangs produced by MspI. A second quality check with Quant-iT™ PicoGreen® dsDNA Assay Kit was performed to ensure DNA was digested. Size selection was done using a Pippin Prep (Sage Science) to keep fragments in the range of 450-550 bp. A universal primer was annealed to the barcoded adapter and one of 12 indexed primers was annealed to the universal adapter followed by PCR amplification using KAPA HiFi Hotstart Readymix (Kapa BioSystems). This design ensured that only DNA sequences with both ligated adapters will be sequenced. All strains in each sublibrary were quantified using Bioanalyzer (Agilent) and then pooled in equimolar ratios. Sublibraries were quantified and a final pooling was performed before paired-end sequencing. The unique combination of indexed primer and barcoded adapter allowed for demultiplexing first by Illumina index and then by barcode. The DNA for all isolates was pooled and sequenced using 150 bp paired end reads on the Illumina NextSeq® platform.

Data Processing for Variant Discovery

All ddRADSeq data was analyzed using workflows implemented in the Mobyle SNAP Workbench. Briefly, the process_radtags script from the Stacks package (catchenlab.life.illinois.edu/stacks/) was used to demultiplex 48 barcodes for each Illumina NextSeq sublibrary. Trimmomatic was used to trim low quality bases from the end of reads and crop bases from the ends regardless of quality. Filtered read pairs were aligned to the A. oryzae RIB40 reference genome using the MEM algorithm in BWA (Li & Durbin 2009). Sequence alignment files generated from BWA were assembled into cohorts and genotyped using the HaplotypeCaller variant discovery pipeline in GATK v3.5-2 (McKenna et al. 2010). GATK variant calling is designed to maximize sensitivity, so there could be many false positives. Subsequent filtering of variants eliminated false positives and negatives and was performed according to GATK Best Practices recommendations (DePristo et al. 2011; Van der Auwera et al. 2013). Variant Call Format (VCF) files from GATK were subjected to various levels of filtering using VCFTOOLS (DePristo et al. 2011) and VCF files were visualized in JBrowse (Buels et al. 2016).

Phylogenetic Inference and Patristic Distances

We inferred maximum likelihood (ML) phylogenies of A. flavus at different sampling time points: pre-treatment kernel and soil isolates, 3-month post-treatment kernel isolates, and one-year post-treatment soil and kernel isolates. Additionally, kernel isolates in Texas were examined 3 years after treatment with Afla-guard. ML analysis was performed using the program Randomized Axelerated Maximum Likelihood or RAxML version 8, which is accessible through the CIPRES RESTful application (CRA) programmer interface. The best-scoring ML majority rule consensus tree was based on 1,000 rapid bootstrap searches in RAxML using a GTR-GAMMA model of rate heterogeneity with empirical base frequencies; all phylogenies were rooted with NRRL 29506 (IC277). Trees were visualized using the Tree-Based Alignment Selector (T-BAS, version 2.0) toolkit (Carbone et al. 2017; Miller et al. 2015).

The possibility of released biocontrol agents recombining with native strains was first examined using pairwise evolutionary distance or patristic distance. A patristic distance is the sum of the length of branches that connect any two nodes in a phylogeny. A matrix of patristic distances, normalized to a maximum value of one, was generated for all pairs of terminal nodes that represent sampled individuals. When calculated separately for phylogenies inferred from different chromosomes and compared, such distances can identify incongruences in tree topologies that may indicate genetic exchange and recombination, horizontal gene transfer and genomic re-assortment. Patristic distances were calculated using DendroPy and displayed as a heat map in T-BAS v2.0 using outer rings (one per chromosome) that surround the total evidence inner tree that was based on the concatenated chromosomal character matrix. In the heat map a blue color across most chromosomes indicates close genetic similarity to the selected biocontrol strain; a red color across one or more chromosomes indicates high genetic divergence. Inter-lineage recombination would result in strains that have blue, red and intermediate colors indicating a mixed genetic background.

Population Structure and Mating Type Distribution

Population structure was first examined using principal component analysis (PCA). PCA uses a variance-covariance matrix to reduce the dimensionality of the original variables into a smaller number of new variables called principal components. The principal components (eigenvectors) are different axes of variation that explain most of the variance in the original data. The first eigenvector or PC1 considers the most variation possible with subsequent eigenvectors, PC2, PC3, etc., having less variation. Principal components were normalized to sum to 1 to reveal which eigenvectors explained more than half of the genetic variation, and the number of significant axes of variation was determined using the Tracy-Widom statistic. The number of distinct k clusters was determined using the Gap Statistic, which is an unbiased estimate of the number of distinct clusters based on the top-3 PCs with the largest eigenvalues. Significant PC's and PCA clusters were displayed in three-dimensional graphs using the SCATTERPLOT3D package in R. Tests of association of k cluster with lineage (IA and IB), sampling location (TX, IN, NC, AR), treatment (Afla-Guard, AF36, UTC) and substrate (soil and kernel) were performed using Fisher's exact test, implemented in R (R Core Team 2016). Population parameter estimates were calculated separately for untreated and treated samples within each lineage using Arlequin v.3.5.1.2.

The degree of genetic admixture and the optimal number of k clusters was determined using ParallelStructure, an R-based implementation of STRUCTURE version 2.3.4 accessible through the CIPRES RESTful application (CRA) programmer interface. Structure-formatted files were generated from genome-wide SNPs using SNAP Map (Aylor et al. 2006). The admixture model implemented in STRUCTURE was used to assign individuals to k clusters. Estimates of allele frequencies and membership probabilities of individuals in subpopulations were based on a Markov Chain Monte Carlo (MCMC) strategy of 100,000 sampling iterations after a burn-in period of 50,000 iterations; three independent simulations for possible k values ranging from 1 to 10 were performed for each subpopulation. To determine the optimal k, probability distributions were examined using LnP(D) and delta K methods implemented in Structure Harvester v0.6.93. The estimated cluster membership coefficient matrices were examined in CLUMPP v1.1.2 to determine the optimal number of k clusters across multiple runs. The individual cluster membership results from Structure were visualized in T-BAS v2.0 as outer rings surrounding the total combined chromosomal ML phylogeny.

In the presence of strong population structure mating types distributions were examined separately for each distinct genetic cluster. Mating types were scored using diagnostic ddRADSeq fragments located within the MAT1-1 idiomorph spanning positions 1,581,022-1,581,132 on chromosome 6 of the *A. oryzae* reference genome. A 1:1 distribution of MAT1-1 and MAT1-2 is indicative of populations undergoing sexual reproduction and this was tested using a binomial test implemented in MS Excel. The test was also performed on clone-corrected haplotypes to correct for skewness in mating type distributions due to clonal amplification. Haplotypes were extracted from genome-wide SNPs using SNAP Map. Clone-correction was performed by counting the total number of unique haplotypes in each MAT1-1 and MAT1-2 category; individuals or haplotypes containing both mating types were counted twice as a MAT1-1 and a MAT1-2. A representative sample of 47 isolates from each MAT idiomorph were selected for PCR validation using MAT1-1 and MAT1-2 specific primers, as reported previously (Ramirez-Prado et al. 2008). Mating type distributions were examined for longitudinal samples from 1) untreated and treated plots in each state and 2) lineage IB and IC sampled across all states.

Phylogenetic Congruence and Recombination

Since populations of *A. flavus* are reported to have both a clonal and recombining population structure (Moore et al. 2013), phylogenetic congruence was used to further examine the contributions of clonality and recombination in the evolution of lineages, VCGs and individuals. This phylogenetic method implemented in the Hypha package module of Mesquite v3.51 displayed the clonal and recombinant history of each ancestral node and all of its descendant strains. Specifically, Hypha was used to compare the internodal support values harvested from each chromosomal phylogeny on the total evidence tree inferred from a concatenated SNP matrix of chromosomes 1-8. Nodal grid support values were based on a bootstrap threshold support value of 70% and were output as node annotations on the total evidence display tree in Mesquite. Support values were visualized in T-BAS v2.0 (Carbone et al. 2017) for each chromosome phylogeny using grids on branches of the display tree with colors showing node bipartitions that were supported at a bootstrap support value ≥70% (black color) or <70% (white color); if the specific node bipartition was not found in the display tree this was reported as missing or inapplicable (grey color). Grids that were filled in with mostly black squares indicated that the descendants of that node were predominantly clonal. High conflict (red color) was used to indicate a node bipartition in the chromosome tree that conflicted with the displayed tree at a bootstrap support value ≥70% most likely due to recent recombination (i.e. independent assortment and crossovers) among strains in descendant branches at terminal nodes or infrequent recombination at internal nodes. Low conflict (cyan color) was used for nodes that were not recovered by the bootstrap analysis because there was either insufficient variation or too much confounding variation (i.e. homoplasy) due to extensive recombination among strains in descendant branches. We would expect node bipartitions that comprise strains that belong to the same VCG to be congruent across all chromosomes; if some chromosomes show high conflict this could be the result of parasexual recombination within a VCG. With regard to the present application and grayscale figures, the gradient from white to black represents highest to lowest conflict, respectively.

Chromosomal Linkage Disequilibrium

Genome-wide linkage disequilibrium (LD) between SNP markers distributed across eight chromosomes was performed using Haploview 4.2. Both $r^2$ and D' pairwise LD measures were calculated between adjacent SNP markers in all populations for each distinct time point: pre-treatment, 3 months, 1 year and 3 years post-treatment. Intra-chromosomal LD blocks were estimated using the Solid Spine (SS) method of Haploview using the default parameters and a missingCutoff of 0.8. The SS algorithm identifies an LD block if the first and last markers in a block are in strong LD with all intermediate markers, but those intermediate markers can be in weak LD or no LD with each other. Haploview outlines the edge of the spine of strong LD in a triangular matrix of pairwise LD statistics. In the Haploview coloring scheme bright red represents strong LD (LOD≥2, D'=1), shades of pink/red represent intermediate LD (LOD≥2, D'<1), blue represents weak LD (LOD<2, D'=1) and white represents no LD (LOD<2, D'<1).

Aflatoxin Production

Representative samples of isolates were selected for aflatoxin quantitation based on their degree of genetic admixture and membership in lineages IB and IC. Aflatoxin was quantified using a high-throughput method, which allows detection of AF B1 production from fungal mycelia in liquid culture. Briefly, isolates were grown on PDA plates for a total of 7 days—5 days in the dark and 2 in light—at 30° C. Glass vials with 8 mL of YES media were inoculated with a loop-full of conidia for each isolate, with three replicates grown per isolate. Liquid cultures were incubated in the light at 30° C. for 7 days. For each culture a 1 mL aliquot of media was transferred to a new vial, 1 mL of chloroform was added, samples were vortexed, and then allowed to separate at rest. A total of 500 μL of the chloroform layer was transferred to a clean vial and evaporated under nitrogen stream. Dried aflatoxin samples were resuspended in 1 mL of methanol for analysis and purified by passing through 1 mL polypropylene SPE tubes containing 200 μL alumina basic. Aflatoxin quantifications were performed by reverse phase HPLC at the Biomanufacturing Training and Education Center's Bioprocess and Analytical Services at North Carolina State University following previously published specifications (Huang & Elmashni 2007).

Results

Sampling and Variant Discovery

A total sample of 888 isolates was examined across all states, treatments and time points for DNA isolation and sequencing (Table 2). This included a panel of 26 reference strains for which mating type, toxin profile, VCGs and multilocus haplotypes were known and used to cross-validate genotyping by sequencing results (Table 3). The total number of isolates sampled from each commercial cornfield in Texas was as follows: field A (22), filed B (26), field C (58), field D (51) and Palacios (4). The total number of variants discovered from GATK analysis and different levels of filtering for max-missing (MM) and minor allele frequency (MAF) is shown in Table 4. To ensure that sufficient variation was retained to track biocontrol strains, a MAF=0.0 and MM=0.9 was used for phylogenetic inference, calculation of patristic distances, phylogenetic congruence, and LD analysis. More stringent filtering with MM set to 1.0 was used for PCA, STRUCTURE, population parameter estimation and clone-correction for mating type distributions.

TABLE 2

Population Samples of *A. flavus*.

| State | 2013 UTC | 2013 TRT | 2014 |
|---|---|---|---|
| TX | 40 | 20 | 153 |
| NC | 39 | 20 | 141 |
| AR | 39 | 20 | 55 |
| IN | 30 | 9 | 62 |
| Total | 148 | 69 | 411 |

TABLE 3

Source and mycotoxin production of reference *A. flavus* isolates

| IC | NRRL | MAT | Origin | VCG | $B_1$ | $B_2$ | Total Aflatoxins | CPA |
|---|---|---|---|---|---|---|---|---|
| IC201 | 21882 | 2 | GA | 24 | 0 | 0 | 0 | 0 |
| IC217 | 20024 | 1 | GA | 1 | 4.8 (0.8) | 0 (0) | 4.8 (0.8) | |
| IC218 | 20025 | 1 | GA | 1 | 0.4 (0.1) | 0 (0) | 0.4 (0.1) | |
| IC219 | 20041 | 1 | GA | 2 | 1.6 (0.8) | 0 (0) | 1.6 (0.8) | |
| IC220 | 20042 | 1 | GA | 2 | 2.1 (2.9) | 0 (0) | 2.1 (2.9) | |
| IC221 | 20035 | 2 | GA | 4 | 41 (5) | 0.2 (0) | 41.2 (5) | |
| IC222 | 20036 | 2 | GA | 4 | 5.1 (0.7) | 0 (0) | 5.1 (0.7) | |
| IC225 | 20027 | 1 | GA | 5 | 5.5 (3.4) | 0.1 (0.1) | 5.6 (3.5) | |
| IC226 | 20029 | 1 | GA | 5 | 9.5 (2) | 0.1 (0) | 9.6 (2) | |
| IC229 | 29459 | 2 | GA | 6 | 39.2 (22.4) | 0.8 (0.5) | 40 (22.9) | 22.5 (3.8) |
| IC230 | 29460 | 2 | GA | 6 | 15.8 (13.3) | 0.3 (0.2) | 16.1 (13.5) | 26.9 (3.2) |
| IC234 | 29464 | 2 | GA | 14 | 85.6 (5.8) | 1.4 (0.3) | 87 (5.7) | 60.7 (8.4) |
| IC235 | 29465 | 2 | GA | 14 | 104.2 (16.7) | 1.7 (0.1) | 105.9 (16.8) | 65.6 (3.1) |
| IC243 | 20050 | 1 | GA | 17 | 101.4 (12.8) | 1.1 (0.2) | 102.5 (13) | |
| IC244 | 29473 | 1 | GA | 17 | 104.3 (10.3) | 1.7 (0.1) | 106 (10.5) | 64.9 (4.2) |
| IC253 | 29482 | 2 | GA | 24 | 0 (0) | 0 (0) | 0 (0) | 0 (0) |
| IC277 | 29506 | 2 | GA | 32 | 0 (0) | 0 (0) | 0 (0) | 99.6 (20.7) |
| IC278 | 29507 | 1 | GA | 33 | 99.4 (46.2) | 1.8 (1.1) | 101.2 (47) | 76.8 (4.8) |
| IC301 | 29530 | 1 | GA | 56 | 16.8 (3.3) | 0.1 (0) | 17 (3.3) | 100.3 (17.6) |
| IC307 | 29536 | 2 | GA | 62 | 139.8 (5.1) | 3.1 (0.1) | 142.9 (5.1) | 77.2 (1.5) |
| IC308 | 29537 | 1 | GA | 63 | 39.8 (6.5) | 0.6 (0.1) | 40.4 (6.6) | 183.5 (18.3) |
| IC310 | 35736 | 1 | NC | | 0 | 0 | 0 | 0 |
| IC311 | 35737 | 1 | AL | | 0 | 0 | 0 | 0 |
| IC313 | 35739 | 2 | TX | 76 | 0 | 0 | 0 | 0 |
| IC904 | 5590 | 2 | JP | | 0 | 0 | 0 | 0 |
| IC1179 | 18543 | 2 | AZ | YV36 | 0 | 0 | 0 | 0 |

Culture collection designations: IC (I Carbone), NRRL (Agricultural Research Service Culture Collection, Peoria, Illinois). Mating-type desginations are from Ramirez-Prado et al. (2008) and VCG is based on Horn and Greene (1995). Mean mycotoxin concentrations (μg/mL; n = 3) are shown; standard deviations are indicated in parentheses. Isolates were grown on yeast extract-sucrose broth in vials at 30° C. and cultures were analyzed for mycotoxin production via high-performance liquid chromatography (Horn et al. 1996)

TABLE 4

Number of unfiltered and filtered SNPs for population genomic analysis[1]

| Population | Unfiltered | MAF = 0.1 MM = 0.9 | MAF = 0.0 MM = 0.9 | SNPs[2] |
|---|---|---|---|---|
| 2013 UTC | 451,283 | 1,933 | 27,529 | 2,724 |
| 2013 TRT | 451,283 | 1,645 | 29,595 | 5,095 |
| 2014 | 447,324 | 1,783 | 25,351 | 5,323 |
| TX Commercial | 271,813 | 1,366 | 15,927 | 3,201 |

[1]Minor Allele Frequency = MAF; Max-Missing = MM.
[2]Number of SNPs obtained by collapsing multiple DNA sequence alignments after filtering (MAF = 0.0 and MAF = 0.9) using SNAP Map (Aylor et al. 2006) and excluding all sites with missing data.

Phylogenetic Inference and Patristic Distances

The best-scoring ML majority rules consensus trees were inferred across all four populations of *A. flavus* at three different time points: untreated, three months and one year after a one-time controlled application of *A. flavus* biocontrols (FIGS. 6A-D). Several consistent patterns were observed across all phylogenies, including 1) strong phylogenetic separation between lineages IB and IC, across all eight chromosomes; 2) longer branches for strains within lineages IC than within IB, and more variation in patristic distances among strains in lineage IC, indicative of a history of recombination. For example, both clonality and recombination are discernable across chromosomes for patristic distances using AF36 as a reference in the untreated plots; 3) AF36 was sampled less frequently than AG in native soils and also after biocontrols were applied; and 4) both lineages IB and IC were represented in field populations; however, their frequencies changes, either transiently (3 months) and after 1 year to favor lineage IB (Table 6). This skew in the dominance of lineage IB over IC was also evident in the commercial TX cornfield which was sampled 3 years after Afla-Guard® was applied (FIGS. 7A-D).

Patristic distances between strains in lineage IC were highly variable making it possible to distinguish clonality (zero length branches) from putative recombinants (long branches), and this clonal and recombining population structure was manifested with patristic distances spanning the entire heat map scale. By contrast, patristic distances within IB were very short in longitudinally sampled cornfields in TX, NC, AR and IN as well commercial cornfields in TX; limited sequence variation in lineage IB made it difficult to determine the degree of similarity between native strains and Afla-Guard® or between native strains and AF36. This was corrected by adjusting the patristic scale so that the maximum color value fell within lineage IB, and this revealed heterogeneity in patristic distances and potential clonal and recombining lineages in populations. *A. flavus* lineages IB and IC are clearly separated across all phylogenies, which suggests a lower frequency of inter-lineage genetic exchange and recombination. This genetic isolation between lineages IB and IC is further supported by patterns of deletions in the aflatoxin gene cluster. With the exception of seven partial cluster strains, all strains that belonged to lineage IC had full clusters. Lineage IB strains harbored full, partial or missing AF clusters; however, clonal lineages in IB included strains with predominantly missing AF clusters.

Population Structure and Mating Type Distribution

The Gap statistic in PCA analysis revealed two distinct clusters across all sampling times that were significantly associated with lineage (P<0.001; FIGS. 8A-D). There was no significant association of cluster with state or treatment. The observed dispersal of points in principal component space indicated greater diversity within lineage IC compared to IB in untreated fields; this was also supported by nucleotide diversity estimates (Table 5) for untreated fields sampled one year, and three years after biocontrol application. This trend was also observed for treated fields across sampling times. Moreover, three months after biocontrol applications both lineages IB and IC had higher nucleotide diversity estimates than the 2013 UTC fields (Table 5).

TABLE 5

Population parameters estimates in *A. flavus* across treatments and years.

| | Lineage | Treatment | n$^a$ | π$^b$ | π/bp$^c$ | q$^d$ | q/bp$^e$ | Tajima D$^f$ |
|---|---|---|---|---|---|---|---|---|
| 2013 UTC | IB | Untreated | 51 | 5.09 | 0.00171 | 10.224 | 0.00343 | −1.7184 |
| | IC | Untreated | 97 | 30.75 | 0.01032 | 114.247 | 0.03834 | −2.489 |
| 2013 TRT | IB | Treated | 53 | 11.16 | 0.00182 | 25.562 | 0.00416 | −1.9971 |
| | IC | Treated | 16 | 73.48 | 0.01197 | 74.739 | 0.01218 | −0.0733 |
| 1 year | IB | Untreated | 69 | 8.05 | 0.00093 | 22.481 | 0.00259 | −2.2026 |
| | | Treated | 167 | 6.06 | 0.0007 | 28.46 | 0.00328 | −2.5121 |
| | IC | Untreated | 127 | 77.48 | 0.00716 | 203.97 | 0.01884 | −2.0697 |
| | | Treated | 48 | 54.99 | 0.00508 | 133.169 | 0.0123 | −2.1518 |
| 3 years | IB | Untreated | 61 | 9.33 | 0.00136 | 32.266 | 0.00471 | −2.4941 |
| | | Treated | 72 | 11.94 | 0.00174 | 28.472 | 0.00415 | −1.9957 |
| | IC | Untreated | 23 | 346.7 | 0.04762 | 490.678 | 0.06738 | −1.1989 |
| | | Treated | 5 | 98.8 | 0.01357 | 107.04 | 0.0147 | −0.5873 |

| | Fu & Li D$^g$ | Fu & Li D*$^h$ | s$^i$ | Hud4Nc$^j$ | Hud4Nc/bp$^k$ | g/bp$^l$ | c/u$^m$ | F$_{ST}^n$ |
|---|---|---|---|---|---|---|---|---|
| 2013 UTC | −3.5956 | −3.1179 | 46 | 7.21 | 0.002419 | 0.02514 | 0.724 | 0.324 |
| | −4.3813 | −4.3813 | 588 | 1.373 | 0.000461 | 0.00248 | 0.6558 | |
| 2013 TRT | −5.2863 | −4.8075 | 116 | NA | NA | 0.0231 | 0.5541 | 0.422 |
| | −0.5335 | −0.0049 | 248 | 12.55 | 0.002045 | 0.01654 | 1.3585 | |
| 1 year | −3.4731 | −3.002 | 108 | 1.373 | 0.000158 | 0.00442 | 1.7061 | 0.003 |
| | −5.9343 | −5.9344 | 162 | NA | NA | 0.00195 | 0.5939 | |
| | −2.3811 | −2.0774 | 1105 | 4.234 | 0.000391 | 0.01826 | 0.9694 | 0.01 |
| | −4.5455 | −3.721 | 591 | 0.038 | 0.000004 | 0.01039 | 0.8451 | |

TABLE 5-continued

Population parameters estimates in *A. flavus* across treatments and years.

| | | | | | | | | |
|---|---|---|---|---|---|---|---|---|
| 3 years | −4.6396 | −4.0163 | 151 | NA | NA | 0.01305 | 2.7721 | 0.008 |
| | −1.9957 | −0.5126 | 138 | 4.578 | 0.000668 | 0.00564 | 1.3586 | |
| | −1.3572 | −0.9681 | 1811 | 6.905 | 9.48E−05 | 0.07447 | 1.1052 | 0.15 |
| | 0.9091 | −0.5873 | 223 | NA | NA | 0 | 0 | |

[a] Number of *A. flavus* isolates from Lineage IB and IC included in the analysis.
[b] Average pairwise differences between nucleotides.
[c] Per-site estimate of the average pairwise differences between nucleotides.
[d] Watterson's estimator of the lineage-scaled mutation rate.
[e] Watterson's estimator of the lineage-scaled mutation rate per site.
[f] Taijima's D estimates the departure from neutrality.
[g] Fu and Li D is a measure of the departure of the frequency spectrum from neutral expectations
[h] Fu and Li D* is a measure of the departure of the frequency spectrum from neutral expectations.
[i] Number of segregating sites.
[j] Hudson's 4Nc estimate of recombination
[k] Per-site estimate of Hudson's 4Nc
[l] Estimate of gamma population recombination rate per base.
[m] Hudson's c/µ estimate
[n] Wright's FST measure of genetic differentiation betwene lineages or treatments.

STRUCTURE admixture analysis found that the most likely value of k in the 2013 UTC and 2013 TRT populations was 3 using the Evanno method and 7 based on STRUCTURE LnP(D). The estimate from LnP(D) was more consistent with the distinct clades observed in phylogenies for these populations FIGS. 9A-D. Structure LnP(D) and Evanno yielded best cluster estimates of 6 and 2, respectively, for populations sampled one year after biocontrol application. The TX commercial cornfields that were sampled 3 years after Afla-Guard® was applied comprised at most 3 distinct clusters, as estimated from LnP(D).

The uncorrected and clone-corrected counts for MAT1-1 versus MAT1-2 for each state and field plots (untreated versus treated) are shown in Table 6. Three months after biocontrol treatments were applied, uncorrected counts of mating types in AR and IN were significantly skewed (P<0.05) towards MAT1-2, which represents a significant reversal from clone-corrected counts in the untreated AR and IN fields, which were predominantly MAT1-1 (P<0.05). One year after biocontrol application, the clone-corrected counts of mating types in treated fields in TX, NC, and IN were significantly skewed (P<0.01) towards MAT1-1. The clone-corrected MAT1-1: MAT1-2 ratio in the untreated commercial cornfields in TX did not deviate significantly from 1. The distribution of mating types was also examined within lineages IB and IC for each population sampled longitudinally (Table 7). Mating type frequencies, corrected for duplicate genotypes, were approximately 1:1 before treatment (2013 UTC), 3 months after treatment (2013 POST), and 3 years after treatment (3 years POST); one year after treatment mating type frequencies were significantly skewed to MAT1-1 (P<0.05) for both lineages IB and IC. The clone corrected ratio of full AF gene cluster: missing cluster in lineage IB was 2.4, 1.1, and 1.7 for 1 year POST, 2013 TRT and 2013 UTC, respectively (Table 7).

TABLE 6

Distribution of mating types in *A. flavus* across states, treatments and years[1]

| | 3 months | | | | 1 year | | | | 3 years | | | |
|---|---|---|---|---|---|---|---|---|---|---|---|---|
| | Untreated | | Treated | | Untreated | | Treated | | Untreated | | Treated (AG) | |
| State | MAT1-1 | MAT1-2 | MAT1-1 | MAT1-2 | MAT1-1 | MAT1-2 | MAT1-1 | MAT1-2 | MAT1-1 | MAT1-2 | MAT1-1 | MAT1-2 |
| TX | 26 (16) | 19 (12) | 13 (9) | 7 (6) | 18 (18*) | 29 (9) | 61 (30**) | 43 (11) | 48(42) | 70*(50) | 44(32) | 34(25) |
| NC | 19 (14) | 20 (14) | 8 (7) | 12 (3) | 29* (13) | 17 (9) | 65 (30**) | 30 (14) | | | | |
| AR | 20 (18*) | 19 (9) | 0 (0) | 20** (6*) | 6 (5) | 6 (4) | 26 (11) | 17 (12) | | | | |
| IN | 29** (7*) | 2 (2) | 1 (1) | 9* (4) | 8* (1) | 2 (1) | 39** (6) | 13 (5) | | | | |

[1] Clone corrected number for each mating type is shown in parentheses; 0.01 < *P < 0.05 and **P < 0.01.

TABLE 7

Distribution of lineages, mating types and AF cluster type in *A. flavus* across treatments and years[1]

| | | | Mating Type | | AF Cluster Type | | |
|---|---|---|---|---|---|---|---|
| Treatment | Lineage | n[2] | MAT1-1 | MAT1-2 | Full | Partial | Missing |
| 2013 UTC | IB | 63 (29) | 17 (12) | 46** (17) | 25 (17) | 3 (2) | 35 (10) |
| | IC | 109** (67**) | 71** (34) | 38 (33) | 108 (67) | 1 (1) | 0 |
| 2013 TRT | IB | 65** (27) | 12 (10) | 53** (16) | 18 (16) | 3 (3) | 48 (14) |
| | IC | 28 (23) | 11 (9) | 17 (14) | 27 (22) | 2 (2) | 0 |
| 1 year POST | IB | 251** (81) | 136 (50*) | 115 (31) | 67 (51) | 12 (9) | 172 (21) |
| | IC | 187 (81) | 128** (49*) | 59 (32) | 184 (78) | 3 (3) | 0 |

TABLE 7-continued

Distribution of lineages, mating types and AF cluster type in *A. flavus* across treatments and years[1]

| Treatment | Lineage | n[2] | Mating Type | | AF Cluster Type | | |
| --- | --- | --- | --- | --- | --- | --- | --- |
| | | | MAT1-1 | MAT1-2 | Full | Partial | Missing |
| 3 years POST | IB | 148** (80**) | 63 (30) | 85* (40) | 113 (68) | 3 (3) | 32 (9) |
| | IC | 41 (37) | 25 (21) | 16 (15) | 40 (36) | 1 (1) | 0 |

[1]Clone corrected number for each mating type is shown in parentheses; $0.01 < *P < 0.05$ and $**P < 0.01$.
[2]Significance values tested the null hypothesis of no significant difference in the uncorrected and corrected lineage counts across all states.

Phylogenetic Congruence and Recombination

Figure 9A:
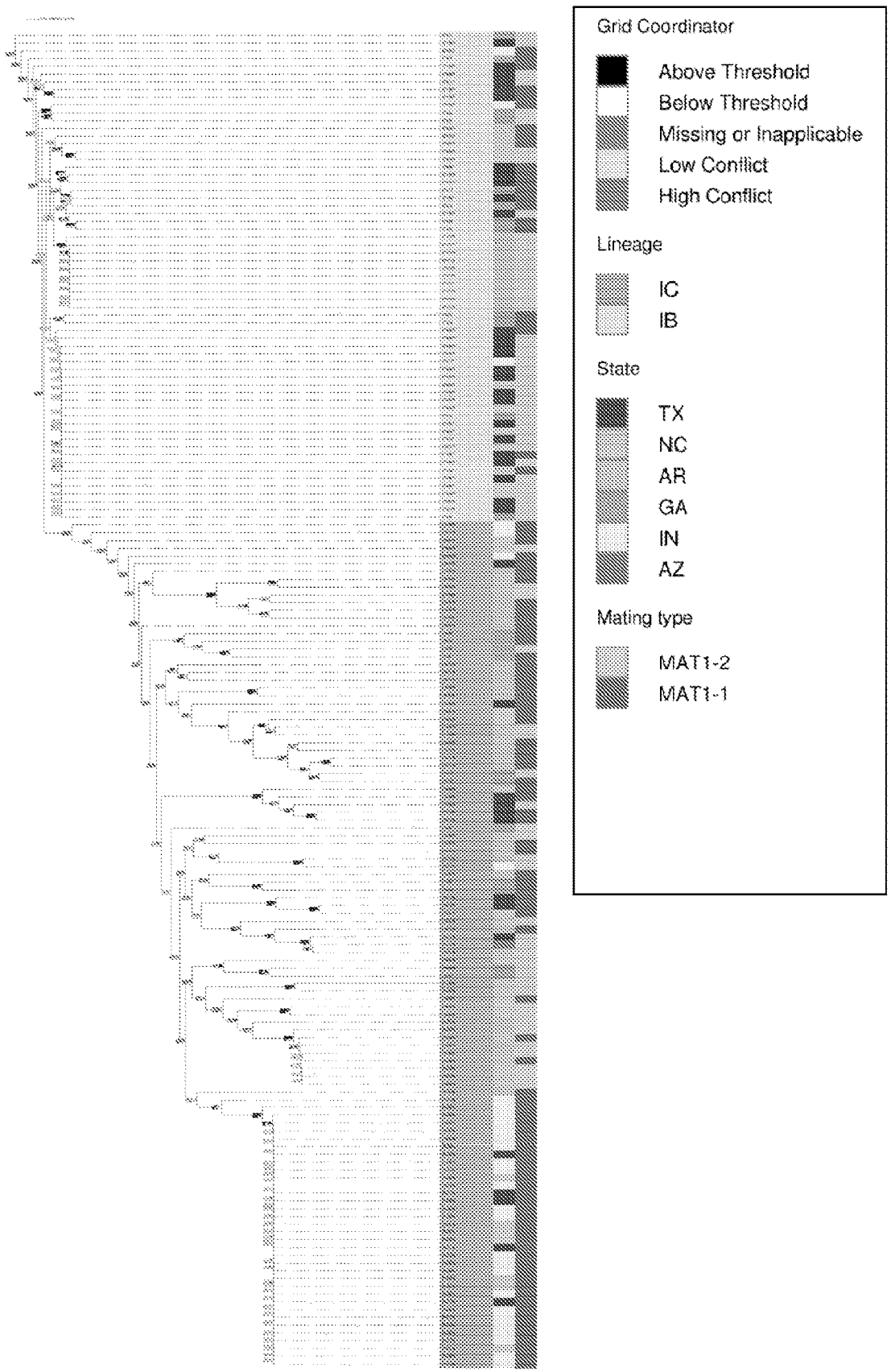
Figure 9B:
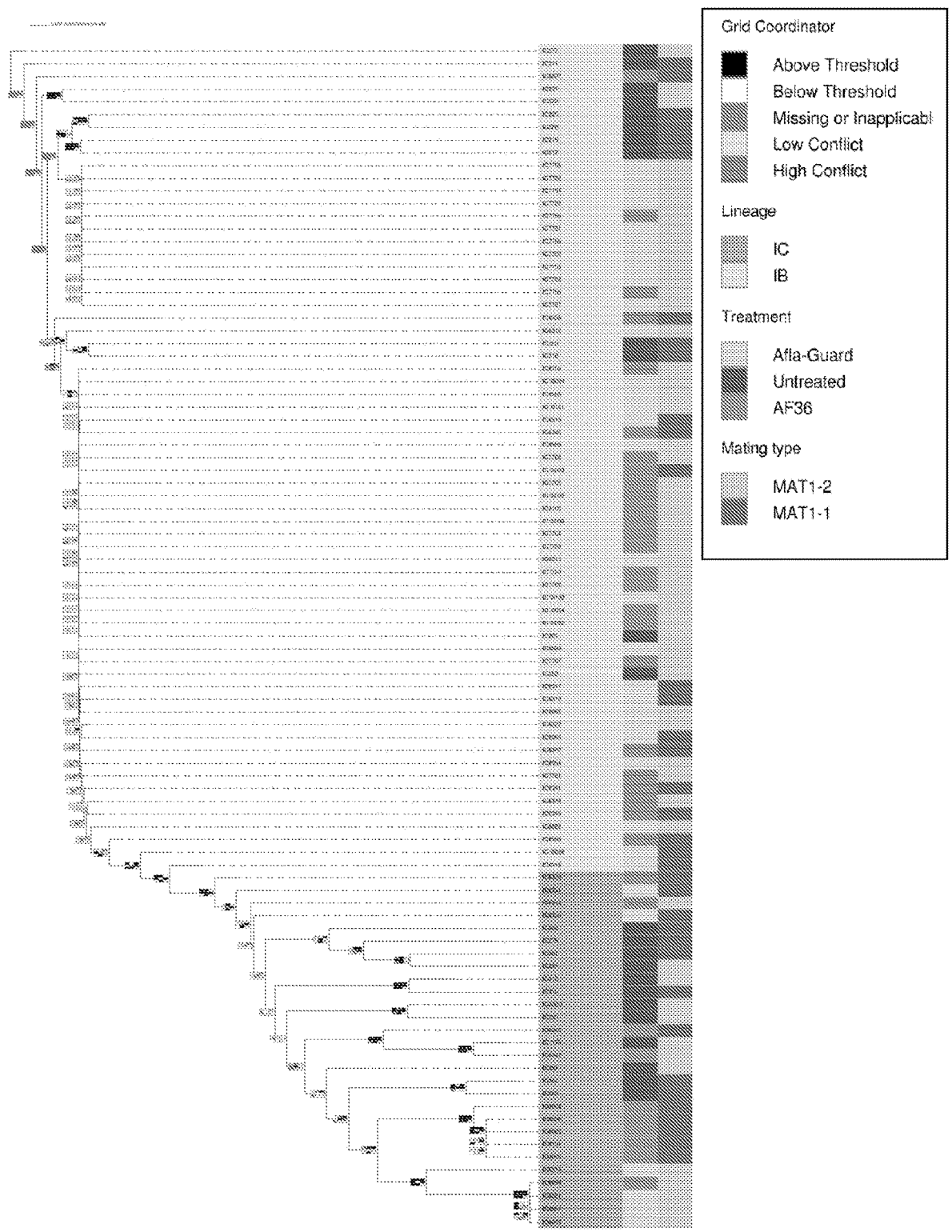
Figure 9C:
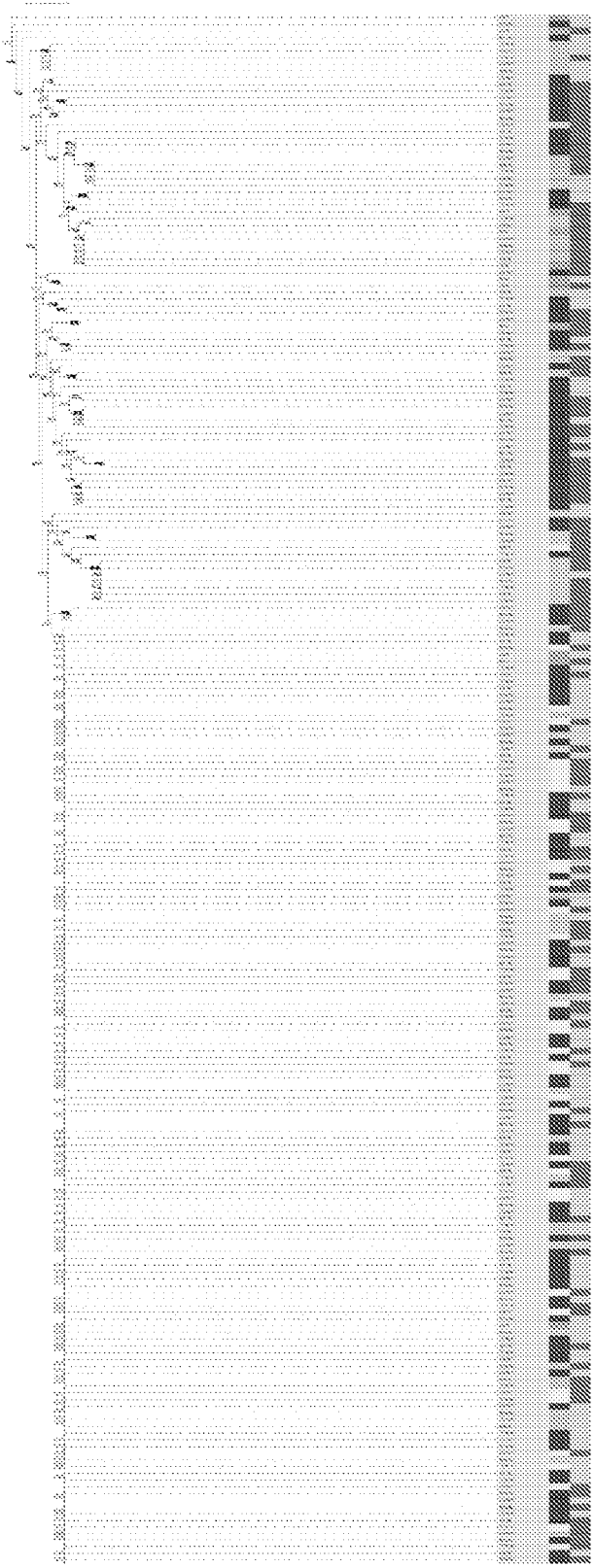
Figure 9C:
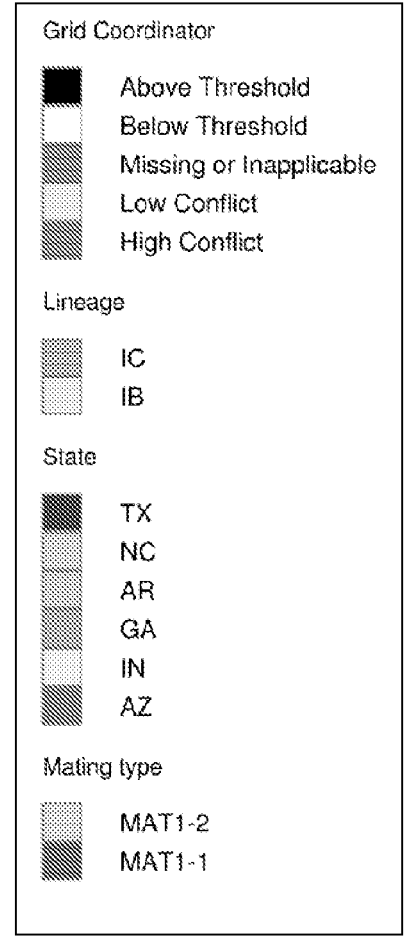
Figure 9D:
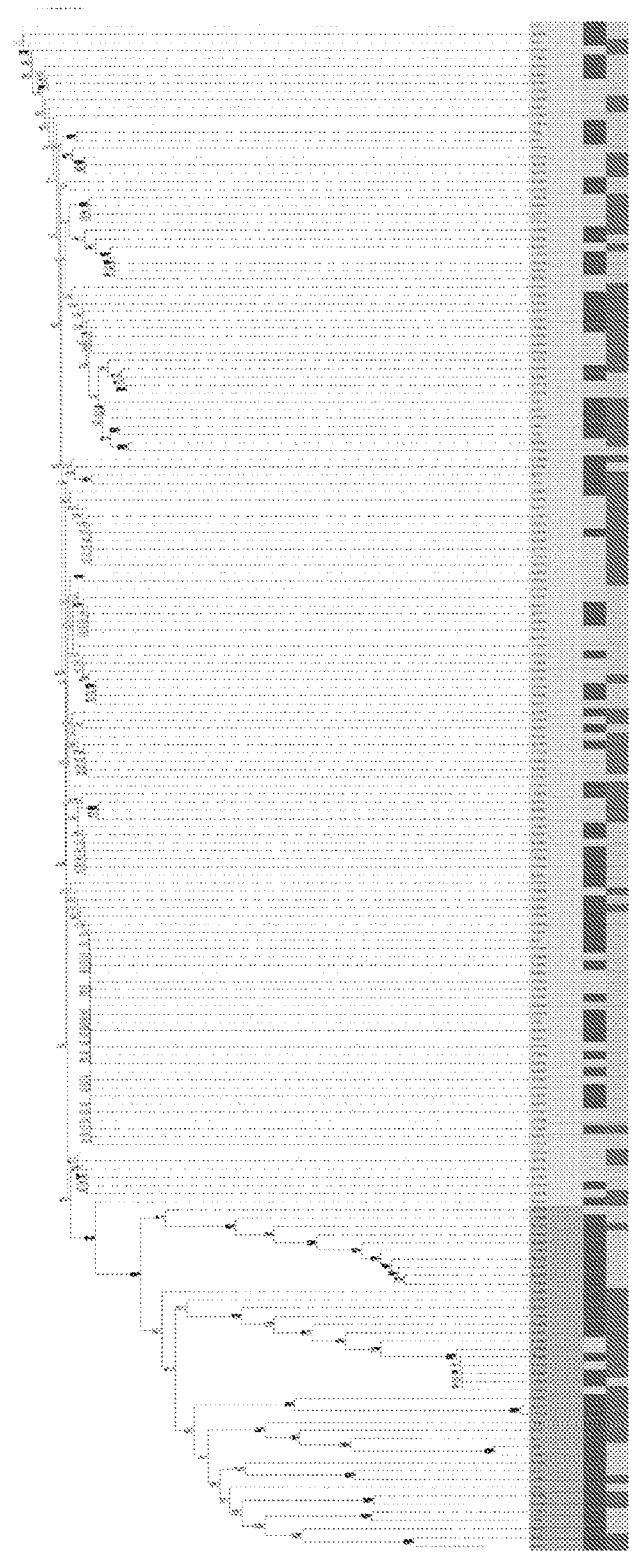
Figure 9D:
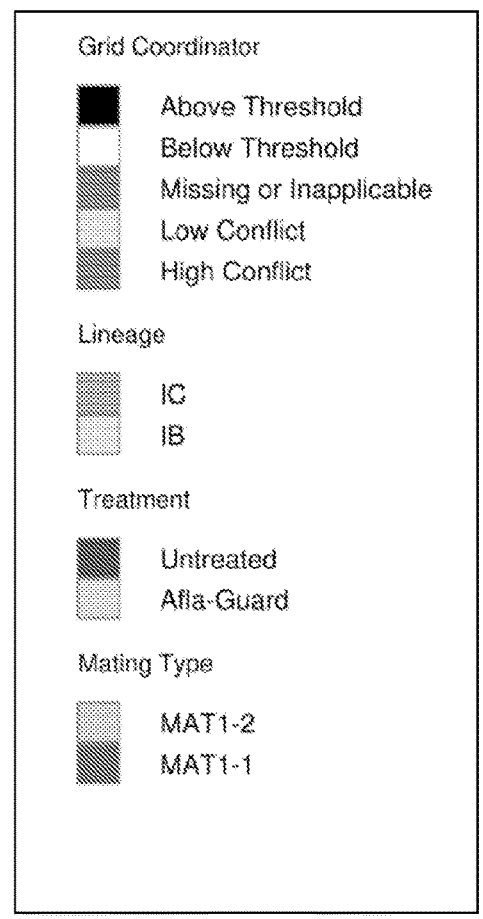
Figure 10A:
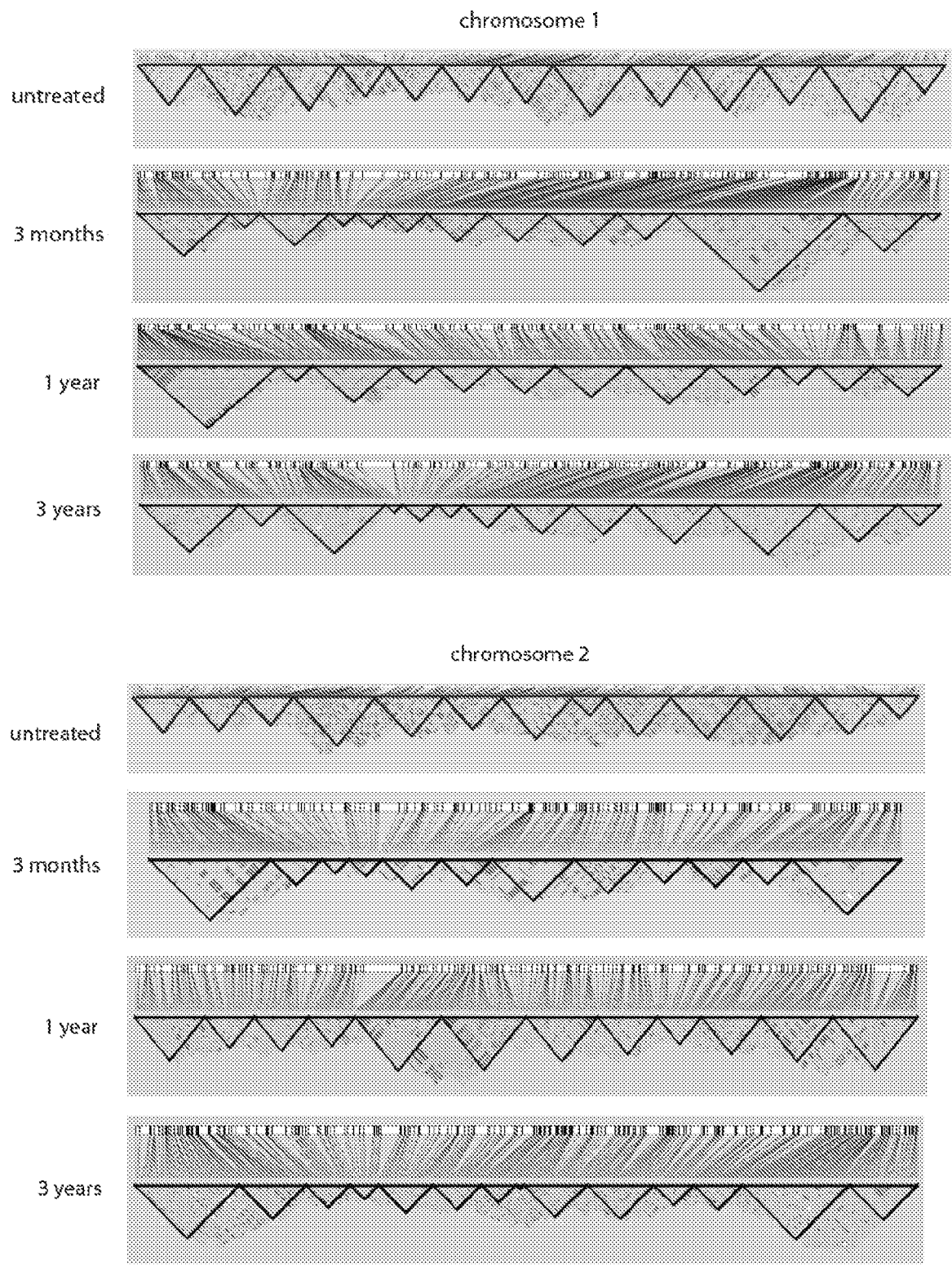
Figure 10B:
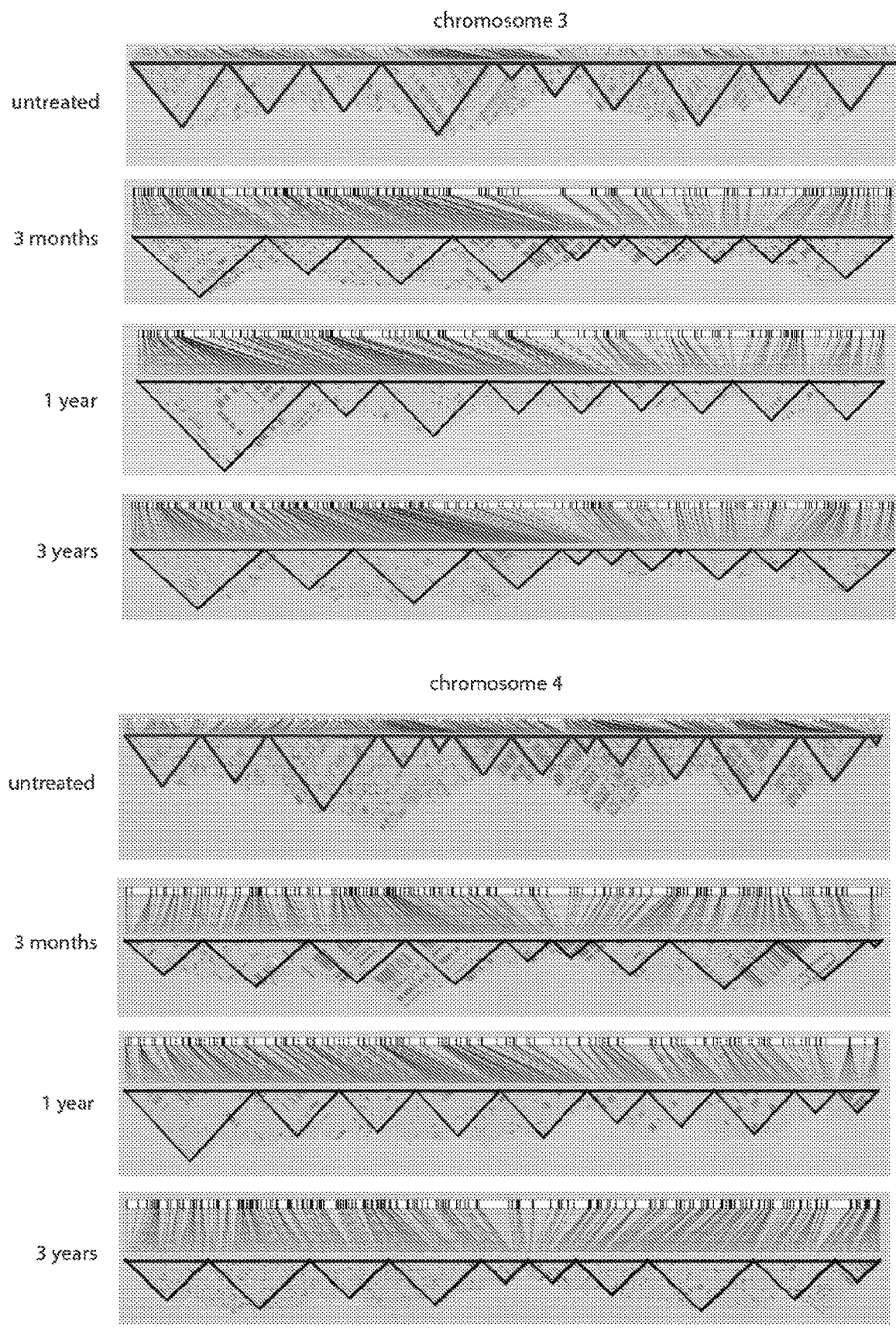
Figure 10C:
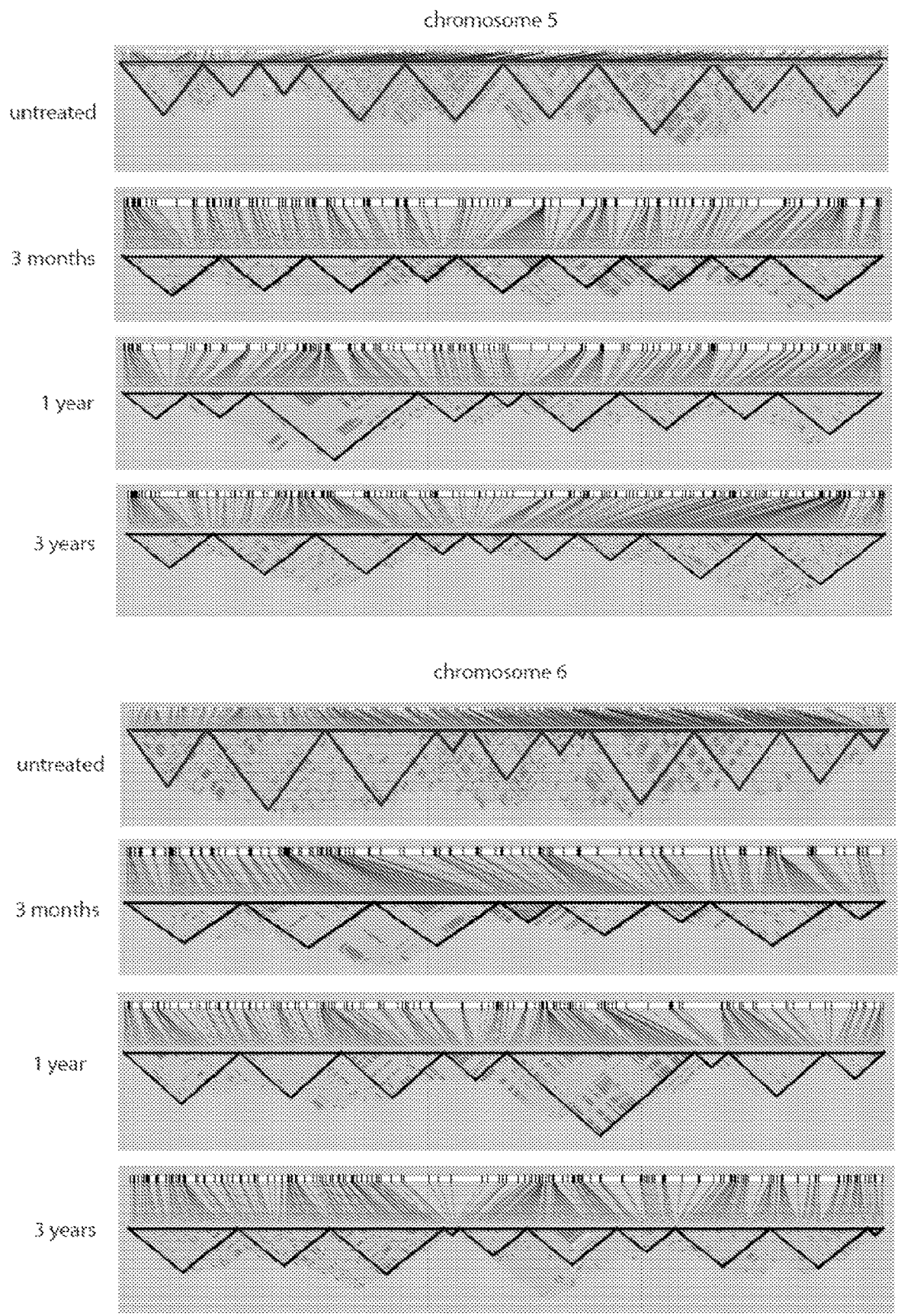
Figure 10D:
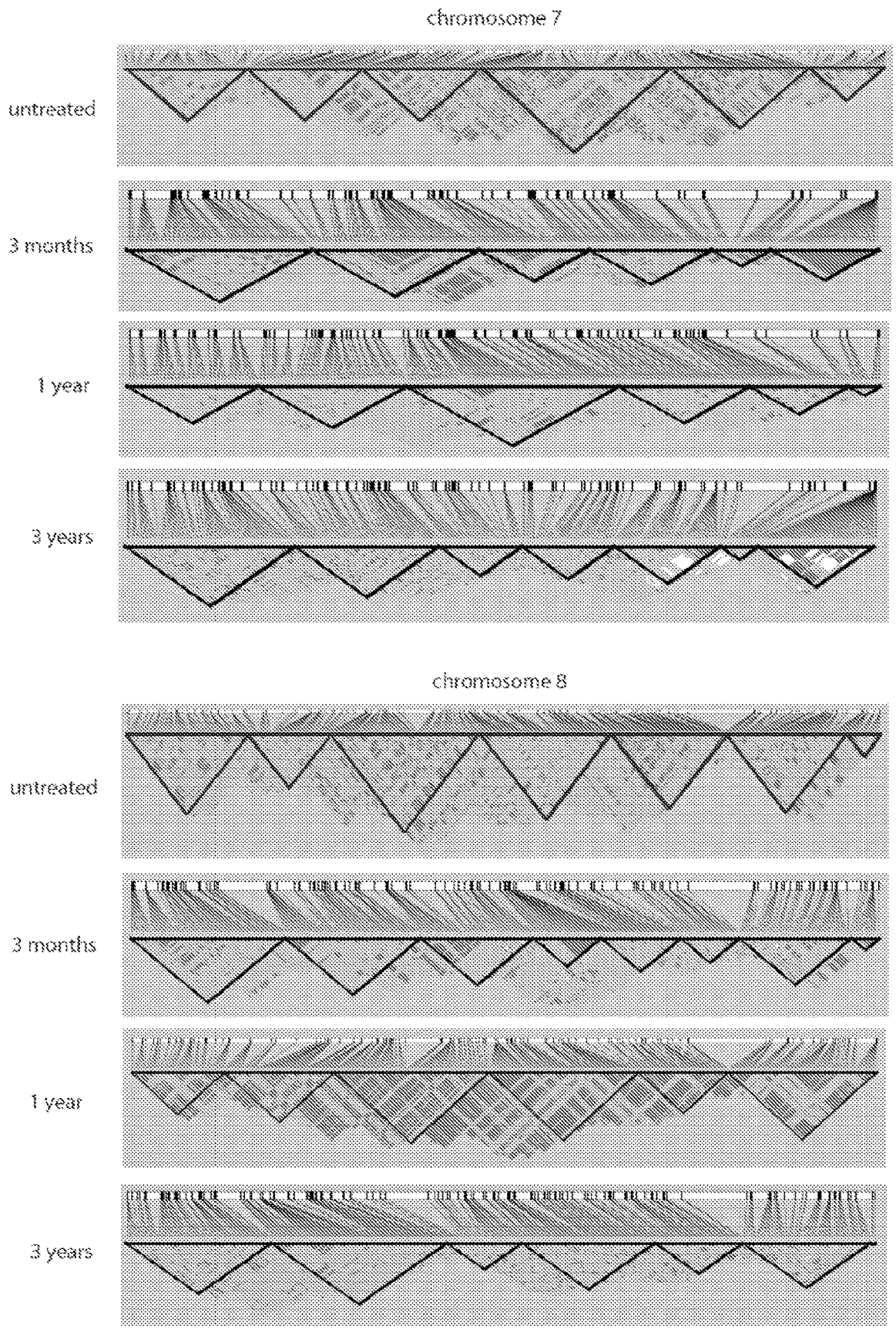

Examination of phylogenetic congruence across chromosomal phylogenies, including the mitochondrial genome, showed evidence of extensive conflict in deep branches and concordance in terminal branches and clades FIGS. 9A-D. As expected, node bipartitions where the descendants were isolates that belonged to the same VCG showed ≥70 bootstrap support or low conflict across most chromosomes. For example, the Afla-Guard® strain (=IC201) which belongs to VCG 24 was widely distributed across TX, IN, NC, AR and GA (IC201 and IC253 reference strains) in the 2013 UTC field plots; two strains out of the 24 within this VCG were MAT1-1 and showed conflict in chromosome 1 of their immediate common ancestor (FIG. 9A). By contrast, the AF36 (=IC1179) which belong to VCG YV36 was recovered only in AR (IC7716).

Although VCGs were grouped together in phylogenies reflecting their common ancestry and close similarity, they showed both recent and past recombination events in their evolutionary histories. For example, recombination was detected in the immediate common ancestor of VCG 17 (IC243, IC244; high conflict in chrs 7, 8) and VCG 6 (IC229, IC230; high conflict in chrs 2, 3) (FIG. 9A; Table 3). Other VCGs were more clonal in their immediate common ancestor such as VCG 5 (IC225, IC226) but there was evidence of recombination one node back, which included strain IC7963. There was high conflict across all chromosomes in the deepest nodes of the 2013 UTC and 2013 TRT phylogenies reflecting a history of extensive recombination giving rise to the sampled strains; clonality (grid nodes with black, blue and white colors) was more distinct in the terminal recently evolved nodes. By contrast, this high conflict in deep nodes was not observed in phylogenies that represented fields sampled 1 year (FIG. 9C) and 3 years (FIG. 9D) after biocontrol application; these fields showed a strong signature of clonality and recombination that was concentrated in terminal nodes. Evidence for the latter was the existence of different mating types for closely related strains or high conflict for at least one chromosome in the immediate ancestor. We used these criteria to count VCGs and identify putative new VCGs that may have evolved in response to released AflaGuard® (=IC201) and AF36 (=IC1179) biocontrol strains (Table 8).

A total of 75 potentially new VCGs that share a recent common ancestor with Afla-Guard® were counted one-year post treatment compared to only 14 that share a common ancestor with AF36. New VCGs were also observed just three months after biocontrols were applied—at least 12 were counted that were similar to the Afla-Guard® strain and four that showed similarity to AF36. In the untreated plots and cornfields in TX that were sampled three years after Afla-Guard® was applied, only 2-3 new VCGs had genetic backgrounds that were similar to Afla-Guard® or AF36.

TABLE 8

VCG counts across treatments and putative descendants of biocontrol strains

| Treatment | Total VCGs | Afla-Guard-like VCGs | AF36-like VCGs |
| --- | --- | --- | --- |
| 2013 UTC | 69 | 2 | 2 |
| 2013 TRT | 39 | 12 | 4 |
| 1 year POST | 218 | 75 | 14 |
| 3 years POST | 57 | 3 | 3 |

Chromosomal Linkage Disequilibrium

Distinct chromosomal LD blocks were inferred across all chromosomes (FIGS. 10A-D). For example, a total of 13 LD blocks were observed for chr 1 across treatments; however, the untreated fields showed the strongest LD. The existence of smaller LD blocks in populations that were sampled 3 months, 1 year and 3 years after biocontrol application indicates ongoing recombination breaking down LD blocks larger; larger LD blocks 1 year after biocontrol application indicates a predominantly clonal population structure as observed in mating type distributions for lineages IB and IC (Table 4). Clonality is also supported by lower estimates of gamma/bp in lineages IB (0.00195) and IC (0.01039) compared to 2013 UTC lineage IB (0.02514) and IC (0.00248) (Table S2).

Aflatoxin Production

Three years after Afla-Guard application, the TX commercial cornfields showed significant clonal expansion in lineage IB with many strains having full AF gene clusters (Table 7), whereas lineage IC strains were found almost exclusively in the untreated plots. Aflatoxin levels measured from corn kernels in these TX fields were consistently low (10-33 ppb). Reference strains showed that $B_1$ concentrations measured from fungal medium were lower for lineage IB strains ($0<\mu g/mL<2$) compared to lineage IC ($0<\mu g/mL<40$) (Table 9). This was also reflected in low B 1 concentrations ($0<\mu g/mL<2$) for full cluster strains in lineage IB in the TX cornfields when compared to $B_1$ levels for lineage IC full cluster strains ($0<\mu g/mL<40$) (Table 6).

TABLE 9

Aflatoxin $B_1$ concentrations of representative *A. flavus* isolates

| IC Number | Location | Lineage | $B_1$ Conc.[1] (µg/mL) | Average AF $B_1$ Conc. (µg/mL) | Relative Standard Deviation (%) |
| --- | --- | --- | --- | --- | --- |
| Reference Isolates | | | | | |
| IC229 | GA | IC | 1.05<br>1.11<br>1.16 | 1.11 | 4.72 |

TABLE 9-continued

Aflatoxin $B_1$ concentrations of representative *A. flavus* isolates

| IC Number | Location | Lineage | $B_1$ Conc.[1] (µg/mL) | Average AF $B_1$ Conc. (µg/mL) | Relative Standard Deviation (%) |
|---|---|---|---|---|---|
| IC278 | GA | IC | 29.57 | 28.76 | 4.25 |
|  |  |  | 27.35 |  |  |
|  |  |  | 29.35 |  |  |
| IC308 | GA | IC | 0.35 | 0.26 | 33.60 |
|  |  |  | 0.20 |  |  |
|  |  |  | 0.21 |  |  |
| IC310 | NC | IC | ND | NA | NA |
|  |  |  | ND |  |  |
|  |  |  | ND |  |  |
| IC1179 | AZ | IC | ND | NA | NA |
|  |  |  | ND |  |  |
|  |  |  | ND |  |  |
| IC201 | — | IB | ND | NA | NA |
|  |  |  | ND |  |  |
|  |  |  | ND |  |  |
| IC218 | GA | IB | 0.41 | 0.30 | 36.26 |
|  |  |  | 0.20 |  |  |
|  |  |  | 0.28 |  |  |
| IC221 | GA | IB | ND | NA | NA |
|  |  |  | ND |  |  |
|  |  |  | ND |  |  |
| IC225 | GA | IB | 0.15 | 0.17 | 62.89 |
|  |  |  | 0.07 |  |  |
|  |  |  | 0.28 |  |  |
| Untreated Isolates | | | | | |
| IC6169 | TX | IC | ND | NA | NA |
|  |  |  | ND |  |  |
|  |  |  | ND |  |  |
| IC6172 | TX | IC | 26.72 | 27.97 | 8.34 |
|  |  |  | 26.53 |  |  |
|  |  |  | 30.67 |  |  |
| IC6508 | NC | IC | ND | NA | NA |
|  |  |  | ND |  |  |
|  |  |  | ND |  |  |
| IC6510 | NC | IC | 1.70 | 0.93 | 117.60 |
|  |  |  | 0.16 |  |  |
|  |  |  | ND |  |  |
| IC6511 | NC | IC | 33.74 | 39.12 | 14.09 |
|  |  |  | 44.76 |  |  |
|  |  |  | 38.88 |  |  |
| IC6540 | NC | IC | 33.70 | 20.61 | 20.44 |
|  |  |  | 39.62 |  |  |
|  |  |  | 50.32 |  |  |
| IC6541 | NC | IC | 54.48 | 54.50 | 8.97 |
|  |  |  | 49.62 |  |  |
|  |  |  | 59.40 |  |  |
| IC7165 | IN | IC | 27.60 | 25.81 | 23.44 |
|  |  |  | 19.07 |  |  |
|  |  |  | 30.76 |  |  |
| IC7645 | AR | IC | 71.80 | 72.78 | 3.54 |
|  |  |  | 70.83 |  |  |
|  |  |  | 75.70 |  |  |
| IC7680 | AR | IC | 38.46 | 39.92 | 4.52 |
|  |  |  | 39.36 |  |  |
|  |  |  | 41.94 |  |  |
| IC7718 | AR | IC | ND | NA | NA |
|  |  |  | ND |  |  |
|  |  |  | ND |  |  |
| IC8216 | NC | IC | 19.69 | 20.62 | 10.51 |
|  |  |  | 19.08 |  |  |
|  |  |  | 23.10 |  |  |
| IC14609 | TX | IC | 1.57 | 1.09 | 39.70 |
|  |  |  | 0.97 |  |  |
|  |  |  | 0.73 |  |  |
| IC14611 | TX | IC | 0.13 | 0.13 | 5.42 |
|  |  |  | ND |  |  |
|  |  |  | 0.14 |  |  |
| IC14613 | TX | IC | 0.59 | 0.65 | 8.88 |
|  |  |  | 0.70 |  |  |
|  |  |  | 0.68 |  |  |
| IC14645 | TX | IC | ND | NA | NA |
|  |  |  | ND |  |  |
|  |  |  | ND |  |  |
| IC14651 | TX | IC | ND | NA | NA |
|  |  |  | ND |  |  |
|  |  |  | ND |  |  |
| IC14674 | TX | IC | 0.15 | 0.14 | 63.35 |
|  |  |  | 0.05 |  |  |
|  |  |  | 0.23 |  |  |
| IC14677 | TX | IC | 0.09 | 0.06 | 64.07 |
|  |  |  | 0.03 |  |  |
|  |  |  | ND |  |  |
| IC14680 | TX | IC | 1.46 | 1.45 | 58.00 |
|  |  |  | 0.60 |  |  |
|  |  |  | 2.28 |  |  |
| IC14683 | TX | IC | 1.37 | 2.82 | 58.26 |
|  |  |  | 2.47 |  |  |
|  |  |  | 4.60 |  |  |
| IC14687 | TX | IC | 0.04 | 0.08 | 56.47 |
|  |  |  | 0.14 |  |  |
|  |  |  | 0.08 |  |  |
| IC14691 | TX | IC | 32.73 | 24.34 | 36.33 |
|  |  |  | 15.10 |  |  |
|  |  |  | 25.18 |  |  |
| IC14693 | TX | IC | 0.25 | 0.44 | 38.80 |
|  |  |  | 0.58 |  |  |
|  |  |  | 0.48 |  |  |
| IC14756 | TX | IC | 49.41 | 33.23 | 42.20 |
|  |  |  | 24.80 |  |  |
|  |  |  | 25.48 |  |  |
| IC14757 | TX | IC | 10.94 | 12.07 | 16.10 |
|  |  |  | 14.31 |  |  |
|  |  |  | 10.96 |  |  |
| IC6353 | TX | IB | ND | NA | NA |
|  |  |  | ND |  |  |
|  |  |  | ND |  |  |
| IC6354 | TX | IB | ND | 0.00 | NA |
|  |  |  | 0.00 |  |  |
|  |  |  | 0.00 |  |  |
| IC6358 | TX | IB | ND | NA | NA |
|  |  |  | ND |  |  |
|  |  |  | ND |  |  |
| IC6512 | NC | IB | 0.72 | 1.99 | 55.45 |
|  |  |  | 2.72 |  |  |
|  |  |  | 2.54 |  |  |
| IC6542 | TX | IB | 0.03 | 0.03 | 4.33 |
|  |  |  | 0.03 |  |  |
|  |  |  | 0.03 |  |  |
| IC6866 | IN | IB | 0.02 | 0.57 | 161.21 |
|  |  |  | 0.06 |  |  |
|  |  |  | 1.62 |  |  |
| IC7084 | IN | IB | 0.00 | 0.05 | 118.55 |
|  |  |  | 0.12 |  |  |
|  |  |  | 0.03 |  |  |
| IC7854 | TX | IB | ND | NA | NA |
|  |  |  | ND |  |  |
|  |  |  | ND |  |  |
| IC7855 | TX | IB | 0.01 | 0.01 | 69.63 |
|  |  |  | 0.01 |  |  |
|  |  |  | 0.02 |  |  |
| IC7865 | TX | IB | 0.02 | 0.19 | 81.87 |
|  |  |  | 0.31 |  |  |
|  |  |  | 0.24 |  |  |
| IC7961 | TX | IB | 0.18 | 0.19 | 2.55 |
|  |  |  | 0.19 |  |  |
|  |  |  | 0.19 |  |  |
| IC14618 | TX | IB | 0.50 | 0.23 | 99.73 |
|  |  |  | 0.11 |  |  |
|  |  |  | 0.09 |  |  |
| IC14649 | TX | IB | 0.02 | 0.02 | 2.67 |
|  |  |  | 0.02 |  |  |
|  |  |  | 0.02 |  |  |

TABLE 9-continued

Aflatoxin B₁ concentrations of representative *A. flavus* isolates

| IC Number | Location | Lineage | B₁ Conc.[1] (µg/mL) | Average AF B₁ Conc. (µg/mL) | Relative Standard Deviation (%) |
|---|---|---|---|---|---|
| IC14650 | TX | IB | 0.06 | 0.10 | 98.05 |
|  |  |  | 0.22 |  |  |
|  |  |  | 0.03 |  |  |
| IC14658 | TX | IB | 0.02 | 0.02 | 5.88 |
|  |  |  | 0.02 |  |  |
|  |  |  | 0.03 |  |  |
| IC14661 | TX | IB | ND | NA | NA |
|  |  |  | ND |  |  |
|  |  |  | ND |  |  |
| IC14664 | TX | IB | 0.02 | 0.02 | 6.89 |
|  |  |  | 0.02 |  |  |
|  |  |  | 0.03 |  |  |
| IC14676 | TX | IB | ND | NA | NA |
|  |  |  | ND |  |  |
|  |  |  | ND |  |  |
| IC14684 | TX | IB | ND | NA | NA |
|  |  |  | ND |  |  |
|  |  |  | ND |  |  |
| IC14688 | TX | IB | ND | NA | NA |
|  |  |  | ND |  |  |
|  |  |  | ND |  |  |
| IC14753 | TX | IB | 0.44 | 0.51 | 12.87 |
|  |  |  | 0.51 |  |  |
|  |  |  | 0.57 |  |  |
|  |  |  | ND |  |  |
| 3 months |
| IC6314 | TX | IC | ND | NA | NA |
|  |  |  | ND |  |  |
| IC6321 | TX | IC | ND | NA | NA |
|  |  |  | ND |  |  |
|  |  |  | ND |  |  |
| IC6348 | TX | IC | 0.39 | 0.42 | 31.97 |
|  |  |  | 0.30 |  |  |
|  |  |  | 0.56 |  |  |
| IC8098 | NC | IC | 45.47 | 40.73 | 13.56 |
|  |  |  | 34.67 |  |  |
|  |  |  | 42.07 |  |  |
| IC8101 | TX | IC | 20.40 | 13.56 | 43.73 |
|  |  |  | 10.07 |  |  |
|  |  |  | 10.20 |  |  |
| IC6338 | TX | IB | 0.13 | 0.09 | 47.69 |
|  |  |  | 0.11 |  |  |
|  |  |  | 0.04 |  |  |
| IC6340 | TX | IB | ND | NA | NA |
|  |  |  | ND |  |  |
|  |  |  | ND |  |  |
| IC6346 | TX | IB | ND | NA | NA |
|  |  |  | ND |  |  |
|  |  |  | ND |  |  |
| IC8097 | TX | IB | 0.03 | 0.04 | 46.48 |
|  |  |  | 0.05 |  |  |
|  |  |  | 0.02 |  |  |
| IC10098 | IN | IB | ND | NA | NA |
|  |  |  | ND |  |  |
|  |  |  | ND |  |  |
| 1 year |
| IC11306 | TX | IC | ND | NA | NA |
|  |  |  | ND |  |  |
|  |  |  | ND |  |  |
| IC13042 | TX | IC | 53.13 | 55.16 | 3.18 |
|  |  |  | 56.20 |  |  |
|  |  |  | 56.13 |  |  |
| IC13878 | NC | IC | 19.99 | 23.38 | 14.26 |
|  |  |  | 26.65 |  |  |
|  |  |  | 23.50 |  |  |
| IC14034 | NC | IC | ND | 137.53 | 68.07 |
|  |  |  | 71.33 |  |  |
|  |  |  | 203.73 |  |  |
| IC14794 | TX | IC | ND | NA | NA |
|  |  |  | ND |  |  |
|  |  |  | ND |  |  |
| IC15700 | IN | IC | 48.83 | 61.48 | 41.00 |
|  |  |  | 45.10 |  |  |
|  |  |  | 90.50 |  |  |
| IC15706 | IN | IC | 0.01 | 0.01 | 28.64 |
|  |  |  | 0.01 |  |  |
|  |  |  | 0.01 |  |  |
| IC15720 | IN | IC | ND | NA | NA |
|  |  |  | ND |  |  |
|  |  |  | ND |  |  |
| IC15721 | IN | IC | ND | NA | NA |
|  |  |  | ND |  |  |
|  |  |  | ND |  |  |
| IC16033 | NC | IC | 58.73 | 48.80 | 25.61 |
|  |  |  | 52.90 |  |  |
|  |  |  | 34.77 |  |  |
| IC16148 | NC | IC | ND | 0.68 | 64.40 |
|  |  |  | 0.99 |  |  |
|  |  |  | 0.37 |  |  |
| IC18128 | AR | IC | 179.20 | 141.62 | 34.49 |
|  |  |  | 86.40 |  |  |
|  |  |  | 159.27 |  |  |
| IC11271 | TX | IB | 0.11 | 0.30 | 53.71 |
|  |  |  | 0.40 |  |  |
|  |  |  | 0.38 |  |  |
| IC11548 | TX | IB | 1.31 | 0.89 | 84.65 |
|  |  |  | 0.02 |  |  |
|  |  |  | 1.33 |  |  |
| IC13049 | TX | IB | 3.04 | 1.46 | 97.61 |
|  |  |  | 1.10 |  |  |
|  |  |  | 0.25 |  |  |
| IC13154 | TX | IB | 0.95 | 1.50 | 90.51 |
|  |  |  | 3.05 |  |  |
|  |  |  | 0.50 |  |  |
| IC15711 | IN | IB | 3.58 | 2.79 | 75.89 |
|  |  |  | 4.41 |  |  |
|  |  |  | 0.39 |  |  |
| IC16302 | NC | IB | 0.05 | 0.03 | 45.16 |
|  |  |  | 0.02 |  |  |
|  |  |  | 0.03 |  |  |
| IC18299 | AR | IB | 0.91 | 0.48 | 89.86 |
|  |  |  | 0.04 |  |  |
|  |  |  | 0.51 |  |  |
| 3 years |
| IC14609 | TX | IC | 1.57 | 1.09 | 39.70 |
|  |  |  | 0.97 |  |  |
|  |  |  | 0.73 |  |  |
| IC14611 | TX | IC | 0.13 | 0.13 | 5.42 |
|  |  |  | ND |  |  |
|  |  |  | 0.14 |  |  |
| IC14613 | TX | IC | 0.59 | 0.65 | 8.88 |
|  |  |  | 0.70 |  |  |
|  |  |  | 0.68 |  |  |
| IC14645 | TX | IC | ND | NA | NA |
|  |  |  | ND |  |  |
|  |  |  | ND |  |  |
| IC14651 | TX | IC | ND | NA | NA |
|  |  |  | ND |  |  |
|  |  |  | ND |  |  |
| IC14674 | TX | IC | 0.15 | 0.14 | 63.35 |
|  |  |  | 0.05 |  |  |
|  |  |  | 0.23 |  |  |
| IC14677 | TX | IC | 0.09 | 0.06 | 64.07 |
|  |  |  | 0.03 |  |  |
|  |  |  | ND |  |  |
| IC14680 | TX | IC | 1.46 | 1.45 | 58.00 |
|  |  |  | 0.60 |  |  |
|  |  |  | 2.28 |  |  |
| IC14683 | TX | IC | 1.37 | 2.82 | 58.26 |
|  |  |  | 2.47 |  |  |
|  |  |  | 4.60 |  |  |

TABLE 9-continued

Aflatoxin $B_1$ concentrations of representative *A. flavus* isolates

| IC Number | Location | Lineage | $B_1$ Conc.[1] (µg/mL) | Average AF $B_1$ Conc. (µg/mL) | Relative Standard Deviation (%) |
|---|---|---|---|---|---|
| IC14687 | TX | IC | 0.04<br>0.14<br>0.08 | 0.08 | 56.47 |
| IC14691 | TX | IC | 32.73<br>15.10<br>25.18 | 24.34 | 36.33 |
| IC14693 | TX | IC | 0.25<br>0.58<br>0.48 | 0.44 | 38.80 |
| IC14722 | TX | IC | 28.31<br>30.06<br>22.97 | 27.11 | 13.62 |
| IC14756 | TX | IC | 49.41<br>24.80<br>25.48 | 33.23 | 42.20 |
| IC14757 | TX | IC | 10.94<br>14.31<br>10.96 | 12.07 | 16.10 |
| IC14770 | TX | IC | 24.78<br>15.80<br>21.89 | 20.82 | 22.01 |
| IC14618 | TX | IB | 0.50<br>0.11<br>0.09 | 0.23 | 99.73 |
| IC14631 | TX | IB | 0.00<br>0.01<br>0.08 | 0.03 | 140.70 |
| IC14638 | TX | IB | 0.02<br>0.01<br>0.03 | 0.02 | 43.71 |
| IC14649 | TX | IB | 0.02<br>0.02<br>0.02 | 0.02 | 2.67 |
| IC14650 | TX | IB | 0.06<br>0.22<br>0.03 | 0.10 | 98.05 |
| IC14658 | TX | IB | 0.02<br>0.02<br>0.03 | 0.02 | 5.88 |
| IC14661 | TX | IB | ND<br>ND<br>ND | NA | NA |
| IC14664 | TX | IB | 0.02<br>0.02<br>0.03 | 0.02 | 6.89 |
| IC14676 | TX | IB | ND<br>ND<br>ND | NA | NA |
| IC14684 | TX | IB | ND<br>ND<br>ND | NA | NA |
| IC14688 | TX | IB | ND<br>ND<br>ND | NA | NA |
| IC14697 | TX | IB | 0.00<br>0.00<br>0.06 | 0.02 | 150.01 |
| IC14707 | TX | IB | 0.49<br>0.05<br>0.09 | 0.21 | 115.17 |
| IC14713 | TX | IB | ND<br>ND<br>ND | NA | NA |
| IC14721 | TX | IB | ND<br>ND<br>ND | NA | NA |
| IC14725 | TX | IB | 0.09<br>0.06<br>0.04 | 0.06 | 40.17 |
| IC14728 | TX | IB | 0.22<br>0.24<br>0.48 | 0.31 | 46.39 |
| IC14744 | TX | IB | 0.23<br>0.03<br>0.10 | 0.12 | 86.60 |
| IC14745 | TX | IB | ND<br>ND<br>ND | NA | NA |
| IC14768 | TX | IB | ND<br>ND<br>ND | NA | NA |
| IC14769 | TX | IB | 0.13<br>0.07<br>0.27 | 0.16 | 64.24 |

ND, not detected; NA not applicable

[1]The aflatoxin concentrations obtained from HPLC correspond to the 1 mL of methanol in which dried aflatoxin samples are resuspended. This only contains the amount of aflatoxins within 0.5 mL of the chloroform, which is half of the initial 1.0 mL of chloroform introduced to each sample. To represent the aflatoxin concentration within 1.0 mL of culture, the concentrations reported were obtained by doubling each concentration initially conveyed by HPLC results to factor in the previous halving of that concentration.

Discussion

Previous work has shown that populations with an approximately equal distribution of MAT1-1 and MAT1-2 mating types have a greater potential for aflatoxin production because of the high heritability of aflatoxin clusters (Olarte et al. 2012); therefore, the relative proportion of MAT1-1 and MAT1-2 isolates in a population is a useful predictor of the amount of sexual recombination within a field, which may directly or indirectly influence aflatoxin production. Currently, the two approved *A. flavus* biocontrols are of the same mating type (MAT1-2) but belong to different evolutionary lineages; Afla-Guard® is in lineage IB and AF36 belongs to lineage IC. In field experiments where the *A. flavus* Afla-Guard® and AF36 strains were applied separately to replicated plots, and compared to untreated plots, both lineages IB and IC were recovered from corn kernels three months and one year after initial application. Prior to the application of biocontrol agents both lineages were present in untreated plots and clone-corrected MAT1-1:MAT1-2 ratio did not differ significantly from 1 in TX and NC, which indicates regular sexual reproduction in these states (Table 6). Mating type ratios within lineages IB and IC were also close to 1:1 (Table 7), which shows that sexual reproduction is an important component in the biology of *A. flavus* that transcends state boundaries.

One year after biocontrol application, treated plots in TX and NC were significantly skewed to MAT1-1 (Table 6); MAT distributions in lineages IB and IC were also similarly skewed (Table 7). Because both biocontrols are MAT1-2, successful mating would be predominantly between a MAT1-2 biocontrol stain and different MAT1-1 native strains. This results in many new VCGs that have a similar genetic background to either Afla-Guard® or AF36 but are MA. T1-1 (Table 8). Similarly, untreated populations in AR and IN had a significant clonal component even after clone correction. The skew to MAT1-1 in these populations increased opportunities for mating with MAT1-2 biocontrol strains. This is apparent in AR and IN in their progression from MAT1-1 in the untreated fields, to MAT1-2 predominating 3 months after treatment, and finally MAT1-1:MAT1-2 ratios not deviating significantly from 1 one year later. Results from the commercial TX cornfields indicate that populations eventually return to equilibrium in the ratio of MAT1-1: MAT1-2 after more generations. So, while non-aflatoxigenic biocontrol agents have their initial intended action of reducing aflatoxin levels, one year later the populations have recombined and comprise both lineages IB (mostly nontoxigenic) and IC (mostly toxigenic), making it necessary to reapply biocontrols.

In TX fields where aflatoxin levels were consistently low over several years, there was a larger proportion of lineage IB isolates compared to IC and there was clear evidence of admixture among lineage IB isolates, both from the approximately 1:1 distribution of MAT1-1:MAT1-2 and from structure analysis showing that lineage IB in TX was one large randomly mating population. Mechanistically, the reduction in aflatoxin levels may be driven by clonal amplification and genetic admixture. Although both the Afla-Guard® strain and AF36 are effective in reducing aflatoxin levels in the short term, their efficacy in the long-term may depend on which lineage they belong to. Because lineage IB isolates are predominantly atoxigenic, populations with a greater proportion of lineage IB strains relative to lineage IC are predicted to have reduced aflatoxin levels. It follows that biocontrol formulations that include strains of opposite mating type that belong to lineage IB could result in a higher frequency of mating interactions between lineage IB and native strains.

The disproportionate mating access of lineage IB strains to female strains of high fertility in lineage IC would result in unequal introgression of the lineage IB genetic background in field populations that are treated with biocontrol compositions comprising both mating types. This then results in a larger proportion of lineage IB strains in the population that are non-aflatoxigenic or low aflatoxin producers such that the net effect is a lowering of aflatoxin levels in field populations. This could explain the lower aflatoxin levels observed in the TX commercial cornfields. Although the TX commercial cornfields are predominantly lineage IB genetically, they are functionally a mix of aflatoxin-producing and non-aflatoxin producing strains. Any balancing selection acting to maintain aflatoxin producers and non-producers in the population can continue but the targets of selection are now predominantly low aflatoxin producers within lineage IB. In the absence of the low aflatoxin producing full cluster strains in lineage IB, we predict selection would be acting predominantly on high toxin producing strains in lineage IC and non-producers in IB. This suggests that it might be possible to shift *A. flavus* populations to a state that is functionally and qualitatively similar to the native population but quantitatively have a much-reduced aflatoxin footprint than the native population. This has significantly implications for reducing aflatoxin contamination worldwide.

From a biocontrol perspective, the enhanced introgression of sexually compatible lineage IB strains into native populations offers the potential for sustained reductions in aflatoxin levels over subsequent generations. Preliminary field results of biocontrol formulations containing a mix of sexually compatible strains in NC and TX show that they potentially outperform single strain formations; more sampling over several years should show if mixtures of compatible mating partners continue to lower aflatoxin levels and if they also influence corn yields. Both *A. flavus* evolutionary lineages (IB and IC) are widely dispersed along a latitude gradient and transcend state boundaries. Thus, it may be possible for a single biocontrol formulation to be effective across different latitudes and environmental conditions. For example, the Afla-Guard® strain has been shown to be effective in mitigating aflatoxin contamination in Texas (Domer 2010; Isakeit 2015) and North Carolina (Meyers et al. 2015; Molo et al. 2018). Under field conditions, mating success is dependent upon genetic diversity in soil populations, thus selecting a mix of strains from lineage IB that are of different mating types and clonal backgrounds may be a useful strategy for mitigating aflatoxin contamination. Moreover, the same strain mixtures may be effective for different fields because the evolutionary lineage effect may be stronger than strain-specific differences in reducing aflatoxin levels. For example, incorporating a complementary MAT1-1 strain from lineage IB into the Afla-Guard® formulation may improve the efficacy including long term effectiveness of biocontrol, particularly in fields that harbor highly fertile strains of both mating types. Such a genetically based biocontrol strategy has the potential to sustainably reduce the aflatoxin producing potential of this agriculturally important fungus.

REFERENCES

Abbas H K, Zablotowicz R M, Horn B W, Phillips N A, Johnson B J, Jin X, & Abel C A. 2011. Comparison of major biocontrol strains of non-aflatoxigenic *Aspergillus flavus* for the reduction of aflatoxins and cyclopiazonic acid in maize. *Food additives and contaminants. Part A, Chemistry, analysis, control, exposure & risk assessment* 28(2):198-208. doi: 10/1080/19440049.2010.544680. Epub 2011 Jan. 20.

Accinelli, C., H. K. Abbas, N. S. Little, J. K. Kotowicz, M. Mencarelli, and W. T. Shier. 2016a. A liquid bioplastic formulation for film coating of agronomic seeds. Crop Prot. 89:123-128. doi:10.1016/j. cropro.2016.07.010.

Accinelli, C., H. K. Abbas, A. Vicari, and W. T. Shier. 2016b. Leaf application of a sprayable bioplastic-based formulation of biocontrol *Aspergillus flavus* strains for reduction of aflatoxins in corn. *Pest Manag. Sci.* 72:1521-1528. doi:10.1002/ps.4180.

Bhat, R., R. V. R. R. Vittal, and A. A. Karim. 2010. Mycotoxins in Food and Feed: Current Status and Future Concerns. Compr. Rev. Food Sci. Food Saf. 9:57-81. doi:10.1111/j.1541-4337.2009.00094.x.

Buels R, Yao E, Diesh C M, et al. (2016) JBrowse: a dynamic web platform for genome visualization and analysis. *Genome Biology* 17, 66.

Burdock G A and Flamm W G. 2000. Review Article: Safety Assessment of the Mycotoxin Cyclopiazonic Acid. *International Journal of Toxicology* 19(3):195-218.

Calvo, A. M., R. A. Wilson, J. W. Bok, and N. P. Keller. 2002. Relationship between secondary metabolism and fungal development. *Microbiol. Mol. Biol. Rev.* 66:447-459. doi:10.1128/MMBR.66.3.447-459.2002.

Carbone I, Ramirez-Prado J H, Jakobek J L, Horn B W (2007) Gene duplication, modularity and adaptation in the evolution of the aflatoxin gene cluster. *BMC Evol. Biol.* 7, 111.

Carbone I, White J B, Miadlikowska J, et al. (2017) T-BAS: Tree-Based Alignment Selector toolkit for phylogenetic-based placement, alignment downloads and metadata visualization: an example with the Pezizomycotina tree of life. *Bioinformatics* 33, 1160-1168.

CDC. 2004. Outbreak of aflatoxin poisoning—eastern and central provinces, Kenya, January-July 2004. MMWR Morb. Mortal. Wkly. Rep. 53(34):790-793.

Chan-Hon-Tong, A., M. A. Charles, A. Forhan, B. Heude, and V. Sirot. 2013. Exposure to food contaminants during pregnancy. Sci. Total Environ. 458-460:27-35. doi: 10.1016/j.scitotenv.2013.03.100.
Chang P-K, Horn B W, Dorner J W (2005) Sequence breakpoints in the aflatoxin biosynthesis gene cluster and flanking regions in nonaflatoxigenic *Aspergillus flavus* isolates. *Fungal Genet Biol* 42, 914-923.
Chen, Z. Y. 2015. Discovery and confirmation of genes/proteins associated with maize aflatoxin resistance. World mycotoxin journal v. 8:p. 211-224-2015 v.2018 no. 2012. doi:10.3920/WMJ2014.1732.
Cotty, P. J. 2006. Biocompetitive exclusion of toxigenic fungi. In: D. Barug, D. Bhatnagar, H. P. Van Egdmond, J. W. Van der Kamp, W. A. Van Osenbruggen, and A. Visconti, editors, The mycotoxin factbook. Wageningen Academic Publishers, Wageningen, the Netherlands.
Cotty, P. J., L. Antilla, and P. J. Wakelyn. 2007. Competitive exclusion of aflatoxin producers: Farmer driven research and development. In: C. Vincent, N. Goettel, and G. Lazarovits, editors, Biological control: A global perspective. CAB International, Wallingford, UK. doi:10.1079/9781845932657.0241.
Cotty, P. J., and P. Bayman. 1993. Competitive exclusion of a toxigenic strain of *Aspergillus flavus* by an atoxigenic strain. Phytopathology 83:1283-1287. doi:10.1094/Phyto-83-1283.
Cotty P J, Bhatnagar D (1994) Variability among atoxigenic *Aspergillus flavus* strains in ability to prevent aflatoxin contamination and production of aflatoxin biosynthetic pathway enzymes. *Appl Environ Microbiol* 60, 2248-2251.
DePristo MA, Banks E, Poplin R, et al. (2011) A framework for variation discovery and genotyping using next-generation DNA sequencing data. *Nat Genet* 43, 491-498.
Dorner, J W (2004) Biological control of aflatoxin contamination of crops. J Toxicol Toxin Rev 23(2&3):425-450.
Dorner J W (2005) Biological control of aflatoxin crop contamination. In: Aflatoxin and Food
Safety (ed. Abbas H K), pp. 333-352. Taylor and Francis, Boca Raton, Florida.
Dorner, J. W., and M. C. Lamb. 2006. Development and commercial use of afla-Guard®, an aflatoxin biocontrol agent. Mycotoxin Res. 22:33-38. doi:10.1007/BF02954555.
Dorner, J W (2008) Management and prevention of mycotoxins in peanuts. Food Addit Contam 25(2):203-208. doi: 10.1080/02652030701658357.
Dorner J W (2010) Efficacy of a Biopesticide for Control of Aflatoxins in Corn. *Journal of food protection* 73, 495-499.
Doster, M. A., P. J. Cotty, and T. J. Michailides. 2014. Evaluation of the atoxigenic *Aspergillus flavus* strain AF36 in pistachio orchards. *Plant Dis.* 98:948-956. doi: 10.1094/PDIS-10-13-1053-R E.
Drott, M. T., B. P. Lazzaro, D. L. Brown, I. Carbone, and M. G. Milgroom. 2017. Balancing selection for aflatoxin in *Aspergillus flavus* is maintained through interference competition with, and fungivory by insects. Proc. Biol. Sci. 284. doi:10.1098/rspb. 2017.2408.
Ehrlich K C, Cotty P J (2004) An isolate of *Aspergillus flavus* used to reduce aflatoxin contamination in cottonseed has a defective polyketide synthase gene. *Applied Microbiology and Biotechnology* 65, 473-478.
FDA. 2011. FDA Regulatory Guidance, A Guide for Grain Elevators, Feed Manufacturers, Grain Processors, and Exporters," National Grain and Feed Association, August 2011.
FDA. 2009. *CPG Sec.* 683.100 *Action Levels for Aflatoxins in Animal Feed*. Accessed Jun. 28, 2016. See, fda.gov/ICECI/ComplianceManuals/CompliancePolicyGuidanceManual/ucm074703.htm.
Geiser, D. M., J. W. Dorner, B. W. Horn, and J. W. Taylor. 2000. The phylogenetics of mycotoxin and *sclerotium* production in *Aspergillus flavus* and *Aspergillus oryzae*. *Fungal Genet. Biol.* 31:169-179. doi:10.1006/fgbi.2000.1215.
Horn B W, Greene R L (1995) Vegetative compatibility within populations of *Aspergillus flavus, Aspergillus parasiticus*, and *A. tamarii* from a peanut field. *Mycologia* 87, 324-332.
Horn B W, Moore G G, Carbone I. 2009. Sexual reproduction in *Aspergillus flavus*. Mycologia 101(3):423-429. doi: 10.3852/09-011.
Horn B W, Sorensen R B, Lamb M C, Sobolev V S, Olarte R A, Worthington C J, & Carbone I. 2014. Sexual Reproduction in *Aspergillus flavus* Sclerotia Naturally Produced Corn. *Phytopathology* 104(1):75-85.
Horn, B. W., R. M. Gell, R. Singh, R. B. Sorensen, and I. Carbone. 2016. Sexual reproduction in *Aspergillus flavus* sclerotia: Acquisition of novel alleles from soil populations and uniparental mitochondrial inheritance. PLoS One 11:e0146169. doi:10.1371/journal.pone.0146169
Huang, C., A. Jha, R. Sweany, C. DeRobertis, and K. E. Damann, Jr. 2011. Intraspecific aflatoxin inhibition in *Aspergillus flavus* is thigmoregulated, independent of vegetative compatibility group and is strain dependent. *PLoS One* 6:e23470. doi:10.1371/journal.pone.0023470.
Huang A, Elmashni D (2007) Analysis of Aflatoxins Using Fluorescence Detection. Thermo Fisher Scientific, Inc.
IARC. 2002. IARC Working Group on the Evaluation of Carcinogenic Risk to Humans. Some Traditional Herbal Medicines, Some Mycotoxins, Naphthalene and Styrene. Lyon (FR): International Agency for Research on Cancer; 2002. (IARC Monographs on the Evaluation of Carcinogenic Risks to Humans, No. 82.) https://wvvvv.ncbi.nlm-.nih.gov/books/NBK326619/.
Isakeit T (2015) Evaluation of atoxigenic strains of *Aspergillus flavus* for aflatoxin control in corn on commercial farms in Texas—2015. *Texas A&M AgriLife Extension*.
Kucharik, C. J., and N. Ramankutty. 2005. Trends and Variability in U.S. Corn Yields Over the Twentieth Century. Earth Interact. 9:1-29. doi:10.1175/EI098.1 Leslie J F (1993) Fungal vegetative compatibility. *Annual Review of Phytopathology* 31, 127-150.
Liu, Y., and F. Wu. 2010. Global burden of aflatoxin-induced hepatocellular carcinoma: A risk assessment. Environ. Health Perspect. 118:818-824. doi:10.1289/ehp.0901388.
Meyers M, Heiniger R, Boerema L, Carbone I (2015) The Use of Management Practices to Reduce Mycotoxin Contamination in Corn. In: AG-807. NC State Extension, Raleigh, NC.
Miller M A, Schwartz T, Pickett B E, et al. (2015) *A RESTful API for Access to Phylogenetic* Tools via the CIPRES Science Gateway. *Evolutionary Bioinformatics Online* 11, 43-48.
Mitchell, N. J., E. Bowers, C. Hurburgh, and F. Wu. 2016. Potential economic losses to the USA corn industry from aflatoxin contamination. Food Addit. Contam. Part A Chem. Anal. Control Expo. Risk Assess. 33:540-550. doi:10.1080/19440049.2016.1138545.
Molo M, Heiniger R, Boerema L, Carbone I (2018) Management Practices for Controlling Mycotoxins in Corn: A Three-Year Summary. In: AG-852. N C State Extension, Raleigh, N C.

Monacell J T (2014) Identification of heterokaryon incompatibility genes in *Aspergillus* using array comparative genome hybridization and whole genome sequencing. Ph.D. Thesis, North Carolina State University.

Moore, G. G., R. Singh, B. W. Horn, and I. Carbone. 2009. Recombination and lineage-specific gene loss in the aflatoxin gene cluster of *Aspergillus flavus*. Mol. Ecol. 18:4870-4887. doi:10.1111/j.1365-294X.2009.04414.x.

Moore G G, Elliot J L, Singh R, Horn B W, Dorner J W, Stone E A, Chulze S N, Barros G G, Naik M K, Wright G C, Hell K, & Carbone I. 2013. Sexuality Generates Diversity in the Aflatoxin Gene Cluster: Evidence on a Global Scale. *PLoS Pathogens* 9(8):e1003574. doi: 10.1371/journal.ppat.1003574.

Munkvold, G. P., R. L. Hellmich, and L. G. Rice. 1999. Comparison of Fumonisin Concentrations in Kernels of Transgenic Bt Maize Hybrids and Nontransgenic Hybrids. Plant Dis. 83:130-138. doi:10.1094/PDIS.1999.83.2.130.

Olarte R A, Horn B W, Dorner J W, et al. (2012) Effect of sexual recombination on population diversity in aflatoxin production by *Aspergillus flavus* and evidence for cryptic heterokaryosis. *Mol Ecol* 21, 1453-1476.

Olarte, R. A., C. J. Worthington, B. W. Horn, G. G. Moore, R. Singh, J. T. Monacell, et al. 2015. Enhanced diversity and aflatoxigenicity in interspecific hybrids of *Aspergillus flavus* and *Aspergillus parasiticus*. Mol. Ecol. 24:1889-1909. doi:10.1111/mec.13153.

Ortiz-Torres, E. 2006. Effects of crop rotation and nitrogen fertilization on soil nitrate concentration and corn yield. Retrospective Theses and Dissertations. Iowa State University. 1551. lib.dr.iastate.edu/rtd/1551. (accessed 24 Sep. 2018).

Payne, G. A., and M. P. Brown. 1998. Genetics and physiology of aflatoxin biosynthesis. Annu. Rev. Phytopathol. 36:329-362. doi:10.1146/annurev.phyto.36.1.329.

Pereira, E. J. G., M. Picanco, R. N. C. Guedes, F. G. Faleiro, and J. M.d. Araújo. 2000. Susceptibility of maize populations to *Spodoptera frugiperda* Smith and *Helicoverpa zea* Bod. (Lepidoptera: Noctuidae). Acta Scientiarum 22:931-936.

Pitt J I & Hocking A D (2006) Mycotoxins in Australia: biocontrol of aflatoxin in peanuts. Mycopathologia 162 (3):233-243. doi: 10.1007/s11046-006-005900.

Ramirez-Prado, J. H., G. G. Moore, B. W. Horn, and I. Carbone. 2008. Characterization and population analysis of the mating-type genes in *Aspergillus flavus* and *Aspergillus parasiticus*. Fungal Genet. Biol. 45:1292-1299. doi:10.1016/j.fgb.2008.06.007.

Rosenzweig, C., and D. Hillel. 1998. Climate change and the global harvest: Potential impacts of the greenhouse effect on agriculture—Oxford Univ. *Press*, Oxford.

Shotwell, O. L., M. L. Goulden, C. W. Hesseltine, J. W. Dickens, and W. F. Kwolck. 1980. Aflatoxin: Distribution in contaminated corn plants. Cereal Chem. 57:206-208.

Silva, G. A., I. B. Santos, S. O. Campos, T. V. Silva Galdino, E. G. Fidelis Morais, J. C. Martins, et al. 2018. Spatial distribution and losses by grain destroying insects in transgenic corn expressing the toxin Cry1Ab. PLoS One 13:E0201201.

Van der Auwera G A, Carneiro M O, Hartl C, et al. (2013) From FastQ data to high confidence variant calls: the Genome Analysis Toolkit best practices pipeline. *Curr Protoc Bioinformatics* 43, 11.10.11-33.

Vardon, P., C. McLaughlin, and C. Nardinelli. 2003. Potential economic costs of mycotoxins in the United States. Council for Agricultural Science and Technology (CAST). Mycotoxins Risks in Plant, Animal, and Human Systems. Ames, I A.

Vyn, T. J. 2010. Managing residue and tillage on "saturated soils" for optimum production in the short-term and long-term. Illinois Tillage Seminar presentation. Purdue University, West Lafayette, IN pdfs.semanticscholar.org/presentation/59ea/1f0ea70b1dcf8412dd9f9cad4b5713341c0e.pdf.

Wang, T., M. Wang, S. Hu, Y. Xiao, H. Tong, Q. Pan, et al. 2015. Genetic basis of maize kernel starch content revealed by high density single nucleotide polymorphism markers in a recombinant inbred line population. BMC Plant Biol. 15:288. doi:10.1186/s12870-015-0675-2.

Wicklow, D. T. 1994. Preharvest origins of toxigenic fungi in stored grain. In: E. Highley, E. J. Wright, H. J. Banks, and B. R. Champ, editors, Stored Product Protection: Proceedings of the 6th International.

Wogan G N. 1996. Chemical Nature and Biological Effects of the Aflatoxins. *Bacteriological Reviews* 30(2):460-470.

Working Conference on Stored-product Protection. CAB International, Wallingford, UK. p. 1075-1081, spiru.cgahr.ksu.edu/proj/iwcspp/pdf2/6/1075.pdf.

Wogan, G. N. 1966. Chemical nature and biological effects of the aflatoxins. Bacteriol. Rev. 30:460-470.

Wu, F., and P. Khlangwiset. 2010. Health economic impacts and cost effectiveness of aflatoxin reduction strategies in Africa: Case studies in biocontrol and postharvest interventions. Food Addit. Contam. Part A Chem. Anal. Control Expo. Risk Assess. 27:496-509. doi:10.1080/19440040903437865.

Wu F. 2007. Bt corn and impact on mycotoxins. *CAB Reviews: Perspectives in Agriculture, Veterinary Science, Nutrition, and Natural Resources* 2(060):1-8. doi: 10.1079/PAVSNNR20072060.

Yin Y, Yan L, Jiang J, & Ma Z (2008) Biological control of aflatoxin contamination of crops. J Zhejiang Univ Sci B 9(10):787-792.

The foregoing is illustrative of the present invention, and is not to be construed as limiting thereof. The invention is defined by the following claims, with equivalents of the claims to be included therein.

That which is claimed is:

1. A biocontrol method for reducing mycotoxin production in a field population of one or more heterothallic filamentous fungi, the method comprising:
   applying a biocontrol composition to a plant, a plant part and/or a soil, the biocontrol composition comprising an effective amount of propagules of at least two strains of the one or more heterothallic filamentous fungi,
   wherein the at least two strains of the one or more heterothallic filamentous fungi comprises four strains, a first strain, a second strain, a third strain and a fourth strain, each strain comprising a lineage of low mycotoxin production or no mycotoxin production,
   wherein the first and second strains are from the same species and the third and fourth strains are from the same species, and the first and third strains are each from the same genus/species or a different genus/species, and the second and fourth strains are each from the same genus/species or a different genus/species,
   wherein the first and third strains further comprise a MAT1-1 mating type and the second and fourth strains further comprise a MAT1-2 mating type, and
   wherein the amount of propagules of the first strain, second strain, third strain and fourth strain is effective to promote mating between compatible mating partners in the field population and the four strains, thereby increasing the ratio of strains having the lineage of no mycotoxin production or low mycotoxin production in the field population of the heterothallic filamentous fungi and reducing mycotoxin production by the field population of the heterothallic filamentous fungi.

2. The biocontrol method of claim 1, wherein the ratio of the propagules of the first strain to propagules of the second strain in the biocontrol composition is about equal and/or wherein the ratio of propagules of the first, second, third and fourth strains in the biocontrol composition is about equal.

3. The biocontrol method of claim 1, wherein the one or more heterothallic filamentous fungi is from the genus *Fusarium*, and/or the genus *Aspergillus*, optionally wherein the one or more heterothallic filamentous fungi are *A. flavus*.

4. The biocontrol method claim 1, wherein at least one of the at least two strains of the one or more heterothallic filamentous fungi is a native strain that is a lineage of low mycotoxin production or no mycotoxin production, optionally wherein the low mycotoxin production is less than 1% of the highest concentration of mycotoxin production in a sample from the field population.

5. The biocontrol method of claim 1, wherein the mycotoxin is aflatoxin and low aflatoxin production is less than about 10 µg/mL aflatoxin.

6. The biocontrol method of claim 1, wherein the effective amount of propagules of each strain in the biocontrol composition is about $1\times10^4$ cfu per ml to about $5\times10^{10}$ cfu per ml of the biocontrol composition.

7. The biocontrol method of claim 1, wherein the first strain and the second strain have high fertility when crossed, wherein the first strain is MAT1-1 mating type and the propagules are sclerotia and the second strain is MAT1-2 mating type and the propagules are conidia, or wherein the first strain is MAT1-1 mating type and the propagules are conidia and the second strain is MAT1-2 mating type and the propagules are sclerotia.

8. The biocontrol method of claim 1, wherein the mycotoxin is aflatoxin and the aflatoxin production in the field population is reduced to about 1 ppb to about 30 ppb, as measured in a plant sample.

9. The biocontrol method of claim 1, wherein the first strain and the second strain have high fertility when crossed, wherein the first strain is MAT1-1 mating type and the propagules are sclerotia and the second strain is MAT1-2 mating type and the propagules are conidia or wherein the first strain is MAT1-1 mating type and the propagules are conidia and the second strain is MAT1-2 mating type and the propagules are sclerotia, optionally wherein the first strain and/or the second strain comprise(s) one or more genes associated with mycotoxin production, or the first strain, the second strain, the third strain and/or the fourth strain comprise(s) one or more genes associated with mycotoxin production.

10. The biocontrol method of claim 1, wherein the ratio of the low mycotoxin producing lineage to a high mycotoxin producing lineage in the field population of heterothallic filamentous fungi is increased as compared to a control.

11. The biocontrol method of claim 1, wherein the reduction in mycotoxin production is sustained over a period of time from at least about 2 years, optionally about 2 years to about 5 years or more.

12. The biocontrol method of claim 1, wherein the plant is corn, peanut, cotton, wheat, triticale, barley, oat, rice, sorghum, coffee, grape, and/or a tree nut.

* * * * *

UNITED STATES PATENT AND TRADEMARK OFFICE
CERTIFICATE OF CORRECTION

Page 1 of 2

PATENT NO. : 11,985,979 B2
APPLICATION NO. : 17/050751
DATED : May 21, 2024
INVENTOR(S) : Ignazio Carbone It is certified that error appears in the above-identified patent and that said Letters Patent is hereby corrected as shown below:

In the Specification

Column 1, Lines 5-12: Please delete the heading, "STATEMENT OF PRIORITY", the paragraph below it, and the heading, "STATEMENT OF GOVERNMENT SUPPORT" and insert the following:
--STATEMENT OF GOVERNMENT SUPPORT
This invention was made with government support under grant number 2013-68004-20359 awarded by the United States Department of Agriculture's National Institute of Food and Agriculture (USDA NIFA). The government has certain rights in this invention.
STATEMENT OF PRIORITY--

Column 5, Line 66: Please correct "10%, +5%," to read --±10%, ±5%,--

Column 5, Line 67: Please correct "0.1%" to read --±0.1%--

Column 19, Line 29: Please correct "GE102" to read --GH02--

Column 21, Line 20: Please correct "5X10 10 cfu" to read --5X10$^{10}$ cfu--

Column 26, Line 66: Please correct "B 1" to read --B$_1$--

Column 30, Line 26: Please correct "MA TT-2" to read --MAT1-2--

Column 31, Line 64: Please correct "–70%-90%" to read --~70%-90%--

Column 36, Line 46: Please correct "r 2" to read --r$^2$--

Column 36, Line 67: Please correct "AF B 1" to read --AF B$_1$--

Column 44, Line 51: Please correct "B 1" to read --B$_1$--

Signed and Sealed this
Twenty-seventh Day of August, 2024

Katherine Kelly Vidal
*Director of the United States Patent and Trademark Office*

Column 52, Line 3: Please correct "Domer" to read --Dorner--

Column 53, Lines 38-39: Please remove the paragraph break between "Food" and "Safety"

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: M1F primer for MAT1-1

-continued

<400> SEQUENCE: 1
attgcccatt tggccttgaa                                           20

<210> SEQ ID NO 2
<211> LENGTH: 20
<212> TYPE: DNA
<213> ORGANISM: Artificial Sequence
<220> FEATURE:
<223> OTHER INFORMATION: M1R primer for MAT1-1

<400> SEQUENCE: 2
ttgatgacca tgccaccaga                                           20

<210> SEQ ID NO 3
<211> LENGTH: 22
<212> TYPE: DNA
<213> ORGANISM: Artificial Sequence
<220> FEATURE:
<223> OTHER INFORMATION: M2F primer for MAT1-2

<400> SEQUENCE: 3
gcattcatcc tttatcgtca gc                                        22

<210> SEQ ID NO 4
<211> LENGTH: 22
<212> TYPE: DNA
<213> ORGANISM: Artificial Sequence
<220> FEATURE:
<223> OTHER INFORMATION: M2R primer for MAT1-2

<400> SEQUENCE: 4
gcttcttttc ggatggcttg cg                                        22

<210> SEQ ID NO 5
<211> LENGTH: 19
<212> TYPE: DNA
<213> ORGANISM: Artificial Sequence
<220> FEATURE:
<223> OTHER INFORMATION: amdS1 primer for amdS

<400> SEQUENCE: 5
ccatcggtat aggaactga                                            19

<210> SEQ ID NO 6
<211> LENGTH: 18
<212> TYPE: DNA
<213> ORGANISM: Artificial Sequence
<220> FEATURE:
<223> OTHER INFORMATION: amdS2 primer for amdS

<400> SEQUENCE: 6
agggtgccac ggtatgtc                                             18

<210> SEQ ID NO 7
<211> LENGTH: 18
<212> TYPE: DNA
<213> ORGANISM: Artificial Sequence
<220> FEATURE:
<223> OTHER INFORMATION: trpC1 primer for trpC

<400> SEQUENCE: 7
gacgggaaat aggcttcc                                             18

<210> SEQ ID NO 8

<210> SEQ ID NO 8
<211> LENGTH: 18
<212> TYPE: DNA
<213> ORGANISM: Artificial Sequence
<220> FEATURE:
<223> OTHER INFORMATION: trpC3 primer for trpC

<400> SEQUENCE: 8
cgccttggtg ggatggtg                                          18

<210> SEQ ID NO 9
<211> LENGTH: 20
<212> TYPE: DNA
<213> ORGANISM: Artificial Sequence
<220> FEATURE:
<223> OTHER INFORMATION: aflM-F primer for aflM

<400> SEQUENCE: 9
gcttggctct ctcctttgaa                                        20

<210> SEQ ID NO 10
<211> LENGTH: 20
<212> TYPE: DNA
<213> ORGANISM: Artificial Sequence
<220> FEATURE:
<223> OTHER INFORMATION: aflN-R primer for aflM

<400> SEQUENCE: 10
gctgctgagg gagttgaaac                                        20

<210> SEQ ID NO 11
<211> LENGTH: 20
<212> TYPE: DNA
<213> ORGANISM: Artificial Sequence
<220> FEATURE:
<223> OTHER INFORMATION: aflW-F primer for aflW

<400> SEQUENCE: 11
gcacacggtg tggaaagata                                        20

<210> SEQ ID NO 12
<211> LENGTH: 21
<212> TYPE: DNA
<213> ORGANISM: Artificial Sequence
<220> FEATURE:
<223> OTHER INFORMATION: aflX-R primer for aflW

<400> SEQUENCE: 12
gactagtgca cgatgtgcaa c                                      21

<210> SEQ ID NO 13
<211> LENGTH: 19
<212> TYPE: DNA
<213> ORGANISM: Artificial Sequence
<220> FEATURE:
<223> OTHER INFORMATION: XC4-F primer for mfs

<400> SEQUENCE: 13
atcgtgcaga caggaacac                                         19

<210> SEQ ID NO 14
<211> LENGTH: 20
<212> TYPE: DNA
<213> ORGANISM: Artificial Sequence
<220> FEATURE:
<223> OTHER INFORMATION: XC4-R primer for mfs -continued

```
<400> SEQUENCE: 14
ggtgccttgg cctatgcgct                                                  20
```